United States Patent
Andersson et al.

(10) Patent No.: US 10,548,890 B2
(45) Date of Patent: *Feb. 4, 2020

(54) PARENTERAL FORMULATIONS OF LIPOPHILIC PHARMACEUTICAL AGENTS AND METHODS FOR PREPARING AND USING THE SAME

(71) Applicant: Platform Brightworks Two, Ltd., Houston, TX (US)

(72) Inventors: Borje S. Andersson, Houston, TX (US); Benigno C. Valdez, Missouri City, TX (US); Jeffrey Tarrand, Houston, TX (US)

(73) Assignee: Platform Brightworks Two, Ltd., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,908

(22) Filed: Jun. 21, 2018

(65) Prior Publication Data

US 2018/0296556 A1    Oct. 18, 2018

Related U.S. Application Data

(60) Continuation of application No. 15/451,748, filed on Mar. 7, 2017, now Pat. No. 10,028,949, which is a
(Continued)

(51) Int. Cl.
*A61K 9/00* (2006.01)
*A61K 47/10* (2017.01)
(Continued)

(52) U.S. Cl.
CPC .......... *A61K 31/496* (2013.01); *A61K 9/0019* (2013.01); *A61K 9/08* (2013.01);
(Continued)

(58) Field of Classification Search
None
See application file for complete search history.

(56) References Cited

U.S. PATENT DOCUMENTS 4,842,856 A    6/1989  Hoederath et al.
5,430,057 A *  7/1995  Andersson .......... A61K 9/0019
                                                514/517
(Continued)

FOREIGN PATENT DOCUMENTS

DE    2302659    1/1974
EP    0156507    10/1985
(Continued)

OTHER PUBLICATIONS

Winfield et al., Pharmaceutical Practice, 2004, pp. 264-479 (Year: 2004).*

(Continued)

*Primary Examiner* — Carlos A Azpuru
*Assistant Examiner* — Casey S Hagopian
(74) *Attorney, Agent, or Firm* — Parker Highlander PLLC

(57) ABSTRACT

There may be provided compositions of lipophilic pharmaceutical agents with improved solubility and stability. For example, there may be provided a non-aqueous composition that comprises a lipophilic pharmaceutical agent, and an amphiphilic polymeric solvent such as PEG400 but essentially free of organic solvents and non-solubilized particles. The composition may be further diluted with a desired aqueous diluent such as an infusion fluid for parenteral administration to a subject such as a human. The compositions may be useful for the treatment for diseases or conditions that are sensitive to lipophilic agents, such as infectious diseases, malignant or autoimmune diseases.

13 Claims, 17 Drawing Sheets

Related U.S. Application Data division of application No. 15/154,919, filed on May 13, 2016, now Pat. No. 9,724,345, which is a continuation of application No. 13/452,033, filed on Apr. 20, 2012, now Pat. No. 9,364,433.

(60) Provisional application No. 61/480,259, filed on Apr. 28, 2011.

(51) Int. Cl.

| | |
|---|---|
| A61K 9/107 | (2006.01) |
| A61K 31/255 | (2006.01) |
| A61K 9/08 | (2006.01) |
| A61K 47/02 | (2006.01) |
| A61K 47/26 | (2006.01) |
| A61K 31/496 | (2006.01) |

(52) U.S. Cl.
CPC .......... *A61K 9/1075* (2013.01); *A61K 31/255* (2013.01); *A61K 47/02* (2013.01); *A61K 47/10* (2013.01); *A61K 47/26* (2013.01)

(56) References Cited

U.S. PATENT DOCUMENTS

| | | | |
|---|---|---|---|
| 5,559,148 | A | 9/1996 | Andersson et al. |
| 5,869,474 | A | 2/1999 | Goeders |
| 6,720,001 | B2 | 4/2004 | Chen et al. |
| 6,878,693 | B2 | 4/2005 | Goldshtein |
| 7,081,450 | B2 | 7/2006 | Goldshtein |
| 7,179,475 | B1 | 2/2007 | Burnett et al. |
| 9,364,433 | B2 * | 6/2016 | Andersson ............ A61K 9/0019 |
| 9,724,345 | B2 * | 8/2017 | Andersson ............ A61K 9/0019 |
| 2003/0065024 | A1 | 4/2003 | Lambert et al. |
| 2003/0072807 | A1 | 4/2003 | Wong |
| 2004/0063722 | A1 | 4/2004 | Whitefield et al. |
| 2005/0026981 | A1 | 2/2005 | Sugihara et al. |
| 2005/0048126 | A1 | 3/2005 | Rabinow et al. |
| 2005/0191359 | A1 | 9/2005 | Goldshtein et al. |
| 2007/0082870 | A1 | 4/2007 | Buchanan et al. |
| 2007/0249546 | A1 * | 10/2007 | Sawaya ................ A61K 9/0048 514/28 |
| 2009/0048322 | A1 | 2/2009 | Chow et al. |
| 2009/0098200 | A1 | 4/2009 | Krayz et al. |
| 2009/0253712 | A1 | 10/2009 | Kovacs et al. |
| 2009/0264830 | A1 | 10/2009 | Villani |
| 2009/0286799 | A1 | 11/2009 | Jiang |
| 2010/0160442 | A1 | 6/2010 | Ossovskaya et al. |
| 2010/0166872 | A1 | 7/2010 | Singh et al. |
| 2010/0197621 | A1 | 8/2010 | William et al. |
| 2010/0204293 | A1 | 8/2010 | Masuda et al. |
| 2010/0222403 | A1 | 9/2010 | Marcel et al. |
| 2010/0280031 | A1 | 11/2010 | David et al. |
| 2012/0277249 | A1 | 11/2012 | Andersson |

FOREIGN PATENT DOCUMENTS

| | | |
|---|---|---|
| JP | 47-5827 | 3/1972 |
| JP | 63-192714 | 10/1988 |
| JP | 01-242525 | 9/1989 |
| JP | 2002-322056 | 11/2002 |
| JP | 2003-500368 | 1/2003 |
| JP | 2003-509453 | 3/2003 |
| JP | 2008-514645 | 8/2008 |
| JP | 2008-534610 | 8/2008 |
| JP | 2009-523843 | 6/2009 |
| WO | WO 2000/059475 | 10/2000 |
| WO | WO 2000/071163 | 11/2000 |
| WO | WO 2001/021154 | 3/2001 |
| WO | WO 2004-014431 | 2/2004 |
| WO | WO 2004-066998 | 8/2004 |
| WO | WO 2006/016020 | 2/2006 |
| WO | WO 2006/037106 | 4/2006 |
| WO | WO 2006-105399 | 10/2006 |
| WO | WO 2007/083316 | 7/2007 |
| WO | WO 2008/152444 | 12/2008 |
| WO | WO 2009/040818 | 4/2009 |
| WO | WO 2009-031642 | 12/2009 |
| WO | WO 2010-117089 | 10/2010 |
| WO | WO 2010-120755 | 10/2010 |

OTHER PUBLICATIONS

"Azole," retrieved from internet: http://www.merriam-webster.com/dictionary/azole. Retrieved on Nov. 12, 2015.

"Biotin-PEG4-NHS," retrieved from internet: http://www.chempep.com/ChemPep_Products_PEGylation_Reagents.php?id=271611.htm. Retrieved on Nov. 10, 2015.

"Canesten Solution," downloaded from https://www.medicines.org.uk/emc/medicine/4025, three pages, dated Nov. 5, 2016.

"High-Performance Plastics for Healthcare," Solvay Specialty Polymers, 2016.

"Plurol Oleique CC 497," retrieved on Jun. 20, 2016 from http://www.gattefosse.com/en/applications/plurol-oleique-cc497.html, dated 2010.

"Polyethylene glycol," retrieved from internet: https://en.wikipedia.org/wiki/Polyethylene_glycol. Retrieved on Nov. 10, 2015.

"Polymers for Drug Delivery," Sigma-Aldrich Co. LLC, 2015.

"Solutions, Suspensions and Emulsions," retrieved from internet: http://cheminnerweb.ukzn.ac.za/files/solutions,%20suspensions%20and%20emulsions.pdf, Retrieved on May 14, 2016.

Benet and Sheiner, "Pharmacokinetics: The dynamics of drug absorption, distribution, and elimination", *Goodman and Gilman's the Pharmacological Basis of Therapeutics*, Goodman et al. (Eds.), 7th Edition. MacMillan Publishing Co: New York, 1985. Print.

Canesten Solution leaflet, Bayer AG, Dec. 2009.

Danafar, "MPEG-PCL copolymeric nanoparticles in drug delivery systems," Cogent Med., 3(1142411):1-11, 2016.

Devi et al., "Poloxamer: A Novel Functional Molecule for Drug Delivery and Gene Therapy," *J. Pharm. Sci. & Res.*, 5(8):159-165, 2013.

Evensen et al., "Experimental thrombocytopenia induced by busulphan (myleran) in rabbits: extremely low platelet levels and intact plasma clotting system," *Thromb Diath Haemorrh.*, 19(3):570-577, 1968.

Extended European Search Report issued in European Application No. 11849408.7, dated Jun. 6, 2014.

Extended European Search Report issued in European Application No. 17175794.1, dated Sep. 22, 2017.

Greer, "Posaconazole (Noxafil): a new triazole antifungal agent", Baylor Univ Med Center Proc., 20:188-196, 2007.

History of SPC revisions for Canesten Solution, downloaded from http://www.medicines.org.uk/emc/history/4025, last updated on Aug. 4, 2015.

Kadajji and Betageri, "Water Soluble Polymers for Pharmaceutical Applications," *Polymers*, 3:1972-2009, 2011.

Office Action issued in Australian Application No. 2012250050, dated May 11, 2016.

Office Action issued in Canadian Application No. 2,834,262, dated May 22, 2018.

Office Action issued in Canadian Application No. 2,834,262, dated Mar. 8, 2019.

Office Action issued in Chinese Application No. 2011800678245, dated Sep. 30, 2014, and English language translation thereof.

Office Action issued in Chinese Application No. 201280032690.8, and English language translation thereof, dated Jan. 21, 2015.

Office Action issued in Chinese Application No. 201280032690.8, and English language translation thereof, dated Sep. 23, 2015.

Office Action issued in Chinese Application No. 201280032690.8, and English language translation thereof, dated Dec. 19, 2016.

Office Action issued in Chinese Application No. 201280032690.8, dated Dec. 19, 2016.

Office Action issued in Japanese Application No. 2013-544816, dated Sep. 29, 2015, and English language translation thereof.

Office Action issued in Japanese Application No. 2014-508441, and English language translation thereof, dated Dec. 7, 2015.

(56) References Cited

OTHER PUBLICATIONS

Office Action issued in Japanese Application No. 2014-508441, dated Jun. 24, 2016.
Office Action issued in New Zealand Application No. 613167, dated Mar. 4, 2014.
Office Action issued in U.S. Appl. No. 13/452,033, dated Feb. 25, 2014.
Office Action issued in U.S. Appl. No. 13/452,033, dated Jun. 13, 2014.
Office Action issued in U.S. Appl. No. 13/452,033, dated Jan. 5, 2015.
Office Action issued in U.S. Appl. No. 13/452,033, dated Mar. 21, 2013.
Office Action issued in U.S. Appl. No. 13/452,033, dated Sep. 16, 2013.
Office Action issued in U.S. Appl. No. 13/994,152, dated Apr. 15, 2015.
Office Action issued in U.S. Appl. No. 13/994,152, dated May 19, 2016.
Office Action issued in U.S. Appl. No. 13/994,152, dated Nov. 17, 2015.
Office Action issued in U.S. Appl. No. 15/154,919, dated Oct. 4, 2016.
Office Action issued in U.S. Appl. No. 15/451,748, dated Jun. 26, 2017.
PCT International Preliminary Report on Patentability, issued in International Application No. PCT/US2011/065422, dated Jun. 27, 2013.
PCT International Search Report and Written Opinion issued in International Application No. PCT/US2012/034361, dated Aug. 3, 2012.
PCT International Search Report and Written Opinion, issued in International Application No. PCT/US2011/065422, dated Aug. 3, 2012.
Pu et al., "Formulation of nanosuspensions as a new approach for the delivery of poorly soluble drugs," *Current Nanoscience*, 5:417-427, 2009.
Rowe et al., "Polyethylene Glycol, Handbook of Pharmaceutical Excipients," Pharmaceutical Press and the American Pharmacists Association, Fifth Edition, pp. 545-550, 2006.
Rytting et al., "Aqueous and cosolvent solubility data for drug-like organic compounds," *The AAPS Journal*, 7(1):E78-E105, 2005.
Willems et al., "Itraconazole oral solutions and intravenous formulations: a review of pharmacokinetics and pharmacodynamics", *J Clin Pharm Ther.*, 26(3):159-169, 2001.
Winfield et al., "Pharmaceutical Practice," Churchill Livingstone, pp. 264-279, 2004.
Zhou et al., "A pharmacokinetic study of intravenous itraconazole followed by oral administration of itraconazole capsules in patients with advanced human immunodeficiency virus infection", *Clin Pharmacol.*, 38(7):593-602, 1998.

* cited by examiner

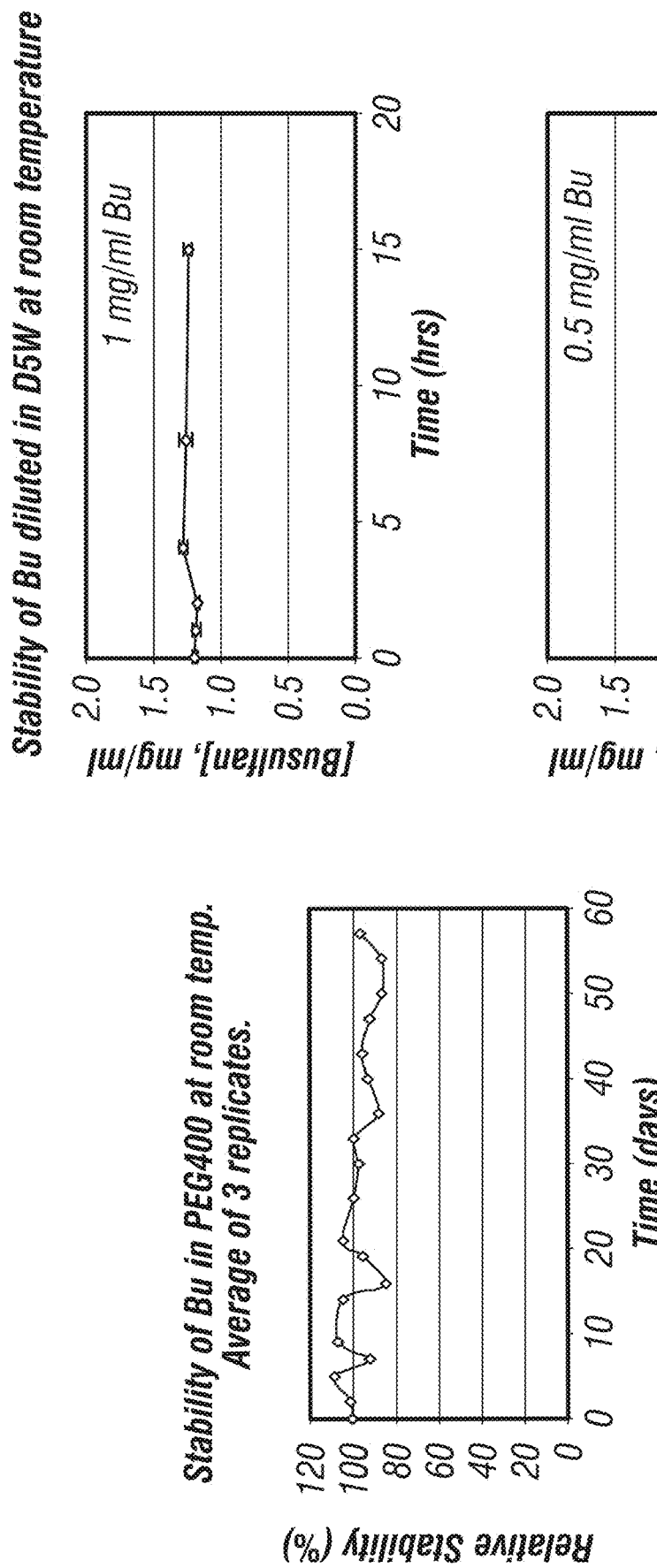
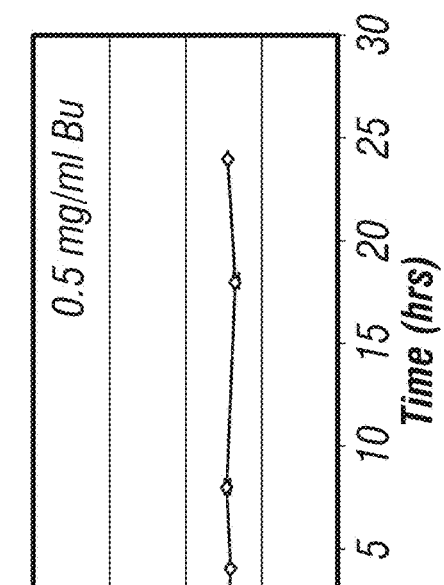
FIG. 1B
FIG. 1A

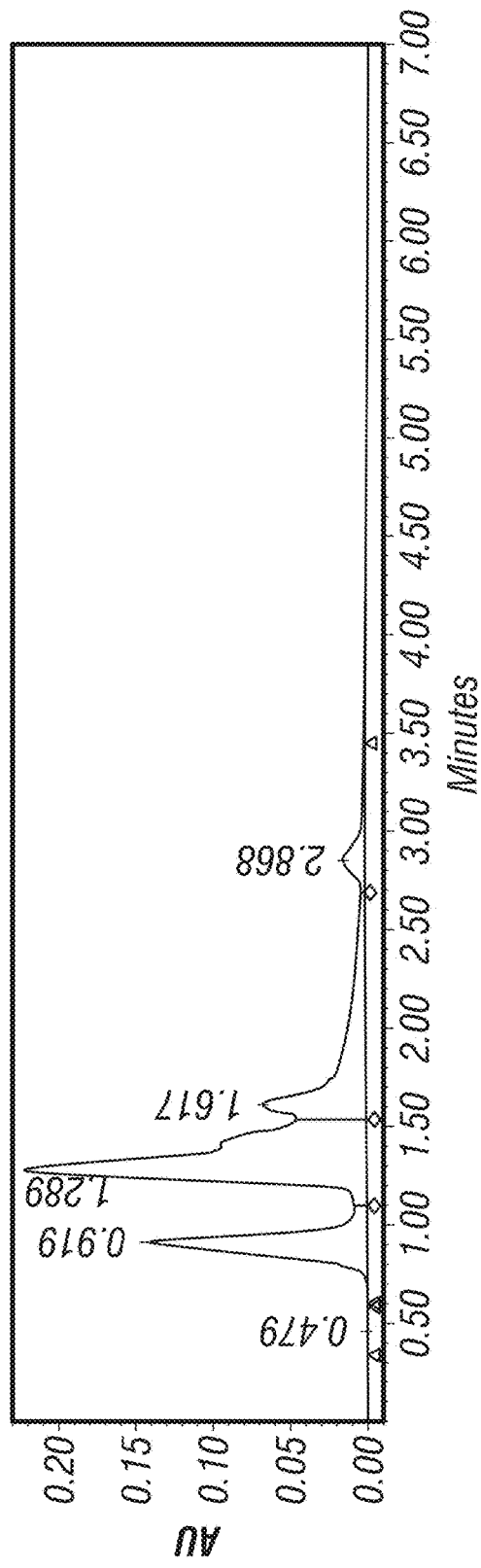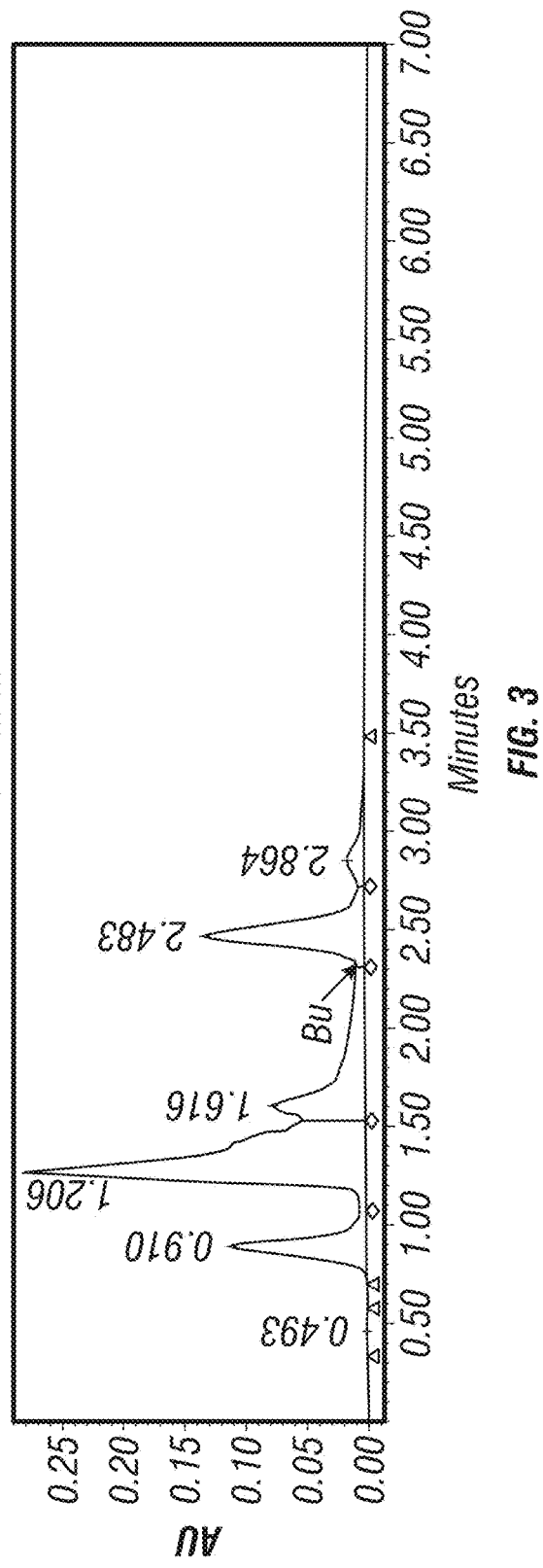
FIG. 3

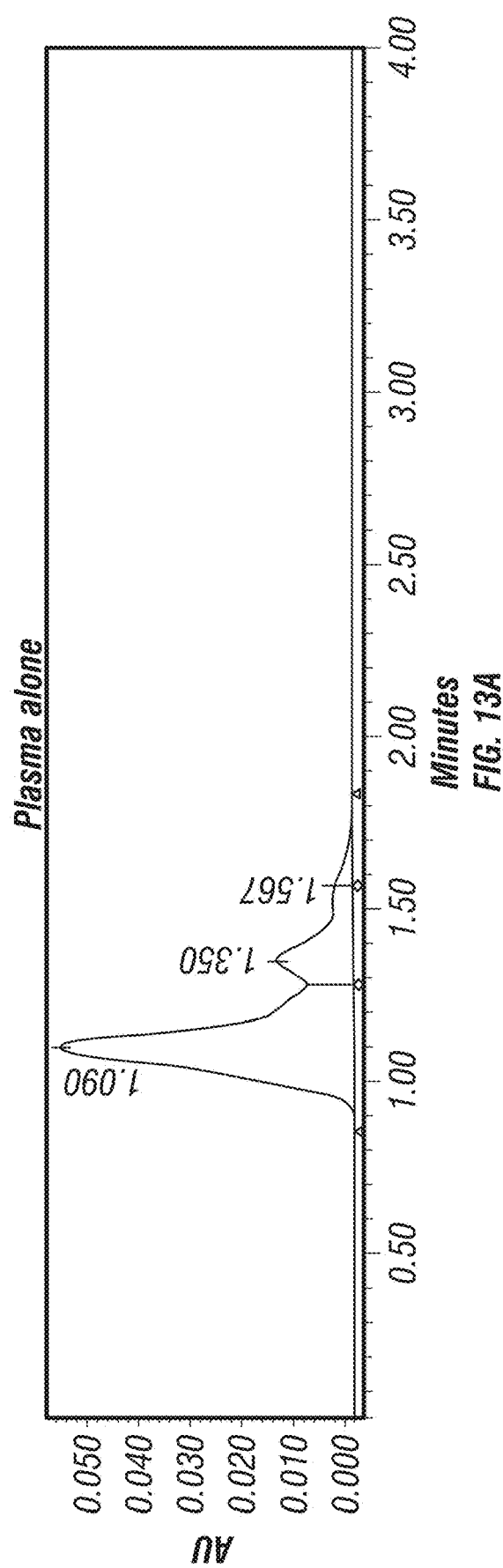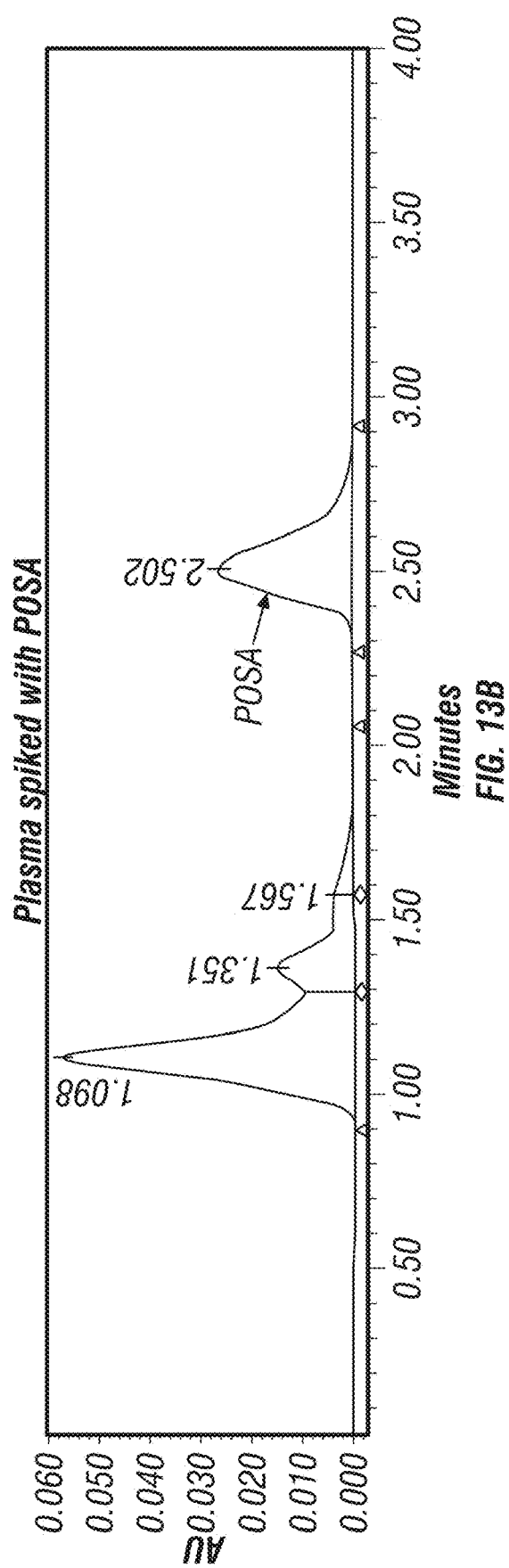

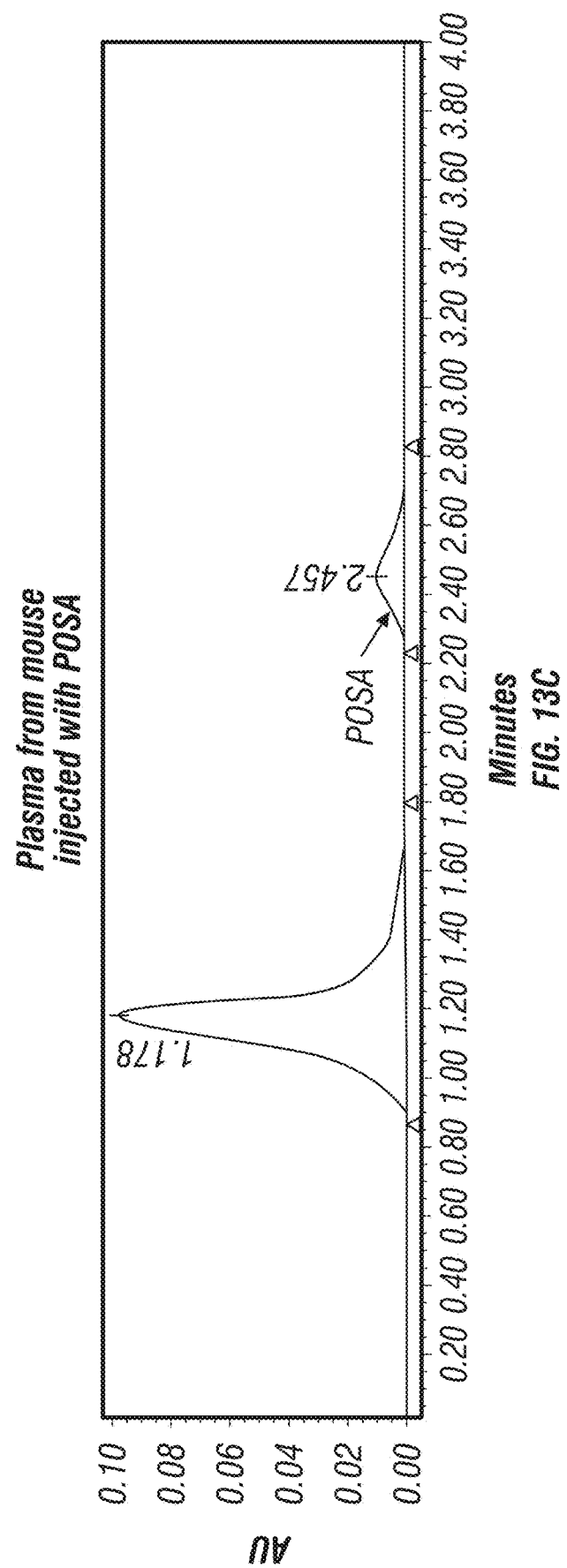

PARENTERAL FORMULATIONS OF LIPOPHILIC PHARMACEUTICAL AGENTS AND METHODS FOR PREPARING AND USING THE SAME

This application is a continuation of U.S. application Ser. No. 15/451,748, filed Mar. 7, 2017, which is a divisional of U.S. application Ser. No. 15/154,919, filed May 13, 2016, now U.S. Pat. No. 9,724,345, which is a continuation of U.S. application Ser. No. 13/452,033, filed Apr. 20, 2012, now U.S. Pat. No. 9,364,433, which claims priority to U.S. Provisional Application No. 61/480,259, filed Apr. 28, 2011, each of which is hereby incorporated by reference.

BACKGROUND OF THE INVENTION

Field of the Invention

The present invention is related generally to an improved composition and method for preparing parenteral formulations comprising solubilized lipophilic pharmaceutical agents and using these formulations in treatment of diseases such as malignant and autoimmune diseases, infectious disorders, or for use in conditioning therapy preceding hematopoietic stem cell transplantation.

Description of Related Art

Lipophilic drug substances having low water solubility are a growing class of drugs with increasing applicability in a variety of therapeutic areas for a variety of pathologies. Many compounds approved for pharmaceutical use are lipophilic compounds with limited solubility and bioavailability. Relatively insoluble compounds, i.e., solubility in water of less than 200 µg/mL may show promising pharmaceutical activity, but their development as pharmaceuticals, particularly in parenteral dosage form, present a significant challenge to the pharmaceutical industry. Among the main barriers for effective drug delivery are solubility and stability. To be absorbed in the human body, a compound has to be soluble in both water and fats (lipids). However, solubility in water is often associated with poor fat solubility and vice-versa.

Solubility and stability are, therefore, major obstacles hindering the development of therapeutic agents. Aqueous solubility is a necessary but frequently elusive property for formulations of the complex organic structures found in pharmaceuticals. Traditional formulation systems for very insoluble drugs have involved a combination of organic solvents, surfactants and extreme pH conditions. These formulations are often irritating to the patient and may cause adverse reactions. At times, these methods are inadequate for solubilizing enough of a quantity of a drug for a parenteral formulation.

Therefore, there exists a need for compositions and methods involving formulations comprising solubilized and stable lipophilic pharmaceutical agents, such as busulfan.

As a particular example, the bifunctional DNA-alkylating agent Busulfan (Bu; 1,4-butanediol dimethanesulfonate, aka Butane-1,4-diyl dimetanesulfonate; $C_6H_{14}O_6S_2$) has over the last several decades earned an impressive reputation for its chemotherapeutic efficacy against numerous malignant diseases. This is most readily appreciated, however, in its activity against myeloid neoplasms, such as that exemplified by chronic myelogenous leukemia (CIVIL) (Haddow and Timmis, 1953; Hoffman et al., 1991).

The therapeutic benefit obtained with Bu in single agent (alkylating agent) therapy in treatment of CML was achieved through its general myelotoxicity. It has lately been increasingly replaced by targeted therapy with tyrosine kinase inhibitors, which may selectively down-regulate the aberrant proliferation of the malignant clone(s) and restore normal polyclonal hematopoiesis.

On the other hand it was recognized by Santos and coworkers, and further refined by Tutschka and coworkers, that the remarkably potent (and selective) myelosuppressive activity of Bu, in addition to its pronounced antileukemic efficacy, makes it an almost ideal agent for use in pretransplant conditioning therapy for patients undergoing hematopoietic stem cell transplantation for malignant-, autoimmune-, or genetic diseases provided that its myelosuppressive activity was paired with the immunosuppressive activity of a second agent, cyclophosphamide (Cy), was usually the preferred "partner" in this setting. Variants of this "Bu-Cy" combination quickly became recognized as (an) acceptable alternative(s) to the (at the time) more commonly used combinations of total body irradiation (TBI) and Cy (Santos and Tutschka, 1974; Santos et al., 1974; Tutschka et al., 1987; Ciurea et al., 2009). When more experience accumulated with the Bu-Cy combinations it became apparent that the unpredictable intestinal absorption and erratic bioavailability of oral Bu was a contributory reason for high peri-transplant morbidity and mortality, most importantly caused by serious liver toxicity or drug-induced toxic hepatitis, clinically referred to as veno-occlusive disease of the liver (VOD). The risk of dying of VOD and other treatment-related complications was reported to be as high as 30-50% already within the first 100 days after the HSCT (Blaise et al., 1992; Devergie et al., 1995; Hartman et al., 1998; Socie et al., 2001; Ciurea et al., 2009). The toxicity from virtually any myeloablative preparative regimen has been associated with the development of VOD (Jones et al., 1987; McDonald et al., 1993; Bearman, 1995), but VOD and/or hepato-renal failure after administration of oral Bu (combined with Cy) has commonly been considered a "trade-mark" toxicity associated with high-dose Bu (both the original BuCy4 [4 days of Cy] and the variant BuCy2 [2 days of Cy] regimens) (Santos et al., 1983; Tutschka et al., 1987; Grochow et al., 1989; Grochow, 1993; Slattery et al., 1997; Dix et al., 1996). Additionally, oral Bu is associated with a hepatic first-pass extraction effect that results in locally high Bu concentrations in the portal-hepatic venous system, and this may contribute to the risk for VOD (Peters et al., 1987). However, in addition to Bu, Cy is clearly hepatotoxic. The findings of McDonald and coworkers suggest that inter-individual differences in metabolic drug handling are of importance for developing VOD, such that, in addition to Bu, Cy conceivably contributes to the overall risk of VOD (McDonald et al., 2003). Thus, the risk of VOD is related to the drug-induced metabolic stress on the liver, especially when both agents depend on hepatic glutathione (GSH) stores and on hepatic Glutathione-S-Transferase (GST) activity for their detoxification (McDonald et al., 2003; Hassan et al., 2000).

In addition to VOD, neurotoxicity was associated with Bu in animals (Deeg et al., 1999). Convulsions in a human receiving oral Bu were first reported by Marcus and Goldman (1984). The incidence of neurotoxicity, especially serious generalized seizure activity, after Bu-based conditioning therapy has been estimated to be as high as 10% in adults (Santos, 1989), and approximately 7% in children (Vassal et al., 1990). Vassal et al reported that higher doses (>600 mg/m² or 16 mg/kg) are associated with an increased probability of neurotoxic manifestations (Vassal et al., 1989). Seizures are more common in older patients, and they appear to be dose-dependent both in adults and children. Seizures are related to Bu's limited plasma binding and therefore its ability to cross the blood-brain-barrer (Vassal et al., 1990; Vassal et al., 1989; Hassan et al., 1989; Meloni et al., 1992). In adults, seizures typically occur in the $3^{rd}$ or $4^{th}$ day of Bu administration, probably as a result of tissue drug accumulation (Marcus and Goldman, 1984; Hassan et al., 1989; Meloni et al., 1992; Kobayashi et al., 1998; Martell et al., 1987; Sureda et al., 1989). Even without overt seizure activity EEG abnormalities occur in up to 60% of patients (Kobayashi et al., 1998). These problems necessitate that various anticonvulsant medications be used for seizure prophylaxis (Meloni et al., 1992; Kobayashi et al., 1998; Grigg et al., 1989; Meloni et al., 1995; Chan et al., 2002; Hassan et al., 1993).

The practical limitations in using oral Bu in high-dose pretransplantation conditioning therapy are primarily related to its unpredictable and erratic bioavailability due to variable intestinal absorption. Available clinical trial data and concerns related to oral Bu toxicity formed the basis for our hypothesis that an IV Bu formulation might cause less stress to the liver, since parenteral administration will yield complete dose assurance with 100% bioavailability as well as circumvent the hepatic first-pass extraction of oral drug that is absorbed from the intestinal tract through the portal-hepatic venous system. This realization prompted the design of an IV Bu formulation to achieve controlled administration (Bhagwatwar et al., 1996; Andersson et al., 2000). The DMA-based IV Bu-formulation was approved by the US FDA in 1999. It has rapidly replaced oral Bu in pre-HSCT chemotherapy, mostly in the IV BuCy2 regimen (Andersson et al., 2002).

So far, IV BuCy2 has been compared with oral BuCy2 in 6 retrospective studies, all showing superiority of IV BuCy2 with regards to the development of VOD and early transplant-related mortality (Kashyap et al., 2002; Thall et al., 2004; Kim et al., 2005; Lee et al., 2005; Aggarwal et al., 2006; Dean et al., 2010). The introduction of IV Bu with Cy appeared to improve the safety of the Bu-Cy(2) regimen(s), however early regimen-related toxicity was/is still of concern. As noted above, it had become apparent through the work of McDonald and coworkers that Cy, when used in high doses in the pretransplant setting, contributed to overall hepatotoxicity (McDonald et al., 1993; McDonald et al., 2003; DeLeve et al., 2002). The activated cytotoxic metabolites of Cy (especially o-carboxyethylphosphoramide mustard and acrolein) likely contribute to VOD in the Bu-Cy2 conditioning regimen through the need for GSH in their metabolic detoxification. As an extension of these observations, the risk for VOD could conceivably be decreased by substituting Cy with an immunosuppressive agent from a different class of drugs without hepatotoxicity, such as Fludarabine (Flu), which does not utilize GSH in its metabolism, and which is virtually non-toxic to the liver. Thus, Russell and colleagues reported on a myeloablative conditioning regimen using IV Bu-Flu and antithymocyte globulin (ATG) in a convenient once-daily dosing schedule (Russell et al., 2002). In subsequent, disease-specific studies performed at the M.D. Anderson Cancer Center (MDACC), Flu and IV Bu were also given once daily (De Lima et al., 2004; Andersson et al., 2008). Ninety-six patients with AML/MDS were treated in this study where ATG was added only for matched unrelated donor- and one antigen mismatched sibling donor-transplant patients (De Lima et al., 2004). Stomatitis was commonly seen, and VOD and neurological side effects were still encountered in a fraction of patients. The majority of patients in the first study and 18% in the second study had transient elevations of ALT, while about 10% experienced a significant increase in bilirubin as additional signs of stress on liver function within one to two weeks after transplant (Russell et al., 2002; De Lima et al., 2004). Three of the first 166 (1.8%) patients treated in these two trials developed clinically significant VOD, and one of them died (0.6%). Neurotoxicity was uncommon; 4% of patients developed a "hand-foot" syndrome and two patients had seizures (Russell et al., 2002; De Lima et al., 2004; Andersson et al., 2008). Interestingly, the pattern of liver toxicity appears somewhat different than what was previously experienced with oral Bu; commonly there is a "silent hyperbilirubinemia" in about a third of the patients, having its onset within about a week of IV Bu delivery, and if clinical VOD occurs, it now commonly happens at a later time than what was previously encountered. Thus, clinically diagnosed VOD now occurred in a fraction of patients as late as two months after the HSCT (Andersson, unpublished data).

The parenteral Bu-formulation was developed to achieve 100% bioavailability with complete dose assurance, and to simultaneously eliminate the hepatic first-pass effect which may contribute to the high risk of mortal liver failure after oral high-dose Bu (Bhagwatwar et al., 1996; U.S. Pat. Nos. 5,430,057; 5,559,148).

The currently available IV Bu formulation has a composite solvent vehicle based on N,N-Dimethylacetamide (DMA) and Polyethylene-glycol 400 (PEG/PEG400) ("DMA-Bu") (Bhagwatwar et al., 1996; U.S. Pat. Nos. 5,430,057; 5,559,148). Although several clinical studies confirmed that this DMA-Bu formulation is better tolerated and yields improved clinical results of patients transplanted for various types of leukemia and lymphomas (Kashyap et al., 2002; Thall et al., 2004; Kim et al., 2005; Lee et al., 2005; Aggarwal et al., 2006; Dean et al., 2010; DeLeve et al., 2002; Russell et al., 2002; De Lima et al., 2004; Andersson et al., 2008; Chae et al., 2007; Bredeson et al., 2008; Shimoni et al., 2006; Shimoni et al., 2010; Santarone et al., 2011), there was already from the early human trials apprehension about administering a large amount of DMA in humans, since DMA is recognized as a potentially quite toxic solvent (Dwivedi, 2002; VICH Steering Committee, 2010; The Food and Drug Administration, 2010; The Office of Environmental Health Hazard Assessment, 2010). These concerns are justifiably augmented by the possible additive or even synergistic (adverse) interaction(s) between DMA and Bu, since both agents exert significant metabolic stress on the liver. Even though the overall incidence of serious hepatic toxicity is decreased when comparing the oral and IV Bu-Cy2 regimens (Kashyap et al., 2002; Thall et al., 2004; Kim et al., 2005; Lee et al., 2005; Aggarwal et al., 2006; Dean et al., 2010), there is a (sub-) group of patients who suffer serious, life-threatening, or even lethal, hepatic toxicity after receiving the IV Bu-Cy2 and IV Bu-Flu variant regimens (Kashyap et al., 2002; Thall et al., 2004; Kim et al., 2005; Lee et al., 2005; Aggarwal et al., 2006; Dean et al., 2010; Russell et al., 2002; De Lima et al., 2004; Andersson et al., 2008; Chae et al., 2007; Bredeson et al., 2008; Shimoni et al., 2006; Shimoni et al., 2010; Santarone et al., 2011).

It may be important to remember, that the hepatic toxicity profile of IV DMA-Bu is qualitatively somewhat different from that experienced with oral Bu; oral Bu toxicity is manifested as an early, progressive increase in bilirubin, ALT, and AST, typically emerging within the first 10 days following oral Bu administration. This either rapidly progresses to life-threatening or lethal hepato-renal failure or, alternatively the patient starts improving and is clinically significantly better at about 3 weeks after transplantation;

the likelihood for complete recovery is now excellent (McDonald et al., 1993; Bearman, 1995; McDonald et al., 2003; DeLeve et al., 2002). In contrast, when the IV DMA-Bu is utilized, there is typically a high (about 30-40%) incidence of "silent hyperbilirubinemia" that appears within 10-14 days following IV DMA-Bu administration. This is likely to resolve in the next several days (up to about a week to ten days), but serious treatment-related hepatic toxicity, VOD, may instead manifest itself as late as 8-10 weeks post-HSCT (Russell et al., 2002; De Lima et al., 2004; Andersson et al., 2008). The inventors hypothesized that the changing clinical toxicity pattern may result from an adverse interaction between Bu and DMA. The latter solvent has demonstrated hepatic, renal and neurologic toxicity in humans, in addition to causing growth retardation and decreased weight gain using rodents and logomorphs in experimental settings (Malley et al., 1995; Kennedy, 1986; Klimisch and Hellwig, 2000; Okuda et al., 2006; Valentine et al., 1997; Kennedy, 2001). In addition, there is at least one report of serious toxic hepatitis with an incidence of about 3-5% in factory workers that were occupationally exposed to high concentrations of vaporized DMA in a commercial plastics production facility (Choi et al., 2001). Finally, in a clinical study of DMA as an anti-cancer agent, the acute, dose-limiting toxicity of DMA was mental confusion/coma, and DMA has also been described as a hallucinogenic agent (Weiss et al., 1962a; Weiss et al., 1962b). The concern about (a) serious adverse interaction(s) between Bu and DMA led one group to investigate the possible clinical adverse interaction(s) when IV DMA-Bu formulation is combined with Cy in pretransplant conditioning therapy (Hempel et al., 2007). These investigators concluded, that although there might be justifiable concerns about (an) adverse interaction(s) between Bu and DMA and Cy, the available IV DMA-Bu formulation is still safer than oral Bu when used in pretransplant conditioning therapy (Hempel et al., 2007). Other investigators demonstrated that under carefully controlled conditions Bu and DMA have a significant (synergistic) cytotoxic interaction (Sadeghi et al., 1999). It is conceivable, that a potentially serious adverse clinical interaction between the two agents is obscured by the naturally occurring interindividual heterogeneity in drug metabolism in the clinical situation. Further, the only comparison that is possible when trying to identify a suitable reference population for evaluation of clinical safety of IV DMA-Bu is the historical comparison with patients treated with oral Bu-based high-dose chemotherapy. Because of the excessively high risk for serious treatment-related complications after high-dose oral Bu, such a comparison will undoubtedly favor DMA-Bu, but it does not address the contribution of DMA to the overall toxicity profile of IV DMA-Bu. Presently such an evaluation is not possible to perform, since the only available IV Bu formulation has a large amount of DMA in the solvent vehicle.

When all available data are considered, it is apparent that inclusion of (a) solvent(s) that impose(s) metabolic stress on the liver, such as DMA, will likely increase the risk for clinically significant liver- and/or multiorgan toxicity, thereby increasing the overall risk to the patient for treatment-regimen related morbidity and mortality. This risk is, however, downplayed by the use of a historical comparator group that was subjected to a significantly worse therapeutic alternative.

The well documented toxicity profile of DMA has rendered it a designation as a Class II agent from the International Cooperation on Harmonization of Technical requirements for Registration of Veterinary Medicinal Products. This designation means that DMA is an agent whose utilization in manufacturing of pharmaceutical formulations should be strictly limited and, if at all possible, it should be avoided (Dwivedi, 2002; VICH Steering Committee, 2010; The Food and Drug Administration, 2010; The Office of Environmental Health Hazard Assessment, 2010).

Therefore, based on the 1) mostly occupational literature reports of serious DMA-induced normal-organ (liver) toxicity, and 2) the acute changes in level of consciousness and/or hallucinations when administered in humans, 3) the occasional later occurring cases of serious, life-threatening as well as lethal, liver toxicity experienced with use of the IV DMA-Bu formulation, and finally 4) the existing FDA-guidelines, there is a need to design an alternative parenteral Bu formulation that is free from DMA. The availability of such a formulation would serve to further improve the clinical safety profile of parenterally administered Bu, such that its full therapeutic potential can be experienced without added concern for serious normal organ toxicity that is imposed by (a) component(s) of the composite solvent vehicle.

SUMMARY OF THE INVENTION

Certain aspects of the present invention provide pharmaceutically stable and parenterally acceptable novel formulations of lipophilic pharmaceutical agents. Without wishing to be bound by theory, the formulations of the invention may be partly based on the principle of cosolvency. Particularly the invention is based, at least in part, on the discovery that a lipophilic pharmaceutical agent could be stable and solubilized at a higher concentration in a non-aqueous solvent by a specific cosolvency approach. The approach may involve the use of a volatile organic solvent to facilitate solubilization of the lipophilic agent in a non-aqueous solvent such as PEG400, followed by the removal of the volatile organic solvent to provide a non-aqueous composition of the lipophilic agent with improved solubility and stability. Optionally, such non-aqueous composition may be further diluted with an aqueous solvent while the lipophilic agent could remain stable and solubilized. Examples of the compositions may be pharmaceutically acceptable, nontoxic, and stable for many hours at room temperature, such as the busulfan formulation.

The invention relates to pharmaceutical formulations, and more specifically, to parenteral formulations of lipophilic agents such as busulfan (Bu), an azole agent like Posaconazole, Itraconazole or related anti-infectious agents. In certain aspects of the invention, parenteral formulations may be useful for treatment of any conditions or diseases that are sensitive or responsive to the lipophilic agents, including, but not limited to, the treatment and/or suppression of malignant or autoimmune diseases, for use in conditioning therapy of patients undergoing hematopoietic stem cell transplantation (HSCT) or for the treatment and/or suppression of systemic infections with yeast, molds and other organisms that are sensitive to anti-infectious agents.

Such parenteral formulations could avoid the undesirable, erratic bioavailability, and unpredictable hepatic first pass extraction of oral preparations and in view of being truly solubilized the agents are now free from the shortcomings experienced with the delivery of particulate matter, such as colloidal, nano-particular or micro-particular suspensions, or microcrystalline suspensions of pharmaceutically active agents. In a particular aspect, the busulfan formulation may abrogate the concern for acute, as well as long-term, or chronic, toxicity related to the inclusion of the organic solvent N, N-dimethylacetamide (DMA), as being the major component in the only commercially available parenteral Bu formulation.

Accordingly, one embodiment of the invention is directed to a non-aqueous, homogeneous solution comprising a solubilized lipophilic pharmaceutical agent and a non-aqueous amphiphilic solvent, such as an amphiphilic liquid polymeric solvent. Without wishing to be bound by theory, it is contemplated that the agent may bind to the amphiphilic solvent by electrostatic interactions to achieve high aqueous solubility and stability. Formulations of the present invention are essentially free of non-polymeric organic solvents, water and non-solubilized particles, wherein the solubilized lipophilic pharmaceutical agent has a concentration of at least about 0.5 mg/mL, and further wherein the solution remains stable and essentially free of non-solubilized particles for at least 40 days and preferably at least 60 days. Studies are described hereinbelow demonstrating exemplary formulations that maintain such properties when stored for at least 40 and even up to 60 days at room temperature when tested at 5 mg pharmaceutical agent/ml of amphiphilic liquid polymeric solvent.

In certain aspects, the solution of any formulation described herein may be essentially free of DMA or other polymeric or non-polymeric organic solvents. In particular aspects, the formulation may be essentially free of water or obviate the need of the use of water in formulation preparation. Non-solubilized particles, such as colloidal particles, nano-particles or micro-particles, or microcrystalline particles, may also be essentially non-existent in the solution of any formulation described herein. The solution composition may optionally further comprise an aqueous diluent such as an aqueous infusion fluid, which may be used to facilitate the subsequent systemic administration to a mammal, preferably a human or a (large) domestic animal. In a further aspect, an aqueous, homogeneous, pharmaceutically-acceptable parenteral formulation may be prepared by a process comprising obtaining a solution described above and diluting the solution with a desired aqueous diluent.

In certain aspects, the invention may be directed to compositions and methods for parenteral formulation preparation. The novel solvent vehicles of the invention may be used to facilitate parenteral administration of other hard-to solubilize, aka "water-insoluble", drugs. Accordingly, another embodiment of the invention includes a composition for parenteral use comprising: a water-insoluble/lipophilic pharmaceutically active agent, and a first solvent, the first solvent comprising an organic solvent such as acetone or chloroform together with a second amphiphilic solvent, such as PEG. The pharmaceutically active agent may be dissolved in the first solvent, and after solubilization it may be mixed with the second solvent. The first organic (volatile) solvent may be then removed (e.g., evaporated under vacuum) and the pharmaceutically active agent may remain electrostatically attracted and bound to, and stably dissolved in, the second solvent/PEG. The clinical use-composition optionally further comprises a secondary diluent such as an aqueous infusion fluid, such as normal saline or dextrose in water, either by itself or pre-mixed with a small amount (10-25%, v/v) of amphiphilic polymer such as PEG. Due to the electrostatic attraction between the second amphiphilic solvent (PEG) and the pharmaceutically active agent this drug-PEG complex can be diluted in the aqueous diluent without immediate precipitation of the pharmaceutically active agent.

In a particular aspect, the composition may comprise Bu and a first volatile organic solvent such as acetone. The Bu may be dissolved in the volatile organic solvent such as acetone and then mixed with an amphiphilic solvent such as PEG400. Subsequently, and taking advantage of the low boiling point of the volatile organic solvent, the volatile organic solvent may be removed, e.g., by evaporation under vacuum at RT. At the end of this phase, the Bu could be completely and stably dissolved in the amphiphilic solvent such as PEG400. Prior to clinical administration, the composition may be optionally diluted with a secondary diluent such as an aqueous infusion fluid, e.g., normal saline (NS) or 5-10% dextrose in water (D5W, D10W), as final diluent(s).

The solubilized lipophilic pharmaceutical agent in any solution, composition or formulation described herein may have a concentration of at least or up to about 0.2, 0.3, 0.4, 0.5, 0.6, 0.7, 0.8, 0.9, 1, 1.5, 2, 2.5, 3, 3.5, 4, 4.5, 5, 5.5, 6, 7, 8, 9, 10, 11, 12, 13, 14, 15, 16, 17, 18, 19, 20, 25, 30, 40, 50, 60, 70, 80, 90, 100 mg/mL (or mol/L) or any intermediate ranges or numbers. In particular aspects, the solubilized lipophilic pharmaceutical agent may have a concentration of about 1 to 10 mg/mL or about 3 to 9 mg/mL.

For example, the lipophilic pharmaceutical agents that can be used herein include lipophilic compounds having solubility in an aqueous solvent of less than about 0.01, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 7, 8, 9, 10 mg/mL (or mol/L) or any range derivable therein, preferably less than 10 mg/mL, more preferably less than about 1 mg/ml and even less than about 0.1 mg/mL.

In certain aspects, formulations described herein could retain at least 50, 60, 70, 80, 90, 95, 99, 99.9, 100% activity (or any value or range derivable therein) of the pharmaceutical agents during or after preparation. For example, the novel Bu formulation retains full in vitro cytotoxic activity in tissue cultures utilizing continuously growing human leukemia cell lines as targets, demonstrating that the novel Bu formulations do not lose cytotoxic activity due to chemical degradation or physical precipitation when solubilized. Formulations described herein may be used intravascularly, and have been successfully used for intravenous (IV) administration in a murine model. Preliminary pharmacokinetics obtained in a mouse model with an exemplary formulation of the invention has yielded detectable cytotoxic Bu concentrations for several hours after administration.

Suitable lipophilic agents may be any poorly water-soluble, biologically active agents or a salt, isomer, ester, ether or other derivative thereof, which include, but are not limited to, anticancer agents, antifungal agents, psychiatric agents such as analgesics, consciousness level-altering agents such as anesthetic agents or hypnotics, nonsteroidal antiinflammatory agents, anthelminthics, antiacne agents, antianginal agents, antiarrhythmic agents, anti-asthma agents, antibacterial agents, anti-benign prostate hypertrophy agents, anticoagulants, antidepressants, antidiabetics, antiemetics, antiepileptics, anti gout agents, antihypertensive agents, antiinflammatory agents, antimalarials, antimigraine agents, antimuscarinic agents, antineoplastic agents, antiobesity agents, antiosteoporosis agents, antiparkinsonian agents, antiproliferative agents, antiprotozoal agents, antithyroid agents, antitussive agent, anti-urinary incontinence agents, antiviral agents, anxiolytic agents, appetite suppressants, beta-blockers, cardiac inotropic agents, chemotherapeutic drugs, cognition enhancers, contraceptives, corticosteroids, Cox-2 inhibitors, diuretics, erectile dysfunction improvement agents, expectorants, gastrointestinal agents, histamine receptor antagonists, immunosuppressants, keratolytics, lipid regulating agents, leukotriene inhibitors, macrolides, muscle relaxants, neuroleptics, nutritional agents, opioid analgesics, protease inhibitors, or sedatives.

Non-limiting examples of lipophilic agents may include 7-Methoxypteridine, 7-Methylpteridine, abacavir, abafungin, abarelix, acebutolol, acenaphthene, acetaminophen, acetanilide, acetazolamide, acetohexamide, acetretin, acrivastine, adenine, adenosine, alatrofloxacin, albendazole, albuterol, alclofenac, aldesleukin, alemtuzumab, alfuzosin, alitretinoin, allobarbital, allopurinol, all-transretinoic acid (ATRA), aloxiprin, alprazolam, alprenolol, altretamine, amifostine, amiloride, aminoglutethimide, aminopyrine, amiodarone HCl, amitriptyline, amlodipine, amobarbital, amodiaquine, amoxapine, amphetamine, amphotericin, amphotericin B, ampicillin, amprenavir, amsacrine, amylnitrate, amylobarbitone, anastrozole, anrinone, anthracene, anthracyclines, aprobarbital, arsenic trioxide, asparaginase, aspirin, astemizole, atenolol, atorvastatin, atovaquone, atrazine, atropine, atropine azathioprine, auranofin, azacitidine, azapropazone, azathioprine, azintamide, azithromycin, aztreonum, baclofen, barbitone, BCG live, beclamide, beclomethasone, bendroflumethiazide, benezepril, benidipine, benorylate, benperidol, bentazepam, benzamide, benzanthracene, benzathine penicillin, benzhexol HCl, benznidazole, benzodiazepines, benzoic acid, bephenium hydroxynaphthoate, betamethasone, bevacizumab (avastin), bexarotene, bezafibrate, bicalutamide, bifonazole, biperiden, bisacodyl, bisantrene, bleomycin, bleomycin, bortezomib, brinzolamide, bromazepam, bromocriptine mesylate, bromperidol, brotizolam, budesonide, bumetanide, bupropion, busulfan, butalbital, butamben, butenafine HCl, butobarbitone, butobarbitone (butethal), butoconazole, butoconazole nitrate, butylparaben, caffeine, calcifediol, calciprotriene, calcitriol, calusterone, cambendazole, camphor, camptothecin, camptothecin analogs, candesartan, capecitabine, capsaicin, captopril, carbamazepine, carbimazole, carbofuran, carboplatin, carbromal, carimazole, carmustine, cefamandole, cefazolin, cefixime, ceftazidime, cefuroxime axetil, celecoxib, cephradine, cerivastatin, cetrizine, cetuximab, chlorambucil, chloramphenicol, chlordiazepoxide, chlormethiazole, chloroquine, chlorothiazide, chlorpheniramine, chlorproguanil HCl, chlorpromazine, chlorpropamide, chlorprothixene, chlorpyrifos, chlortetracycline, chlorthalidone, chlorzoxazone, cholecalciferol, chrysene, cilostazol, cimetidine, cinnarizine, cinoxacin, ciprofibrate, ciprofloxacin HCl, cisapride, cisplatin, citalopram, cladribine, clarithromycin, clemastine fumarate, clioquinol, clobazam, clofarabine, clofazimine, clofibrate, clomiphene citrate, clomipramine, clonazepam, clopidogrel, clotiazepam, clotrimazole, clotrimazole, cloxacillin, clozapine, cocaine, codeine, colchicine, colistin, conjugated estrogens, corticosterone, cortisone, cortisone acetate, cyclizine, cyclobarbital, cyclobenzaprine, cyclobutane-spirobarbiturate, cycloethane-spirobarbiturate, cycloheptane-spirobarbiturate, cyclohexane-spirobarbiturate, cyclopentane-spirobarbiturate, cyclophosphamide, cyclopropane-spirobarbiturate, cycloserine, cyclosporin, cyproheptadine, cyproheptadine HCl, cytarabine, cytosine, dacarbazine, dactinomycin, danazol, danthron, dantrolene sodium, dapsone, darbepoetin alfa, darodipine, daunorubicin, decoquinate, dehydroepiandrosterone, delavirdine, demeclocycline, denileukin, deoxycorticosterone, desoxymethasone, dexamethasone, dexamphetamine, dexchlorpheniramine, dexfenfluramine, dexrazoxane, dextropropoxyphene, diamorphine, diatrizoicacid, diazepam, diazoxide, dichlorophen, dichlorprop, diclofenac, dicumarol, didanosine, diflunisal, digitoxin, digoxin, dihydrocodeine, dihydroequilin, dihydroergotamine mesylate, diiodohydroxyquinoline, diltiazem HCl, diloxamide furoate, dimenhydrinate, dimorpholamine, dinitolmide, diosgenin, diphenoxylate HCl, diphenyl, dipyridamole, dirithromycin, disopyramide, disulfiram, diuron, docetaxel, domperidone, donepezil, doxazosin, doxazosin HCl, doxorubicin (neutral), doxorubicin HCl, doxycycline, dromostanolone propionate, droperidol, dyphylline, echinocandins, econazole, econazole nitrate, efavirenz, ellipticine, enalapril, enlimomab, enoximone, epinephrine, epipodophyllotoxin derivatives, epirubicin, epoetinalfa, eposartan, equilenin, equilin, ergocalciferol, ergotamine tartrate, erlotinib, erythromycin, estradiol, estramustine, estriol, estrone, ethacrynic acid, ethambutol, ethinamate, ethionamide, ethopropazine HCl, ethyl-4-aminobenzoate (benzocaine), ethylparaben, ethinylestradiol, etodolac, etomidate, etoposide, etretinate, exemestane, felbamate, felodipine, fenbendazole, fenbuconazole, fenbufen, fenchlorphos, fenclofenac, fenfluramine, fenofibrate, fenoldepam, fenoprofen calcium, fenoxycarb, fenpiclonil, fentanyl, fenticonazole, fexofenadine, filgrastim, finasteride, flecamide acetate, floxuridine, fludarabine, fluconazole, fluconazole, flucytosine, fludioxonil, fludrocortisone, fludrocortisone acetate, flufenamic acid, flunanisone, flunarizine HCl, flunisolide, flunitrazepam, fluocortolone, fluometuron, fluorene, fluorouracil, fluoxetine HCl, fluoxymesterone, flupenthixol decanoate, fluphenthixol decanoate, flurazepam, flurbiprofen, fluticasone propionate, fluvastatin, folic acid, fosenopril, fosphenytoin sodium, frovatriptan, furosemide, fulvestrant, furazolidone, gabapentin, G-BHC (Lindane), gefitinib, gemcitabine, gemfibrozil, gemtuzumab, glafenine, glibenclamide, gliclazide, glimepiride, glipizide, glutethimide, glyburide, Glyceryltrinitrate (nitroglycerin), goserelin acetate, grepafloxacin, griseofulvin, guaifenesin, guanabenz acetate, guanine, halofantrine HCl, haloperidol, hydrochlorothiazide, heptabarbital, heroin, hesperetin, hexachlorobenzene, hexethal, histrelin acetate, hydrocortisone, hydroflumethiazide, hydroxyurea, hyoscyamine, hypoxanthine, ibritumomab, ibuprofen, idarubicin, idobutal, ifosfamide, ihydroequilenin, imatinib mesylate, imipenem, indapamide, indinavir, indomethacin, indoprofen, interferon alfa-2a, interferon alfa-2b, iodamide, iopanoic acid, iprodione, irbesartan, irinotecan, isavuconazole, isocarboxazid, isoconazole, isoguanine, isoniazid, isopropylbarbiturate, isoproturon, isosorbide dinitrate, isosorbide mononitrate, isradipine, itraconazole, itraconazole, itraconazole (Itra), ivermectin, ketoconazole, ketoprofen, ketorolac, khellin, labetalol, lamivudine, lamotrigine, lanatoside C, lanosprazole, L-DOPA, leflunomide, lenalidomide, letrozole, leucovorin, leuprolide acetate, levamisole, levofloxacin, lidocaine, linuron, lisinopril, lomefloxacin, lomustine, loperamide, loratadine, lorazepam, lorefloxacin, lormetazepam, losartan mesylate, lovastatin, lysuride maleate, Maprotiline HCl, mazindol, mebendazole, Meclizine HCl, meclofenamic acid, medazepam, medigoxin, medroxyprogesterone acetate, mefenamic acid, Mefloquine HCl, megestrol acetate, melphalan, mepenzolate bromide, meprobamate, meptazinol, mercaptopurine, mesalazine, mesna, mesoridazine, mestranol, methadone, methaqualone, methocarbamol, methoin, methotrexate, methoxsalen, methsuximide, methyclothiazide, methylphenidate, methylphenobarbitone, methyl-p-hydroxybenzoate, methylprednisolone, methyltestosterone, methyprylon, methysergide maleate, metoclopramide, metolazone, metoprolol, metronidazole, Mianserin HCl, miconazole, midazolam, mifepristone, miglitol, minocycline, minoxidil, mitomycin C, mitotane, mitoxantrone, mofetilmycophenolate, molindone, montelukast, morphine, Moxifloxacin HCl, nabumetone, nadolol, nalbuphine, nalidixic acid, nandrolone, naphthacene, naphthalene, naproxen, naratriptan HCl, natamycin, nelarabine, nelfinavir, nevirapine, nicardipine HCl, nicotinamide, nicotinic acid, nicoumalone, nifedipine, nilutamide, nimodipine, nimorazole, nisoldipine, nitrazepam, nitrofurantoin, nitrofurazone, nizatidine, nofetumomab, norethisterone, norfloxacin, norgestrel, nortriptyline HCl, nystatin, oestradiol, ofloxacin, olanzapine, omeprazole, omoconazole, ondansetron HCl, oprelvekin, ornidazole, oxaliplatin, oxamniquine, oxantelembonate, oxaprozin, oxatomide, oxazepam, oxcarbazepine, oxfendazole, oxiconazole, oxprenolol, oxyphenbutazone, oxyphencyclimine HCl, paclitaxel, palifermin, pamidronate, p-aminosalicylic acid, pantoprazole, paramethadione, paroxetine HCl, pegademase, pegaspargase, pegfilgrastim, pemetrexeddi sodium, penicillamine, pentaerythritol tetranitrate, pentazocin, pentazocine, pentobarbital, pentobarbitone, pentostatin, pentoxifylline, perphenazine, perphenazine pimozide, perylene, phenacemide, phenacetin, phenanthrene, phenindione, phenobarbital, phenolbarbitone, phenolphthalein, phenoxybenzamine, phenoxybenzamine HCl, phenoxymethyl penicillin, phensuximide, phenylbutazone, phenytoin, pindolol, pioglitazone, pipobroman, piroxicam, pizotifen maleate, platinum compounds, plicamycin, polyenes, polymyxin B, porfimersodium, posaconazole (Posa), pramipexole, prasterone, pravastatin, praziquantel, prazosin, prazosin HCl, prednisolone, prednisone, primidone, probarbital, probenecid, probucol, procarbazine, prochlorperazine, progesterone, proguanil HCl, promethazine, propofol, propoxur, propranolol, propylparaben, propylthiouracil, prostaglandin, pseudoephedrine, pteridine-2-methyl-thiol, pteridine-2-thiol, pteridine-4-methyl-thiol, pteridine-4-thiol, pteridine-7-methyl-thiol, pteridine-7-thiol, pyrantelembonate, pyrazinamide, pyrene, pyridostigmine, pyrimethamine, quetiapine, quinacrine, quinapril, quinidine, quinidine sulfate, quinine, quininesulfate, rabeprazole sodium, ranitidine HCl, rasburicase, ravuconazole, repaglinide, reposal, reserpine, retinoids, rifabutine, rifampicin, rifapentine, rimexolone, risperidone, ritonavir, rituximab, rizatriptan benzoate, rofecoxib, ropinirole HCl, rosiglitazone, saccharin, salbutamol, salicylamide, salicylic acid, saquinavir, sargramostim, secbutabarbital, secobarbital, sertaconazole, sertindole, sertraline HCl, simvastatin, sirolimus, sorafenib, sparfloxacin, spiramycin, spironolactone, stanolone, stanozolol, stavudine, stilbestrol, streptozocin, strychnine, sulconazole, sulconazole nitrate, sulfacetamide, sulfadiazine, sulfamerazine, sulfamethazine, sulfamethoxazole, sulfanilamide, sulfathiazole, sulindac, sulphabenzamide, sulphacetamide, sulphadiazine, sulphadoxine, sulphafurazole, sulphamerazine, sulpha-methoxazole, sulphapyridine, sulphasalazine, sulphinpyrazone, sulpiride, sulthiame, sumatriptan succinate, sunitinib maleate, tacrine, tacrolimus, talbutal, tamoxifen citrate, tamulosin, targretin, taxanes, tazarotene, telmisartan, temazepam, temozolomide, teniposide, tenoxicam, terazosin, terazosin HCl, terbinafine HCl, terbutaline sulfate, terconazole, terfenadine, testolactone, testosterone, tetracycline, tetrahydrocannabinol, tetroxoprim, thalidomide, thebaine, theobromine, theophylline, thiabendazole, thiamphenicol, thioguanine, thioridazine, thiotepa, thotoin, thymine, tiagabine HCl, tibolone, ticlopidine, tinidazole, tioconazole, tirofiban, tizanidine HCl, tolazamide, tolbutamide, tolcapone, topiramate, topotecan, toremifene, tositumomab, tramadol, trastuzumab, trazodone HCl, tretinoin, triamcinolone, triamterene, triazolam, triazoles, triflupromazine, trimethoprim, trimipramine maleate, triphenylene, troglitazone, tromethamine, tropicamide, trovafloxacin, tybamate, ubidecarenone (coenzyme Q10), undecenoic acid, uracil, uracil mustard, uric acid, valproic acid, valrubicin, valsartan, vancomycin, venlafaxine HCl, vigabatrin, vinbarbital, vinblastine, vincristine, vinorelbine, voriconazole, xanthine, zafirlukast, zidovudine, zileuton, zoledronate, zoledronic acid, zolmitriptan, zolpidem, and zopiclone.

In particular aspects, the agents may be busulfan, taxane or other anticancer agents; or alternatively, itraconazole (Itra) and posaconazole (Posa) or other members of the general class of azole compounds. Exemplary antifungal azoles include a) imidazoles such as miconazole, ketoconazole, clotrimazole, econazole, omoconazole, bifonazole, butoconazole, fenticonazole, isoconazole, oxiconazole, sertaconazole, sulconazole and tioconazole, b) triazoles such as fluconazole, itraconazole, isavuconazole, ravuconazole, Posaconazole, voriconazole, terconazole and c) thiazoles such as abafungin. Other drugs that can be solubilized with this approach include, but are not limited to, hyperthyroid drugs such as carimazole, anticancer agents like cytotoxic agents such as epipodophyllotoxin derivatives, taxanes, bleomycin, anthracyclines, as well as platinum compounds and camptothecin analogs. They may also include other antifungal antibiotics, such as poorly water-soluble echinocandins, polyenes (e.g., Amphotericin B and Natamycin) as well as antibacterial agents (e.g., polymyxin B and colistin), and anti-viral drugs. The agents may also include a psychiatric agent such as an antipsychotic, anti-depressive agent, or analgesic and/or tranquilizing agents such as benzodiazepines. The agents may also include a consciousness level-altering agent or an anesthetic agent, such as propofol. In a broader aspect, the present invention may provide methods to safely solubilize and administer many poorly water-soluble, pharmacologically active agents.

As an additional advantage, any compositions described herein may obviate the need of a surfactant, thus a polyethylene glycol (PEG) fatty acid ester surfactant (but not PEG itself) or other surfactants may not be used in certain aspects. In other aspects, a surfactant known in the art may be used.

An amphiphilic liquid polymeric solvent may be used to provide/simulate a non-polar/lipophilic milieu. The amphiphilic liquid polymeric solvent may be of a single polymer type, or have at least two polymer types in some aspects. For example, the amphiphilic liquid polymeric solvent may be a PEG solvent such as PEG-100, -200, -300, -400, -800, -1000, and the like. A particular example may be PEG-400. The PEG used herein may exclude any PEG that is in a solid state at a selected temperature such as room temperature, body temperature or a temperature of at least, about or at most 5, 10, 15, 20, 21, 22, 23, 24, 25, 30, 31, 32, 33, 34, 35, 36, 37, 38, 39, 40, 45, 50, 55, 60, 65, 70, 75, 80° C., or any range or value derivable therein, such as PEG with a high molecular weight (average molecular weight of at least or more than 1600, 2000, 3000, 4000, 5000, 6000, 10,000 dalton or any intermediate ranges). For example, the liquid solvent may be PEG-800 or PEG-1000 as they are liquid at body temperature.

To facilitate solubilization of the lipophilic agents, the composition involving the lipophilic agents may further comprise a protonating agent to facilitate protonation of the reactive groups in lipophilic agents. For example, the protonating agent is an acid, alcohol or acidified alcohol (such as benzyl alcohol, and/or acidified ethanol). Non-limiting examples of acid include HCl, citric acid, acetic acid or glutamic acid or other inorganic acids or organic acids known in the art. The composition may have an acidic pH, such as a pH value or range derived from a pH of from about 0.5, 1, 2, 3, 4, 5, 6, 6.5, and 6.9, preferably in a range from about 1 to about 6.

The invention also includes a method of preparing a non-aqueous, homogeneous solution described above, comprising the steps of: obtaining a first non-aqueous, homogeneous solution comprising a lipophilic pharmaceutical agent, an amphiphilic liquid polymeric solvent and a volatile organic solvent, and removing the volatile organic solvent from the first solution to form a second non-aqueous, homogeneous solution as described herein ("stock solution" or may be used in final clinical use). The volatile organic solvent may be used to facilitate binding of the lipophilic agents to the polymeric solvent via electrostatic interactions. Non-limiting examples may include acetone, chloroform, aliphatic hydrocarbons, ethyl acetate, glycol ethers, diethylether, or ethanol. A particular example may be acetone. The method may be defined as a method for preparing an aqueous, homogeneous, pharmaceutically-acceptable parenteral formulation as it may further comprise diluting the second solution described above with a desired aqueous diluent to produce a final clinical use-formulation.

In further aspects, the volume or weight ratio of the volatile organic solvent to the amphiphilic liquid polymeric solvent may be from about 100:1 to 1:100, or particularly, 1:1, 1:2, 1:3, 1:5, 1:10, 1:20, 1:30, 1:40, 1:50, 1:60, 1:70, 1:80, 1:90 or any range derivable therein. To facilitate the interaction between the reactive groups in the lipophilic agents and amphiphilic solvents, the volatile organic solvent or the desired aqueous diluent may be acidified. The method may further comprise storing any of the compositions for at least 1, 2, 3, 4, 5, 6, 7 days, 1, 2, 3, 4, 5, 6, 7, 8, 9, 10, 12 weeks, 4, 5, 6, 7, 8, 9, 10, 11, 12 months, 2, 3, 4, 5, 6, 7, 8, 9, 10 years or any value or range derivable therein.

Any of the method steps, such as removal of the volatile organic solvents or storage of any compositions, may be performed at a temperature of at least, about or at most 5, 10, 15, 20, 25, 30, 40, 45, 50, 55, 60, 65, 70, 75, 80° C., or any range or value derivable therein. In a particular aspect, the temperature may be room temperature. The removing method may include any method that is known to remove a volatile organic solvent, such as evaporation, more particularly, vacuum-assisted evaporation. The removal may be extended to extract the protonating agent.

After removal of the volatile organic solvent, the composition may be stable for at least 1, 2, 3, 4, 5, 6, 7 days, 2, 3, 4, 5, 6, 7, 8, 9, 10, 12 weeks, 4, 5, 6, 7, 8, 9, 10, 11, 12 months, 2, 3, 4, 5, 6, 7, 8, 9, 10 years or any value or range derivable therein. The composition may be further diluted with a desired aqueous diluent to facilitate its clinical administration. For example, the aqueous diluent may be an infusion fluid selected from the group consisting of normal saline, dextrose in water, and a lipid-based infusion emulsion fluid. In particular, the aqueous infusion fluid may be 0.9% sodium chloride (NS), or 5% or 10% dextrose in water (D5W and D10W, respectively), or an aqueous lipid emulsion such as Intralipid™, or Liposyn™. In a further aspect, such an aqueous diluent may be modified by the addition of a protonating agent or with a small amount of PEG as described above. Such modification of the diluent may be preferred if the protonating agent is removed from the stock solution. The resulting stable, final use formulation may contain the dissolved pharmaceutical agent that, dissolved at room temperature (RT), remains stable for an extended time to allow convenient handling and administration to the patients.

In further aspects, the invention includes a method of preparing a water-insoluble/lipophilic pharmaceutically active agent for parenteral use comprising the steps of: solubilizing the pharmaceutically active agent in a(n) (volatile) organic solvent, mixing it with a second, non-volatile hydrophobic agent. The second solvent may preferably have amphiphilic properties, such as PEG. The method may further comprise evaporating off the more volatile organic solvent component under vacuum such that a local electrostatic attraction arises that binds the pharmaceutically active agent to the secondary amphiphilic solvent. Physical precipitation of the pharmaceutically active agent may thereby be prevented, thus producing a stock formulation. In a further aspect, the method may comprise mixing the dissolved pharmaceutically active agent/amphiphilic solvent (e.g., PEG) complex with a final aqueous diluent to provide a clinical use-formulation that can be administered parenterally. For example, the organic solvent is acetone or chloroform, or diethylether, with or without addition of a small amount of an acid to facilitate protonation of the pharmaceutically active agent to increase the electrostatic attraction to the secondary solvent. Preferably the secondary amphiphilic solvent is a polymer such as PEG. The pharmaceutically active agent may be a bifunctional DNA-alkylating agent such as busulfan (Bu) or, alternatively, it can be an antimicrobial agent such as an azole compound used to treat fungal or parasitic infections, or a hypnotic or sedative agent used in psychiatric or anesthetic settings, or alternatively it can be an agent used for symptom control such as an anesthetic or a consciousness-level altering agent such as a general anesthetic. Further, to increase the stable electrostatic attraction between the pharmaceutically active agent and the amphiphilic solvent such as PEG, the vacuum-extraction may be significantly extended to remove excess (free) acid from the drug/PEG-complex. Finally, the method may comprise the step of mixing the stock formulation with a secondary diluent, such as an aqueous infusion fluid, to allow the administration of the pharmaceutically active agent in a domestic animal or more preferably, in a human.

The invention may also include a method for treating a subject having a disease or condition sensitive or responsive to an lipophilic pharmaceutical agent, comprising: parenterally administering to the subject a therapeutically effective dissolved amount of a composition comprising a solution or a formulation described above, wherein solution or formulation has the lipophilic pharmaceutical agent to which that the disease or condition is sensitive or responsive.

In a particular aspect, the invention also includes a method for treating a disease sensitive or responsive to Bu comprising: parenterally administering a therapeutically effective amount of a Bu composition to the patient. The Bu composition may be prepared by dissolving Bu in a first solvent comprising a volatile organic solvent, preferably acetone, then mixing the solution with a second amphiphilic solvent, preferably PEG, subsequently evaporating the first organic solvent under vacuum to create a stock-formulation of Bu in PEG, and optionally diluting with a secondary aqueous diluent, such as an aqueous infusion fluid.

Still another embodiment of the invention is directed to a method for parenterally administering Bu to a patient comprising: providing Bu in an organic, volatile hydrophobic solvent, subsequently mixed with a second amphiphilic, non-volatile solvent; evaporating the first hydrophobic solvent to produce a Bu stock formulation that can be either directly administered to the patient, or mixing the stock formulation with a secondary aqueous diluent to form an infusion fluid; and administering the infusion fluid to a patient. For example, the first, volatile organic solvent is acetone, and the secondary amphiphilic solvent is PEG400.

The routes of administration may include, but are not limited to, administration intravascularly, intracavitarily, intrathecally, subcutaneously, intramuscularly, or topically. The subject may be a mammal, particularly a domestic animal or a human.

In certain aspects, the subject has a cancer or a need for conditioning the subject to perform a bone marrow transplantation or a hematopoietic progenitor cell transplantation and the lipophilic pharmaceutical agent is busulfan. In other aspects, the subject has a fungal, yeast or mold disease and the lipophilic pharmaceutical agent is an azole agent. In further aspects, the subject has a psychiatric ailment or a need for symptomatic control and the lipophilic pharmaceutical agent is a psychiatric agent, such as an antipsychotic, anti-depressive agent, or an analgesic agent. The subject has a need to alter the level of consciousness or to induce general anesthesia or conscious sedation and the lipophilic pharmaceutical agent is a consciousness level-altering or an anesthetic agent such as propofol.

Other objects and advantages of the invention are set forth in part in the description which follows and, in part, will be obvious from this description, or may be learned from the practice of the invention.

BRIEF DESCRIPTION OF THE DRAWINGS

The following figures form part of the present specification and are included to further demonstrate certain aspects of the invention. The invention may be better understood by reference to one or more of these drawings in combination with the detailed description of specific embodiments presented herein.

FIGS. 1A-B. (A) A graph showing the stability of busulfan at room temperature in the final use-formulation of Bu/VE-acetone/PEG (i.e., prototype stock solvent vehicle) containing Bu at an approximate concentration of 5 mg/mL after vacuum extraction of acetone. (B) The stock formulation is diluted with D5W to 1 mg/mL (top), and to 0.5 mg/mL (lower). The X-axis represents the time in hours, and the Y-axis represents the measured concentration in mg/mL.

FIG. 3. Chromatograms obtained from the HPLC assay in the stability studies. The inventors used the Waters Nova-Pak C18 column, (4-µm bead size; 150 mm×3.9 mm). The injected sample volume was 30 µL. The HPLC conditions are described in Example 1.

FIGS. 13A-C. Chromatograms of blank plasma (upper panel), Posa after spiking of human plasma (middle panel), as well as Posa in a sample obtained 2 hours after IV injection of 5 mg/kg of Posa in mice (lower panel) as described under the experimental protocol in the text.

DETAILED DESCRIPTION OF THE PREFERRED EMBODIMENTS

Figure 2:
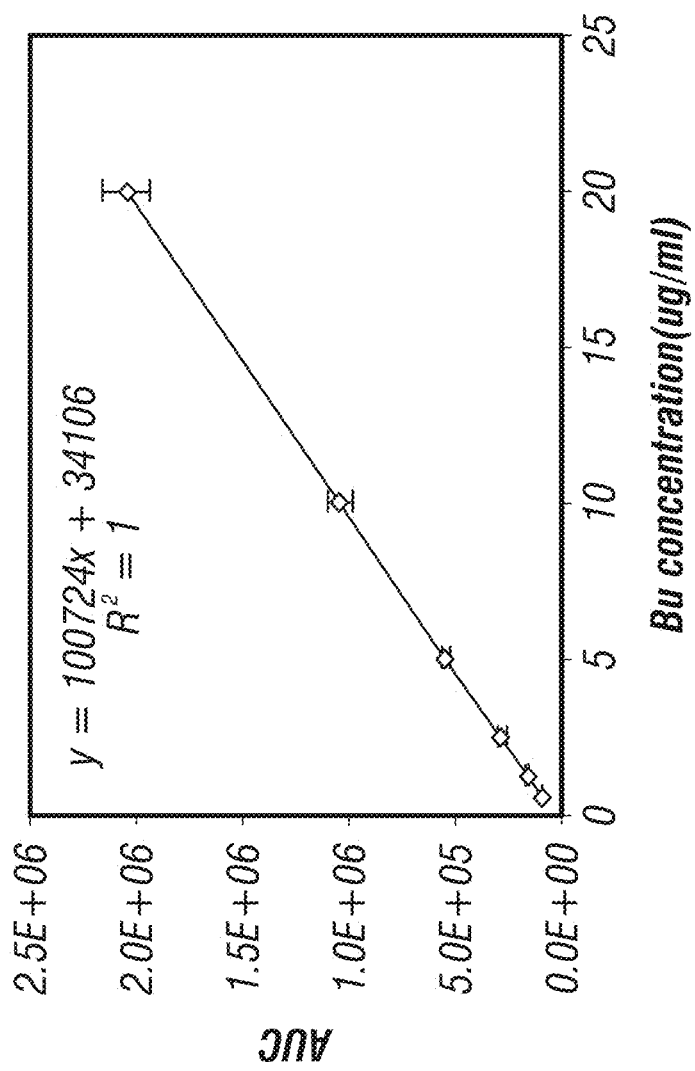
FIG. 2. Standard curve of busulfan concentration vs. area under the curve (AUC; area under the curve, term used to denote the actual measured area of a peak in a chromatogram, and also for the area under the plasma concentration vs. time curve over several hours after administration of a drug to an animal or human being) for the high-pressure liquid chromatography (HPLC) assay used in the in vitro stability and in vivo pharmacology studies. The X-axis shows concentration in µg/mL, and the Y-axis shows the AUC. An analogous standard curve was prepared for the pharmacology studies.

Certain aspects of the present invention are directed to novel formulations containing lipophilic agents such as busulfan or anti-infectious agents, preferably belonging to the general class of compounds described as azoles, that may be administered parenterally. An aspect of the invention provides for a solubilized lipophilic agent in complex, pharmaceutically acceptable vehicles such that the dissolved agent remains physically and chemically stable for prolonged time. The invention allows for parenteral administration of the drug in doses necessary to obtain significant pharmaceutical effects such as cytotoxic and immunosuppressive effects in subjects like humans and domestic animals without undue toxicity from any component of the used solvent vehicle. Exemplary embodiments of the invention allow for the parenteral, e.g. intravascular or intrathecal or intracavitary administration of solubilized agents to increase the safety of clinical drug administration. As a result, an improved control of diseases that are sensitive to this agent such as malignant and autoimmune diseases may be achieved.

In certain aspects, there may be provided a method of preparing (a) hard-to-solubilize, "water-insoluble" or lipophilic pharmaceutically active agent(s) for parenteral use. Suitable lipophilic pharmaceutically active agents may include busulfan, azole agents such as Itra and Posa, or any lipophilic agents known in the art, as exemplified herein. Certain aspects of the present invention, which may be based on the principle of cosolvency but without wishing to be bound by theory, use a novel series of composite diluent vehicles to solubilize lipophilic agents, such as busulfan, itraconazole (Itra) and posaconazole (Posa), without affecting their pharmaceutical activity while improving aqueous solubility and stability. Further, the preferred solvents are, in the proposed concentrations and total doses used, nontoxic and safe for human and mammalians, most preferably in humans and domestic animals.

The methods may first comprise dissolving the pharmaceutically active agent in a primary volatile hydrophobic solvent followed by admixture of a second non-volatile amphiphilic solvent. The methods may further comprise removing (e.g., by vacuum extraction) the primary volatile solvent to provide a clinically acceptable stock formulation comprising the agent and the amphiphilic solvent. The methods may optionally comprise diluting this stock formulation with an aqueous solvent, such as an infusion fluid like D5W or D10W, or NS. Preferably, the primary volatile solvent is acetone and the second amphiphilic solvent is PEG-400.

In addition to acetone and PEG, other organic solvents may be used to form the solvent vehicle without departing from the spirit and scope of the invention. A volatile solvent can be a single solvent or a mixture of solvents that are volatile, including water and solvents that are more volatile than water. Non-limiting examples of volatile solvents that can be used in the present invention include acetone, chloroform, aliphatic hydrocarbons, ethyl acetate, glycol ethers, diethyl-ether, iso-amyl acetate, denatured alcohol, methanol, ethanol, isopropyl alcohol, propanol, C4-C6 hydrocarbons, butane, isobutene, pentane, hexane, acetone, chlorobutanol, ethyl acetate, fluro-chloro-hydrocarbons, turpentine, methyl ethyl ketone, methyl ether, hydrofluorocarbons, ethyl ether, 1,1,1,2 tetrafluorethane, 1,1,1,2,3,3,3-heptafluoropropane, 1,1,1,3,3,3 hexafluoropropane, and combinations thereof. The volatile solvent may be substantially removed by evaporation to form a homogenous solution comprising the agent and the amphiphilic liquid solvent essentially free of the volatile solvent. The use of the term "substantially" when referring to the removal of the volatile solvents means that a majority of the volatile solvent(s) which was/were included in the initial formulation has/have been removed.

Non-volatile amphiphilic solvents may be one or more solvents that are less volatile than water. Similarly, a non-volatile solvent is defined as a solvent that is less volatile than water. Preferably, the non-volatile solvent may contain substances that are liquid at room temperatures. After evaporation of the volatile solvent, most of the non-volatile solvent system should remain in a homogenous solution comprising the lipophilic agent.

For some hydrophobic agents, in particular drugs that contain uncharged reactive functional (amino) groups, the electrostatic attraction between the amphiphilic solvent such as PEG and the pharmaceutically active agent may be augmented by adding a protonating agent such as an organic acid or HCl, or an alcohol such as benzylalcohol, to the first organic solvent prior to mixing the solubilized drug with PEG. After removal of the first organic solvent the final use-formulation is arrived to by the admixture of a clinically acceptable aqueous infusion fluid. If the latter preferred step of using a protonating agent (acid) to increase the electrostatic attraction between the pharmaceutically active agent and PEG then a prolonged vacuum-extraction may be utilized to assure extraction not only of the first organic solvent but also of remaining free acid. Said removal of excess free acid will allow for extending the shelf-life of the pharmaceutically active agent when bound to the amphiphilic agent such as PEG. If the latter approach is utilized then it is preferred that the reconstitution prior to in vivo administration be done using acidified D5W or D10W as the final diluent to maintain optimal electrostatic attraction between the pharmaceutically active agent and PEG to prevent precipitation of the agent prior to parenteral administration.

As shown in the Examples, Busulfan (Bu) and two prototype antifungal azole agents were successfully formulated for parenteral administration, utilizing a novel solvent system approach. For example, the lipophilic drugs may be solubilized in a volatile primary solvent vehicle mixed with (a) secondary non-volatile, non-toxic amphiphilic polymer solvent(s). In a particular embodiment, the primary solvent may be a volatile organic solvent such as acetone, or chloroform. Subsequently the first volatile solvent may be removed, for example, by vacuum extraction, but the drugs may remain solubilized in a solution of the polymer solvent. An optional diluent, e.g., a clinically acceptable infusion fluid such as D5W, may allow for dilution of the vacuum-extracted solution into clinical use-formulations that are stable for many (more than 12) hours at RT. As an added benefit of the new formulation(s) should also be mentioned that when diluted in the final use-formulation, the current composition allows lipophilic drugs to be administered with improved solubility and stability in the final use-formulation. For example, Bu could be administered at a higher concentration of at least 1 mg/mL as compared with the currently used DMA-Bu at only 0.5 mg/mL and it has a more extended stability at RT (at least about 15 hours vs. 6 hours for DMA-Bu), both of which contribute to improved patient safety and convenience in routine pharmacy drug handling.

In a particular embodiment of the invention, Bu may be dissolved using a volatile solvent such as acetone, and then combined with an amphiphilic solvent such as PEG as the composite vehicle or solvent system. If this solubilized Bu/acetone/PEG mixture is mixed with water, the Bu remains in solution without precipitation for several hours. However, due to the toxicity of acetone to mammalian tissues (Dwivedi, 2002; VICH Steering Committee, 2010; The Food and Drug Administration, 2010; The Office of Environmental Health Hazard Assessment, 2010), the acetone may be preferably removed under vacuum, such that the pharmaceutically active agent may become electrostatically attracted/bound to PEG in an non-aqueous solution, a procedure that has not been previously documented. The novel exemplary Bu stock formulations (i.e. prior to the addition of the secondary/final diluent) may be stable for many weeks at room temperature, are simple to handle, and provide for reliable and easily controlled, consistent dose administration. Prior to administration such as parenteral administration, the non-aqueous stock solution may be then (optionally) diluted in a secondary diluent such as a readily available infusion fluid, e.g., 5-10% dextrose-in-water (D5W and D10W, respectively). The non-aqueous stock solution (Bu-PEG variant compositions) may be miscible in secondary/final aqueous diluents, or routinely available aqueous infusion fluids, e.g. 0.9% sodium chloride (normal saline, NS), and D5W, as well as a stock solution (such as D5W) with 10-25% (v/v) of an amphiphilic polymer (e.g., PEG). Such terminal diluents/infusion fluids are typical examples of vehicles used to solubilize pharmacologically active agents for human administration, alone or in combination with other drugs. The admixture of a small amount of an amphiphilic polymer to the aqueous infusion fluid will further stabilize the lipophilic compound when prepared for parenteral infusion.

Busulfan as an orally administered anticancer agent has previously been extensively investigated in humans, and in the last decade these data have been supplemented with results obtained with the DMA-based parenteral formulation; Busulfan has well documented cytotoxic, myelosuppressive, as well as immunosuppressive properties in both clinical and experimental settings. Unfortunately, Bu is a poorly water-soluble DNA-alkylating agent with exceedingly low solubility in physiologically acceptable aqueous solvents that would be compatible with human parenteral administration. Prior to the present invention, the only available administration forms have been an oral preparation and the DMA-based parenteral formulation. A parenteral formulation of Bu that is free from the risk of adverse events related to the high DMA-content has not been available. Such a parenteral Bu formulation would be useful to evaluate Bu by itself and in combination with other drugs as part of individualized therapy for systemic malignant and autoimmune disorders as well as when profound long-term immunosuppression is desirable, for instance as required in preparation for (allogeneic) hematopoietic stem cell transplantation (HSCT) for both malignant and non-malignant, e.g. most commonly inborn/genetic disorders. A parenteral formulation may need complete dose assurance and guaranteed 100% bioavailability.

As discussed in the Examples below, novel vehicles have been discovered which achieve the stable, pharmaceutically acceptable solubilization of Bu, thereby making it safe to administer this drug intravascularly without the undue toxicity of DMA, something previously unattainable. The data in the Examples demonstrate that the novel Bu formulations may be used for parenteral treatment of malignant and advanced autoimmune disorders, as well as in conditioning therapy for HSCT.

Busulfan is very hydrophobic/lipophilic, and for practical purpose insoluble in water and PEG. The use of a volatile hydrophobic solvent such as acetone dissolves it and through the addition of an amphiphilic liquid solvent such as PEG with subsequent evacuation of the volatile solvent the Bu may be contemplated to be electrostatically stabilized/bound to the amphiphilic liquid solvent such as PEG, such that it tolerates further dilution in an aqueous diluent or blood plasma without imminent physical precipitation or chemical degradation. The stability of the new formulation may permit combined handling and infusion times in excess of 12 hours without significant loss of drug activity.

As shown in the Examples, the described acetone-PEG-based vehicles were successfully used to dissolve Bu at concentrations ranging from 0.1 to at least 10 mg/mL. This range is broad enough to cover the administration of doses necessary to yield cytotoxic concentrations in vivo when treating malignancies sensitive to this drug. Similarly, this range permits administration of the dose(s) necessary to achieve effective immunosuppression in patients with autoimmune disorders and those undergoing pre-HSCT conditioning therapy.

The data obtained in the Examples further demonstrate that stable Bu formulation(s) may allow parenteral treatment of systemic malignant and autoimmune diseases. This preparation may consistently provide 100% drug bioavailability, and it may allow circumvention of the hepatic first-pass extraction. After a brief IV injection, the plasma Bu concentrations clearly reach, and for extended time remain in, the cytotoxic range as established by the in vitro studies of its cytotoxic activity against human malignant cell lines, and these concentrations also compare favorably with several investigations that utilized either oral Bu or the DMA-Bu formulation (Slattery et al., 1997; Dix et al., 1996; Hassan et al., 2000; Hassan et al., 1989; Russell et al., 2002; De Lima et al., 2004; Madden et al., 2007; Andersson et al., 2008).

In further embodiments, azole compounded may be used in the novel formulations and methods for improved aqueous solubility and stability, such as itraconazole (Itra) and posaconazole (Posa). The antifungal azole agents itraconazole (Itra) and posaconazole (Posa), that belong to the general class of agents commonly referred to as tri-azole compounds, have earned an impressive reputation for their efficacy against both yeast and various molds. The introduction of such azoles in clinical medicine has greatly improved the control of systemic fungal infections in both HIV- and non-HIV-infected immunocompromised individuals. These compounds are active against a variety of fungal infections such as aspergillosis, blastomycosis, histoplasmosis, and candidiasis, as well as fungal infections localized to the toenails and fingernails (onychomycosis), and to infections of the skin and reproductive tract (primarily referred to as "vaginal yeast infections"). They are also used for empirically and preemptively treating immunocompromised patients with fever and low white blood cell counts who are likely to develop a fungal infection after radio- or chemotherapy for malignant disease. The usual recommended dose varies between the different members of the azole family in a single dose or two to three divided daily doses. Capsules should be taken with a full meal because lipid-containing food improves absorption.

Itra, as a representative example of orally administered antifungal agent(s)/(tri)-azoles, has previously been extensively investigated in humans and domestic animals (Baddley et al., 2009; Campo et al., 2010; Chen et al., 2010; Dutkiewicz and Hage, 2010; Evans, 2010; Glockner and Karthaus, 2010; Hicheri et al., 2010; Hsu et al., 2010; Ito et al., 2010; Jang et al., 2010; Kim et al., 2010; Lehrnbecher et al., 2010; Lewis and Kontoyiannis, 2009; Lortholary et al., 2010; Pappas et al., 2010; Person et al., 2010; Singh et al., 2006; Tones et al., 2005; Ullmann et al., 2007; Vehreschild et al., 2010; Walsh et al., 2010; Wingard et al., 2010; Winston et al., 2010; Greer, 2007; Carrillo-Munoz et al., 2005; Dodds-Ashley and Alexander, 2005; Groll and Walsh, 2006; Notheis et al., 2006; Courtney et al., 2003; Zhou et al., 1998; Boothe et al., 1997; Davis et al., 2005; Willems et al., 2001); the(se) drug(s) has (have) well documented anti-infectious properties in both clinical and experimental settings. However, prior to the present invention, (an) acceptable parenteral formulation(s) of solubilized Itra, Posa and other members of this diverse family of chemicals either referred to as tri-azoles, or simply azole compounds, have not been consistently available, but parenteral administration has been accomplished by allowing the use of microcrystalline suspensions of these azoles. The variable and somewhat unreliable stability of such formulations have given varying, unpredictable results. Thus, voriconazole is commercially available as such a formulation, while Itra was voluntarily withdrawn from the U.S. market by its manufacturer, and Posa remains unavailable despite repeated attempts to provide a clinically useful parenteral formulation.

Truly solubilized, parenteral formulations of Itra and Posa would be useful as treatment of systemic infectious disorders in immunocompromised patients who for a multitude of reasons are unable to consistently take oral preparations, such as e.g. commonly experienced after (intensive) conventional chemotherapy for acute leukemia and other malignant diseases, and after (allogeneic) hematopoietic stem cell transplantation, where in the early post-transplant phase drug-related nausea, vomiting and diarrhea as well as administration of concomitant medications may impair oral drug bioavailability while later on the occurrence of intestinal graft-vs-host disease and its therapy may result in a similar situation. In such patients parenteral drug administration gives complete control of systemic drug delivery/pharmacokinetics of the delivered agent with an accuracy simply not attainable with an oral formulation (Benet and Sheiner, 1985). Unfortunately, Itra is a poorly water-soluble agent with exceedingly low solubility in physiologically acceptable aqueous solvents/infusion fluids that would be compatible with human administration. Prior to the invention, the only currently available administration form is oral preparations (capsules and an oral suspension), while a previously available microcrystalline suspension for IV use was withdrawn by its supplier shortly after FDA-approval due to its unpredictable pharmaceutical behavior. To the inventors' knowledge a truly solubilized form of Itra has never been available, but only a colloidal, or microcrystalline suspension in hydroxypropyl-beta-cyclodextrin (Willems et al., 2001).

Figure 9A:
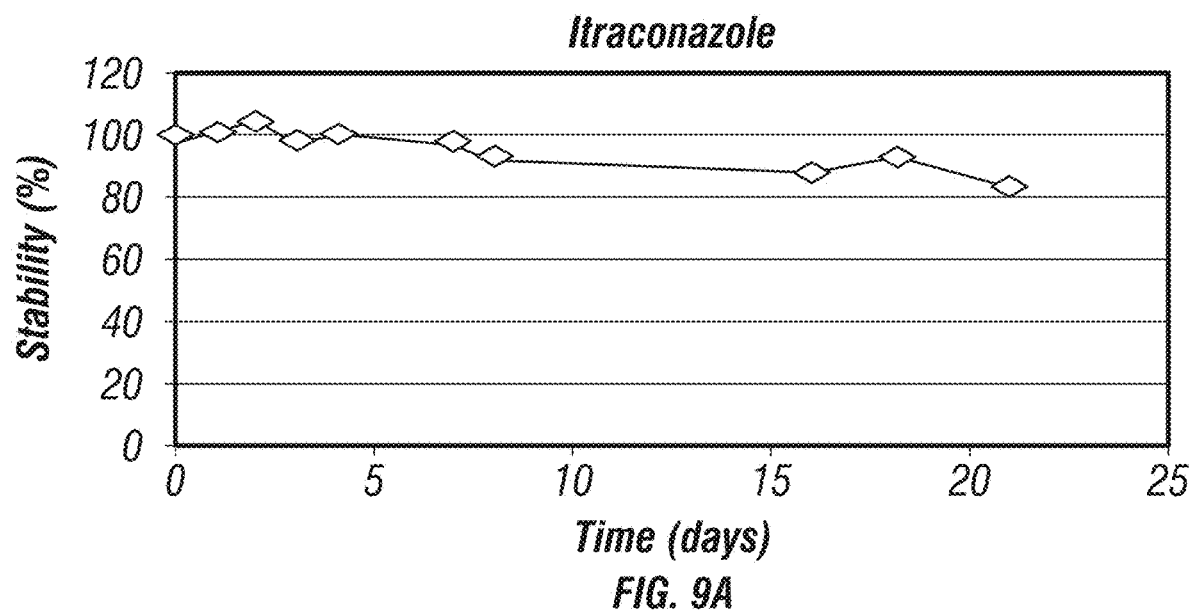
FIGS. 9A-B. Stability of (A) Itra and (B) Posa in a variant formulation over a 3-week period at RT.
Figure 9B:
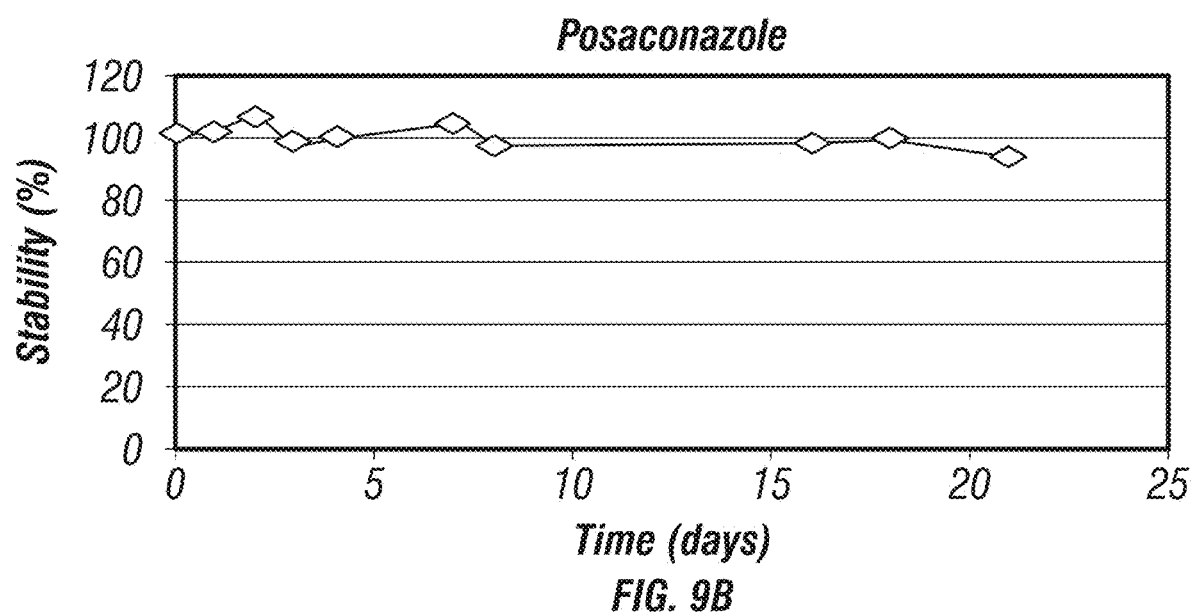
Figure 10A:
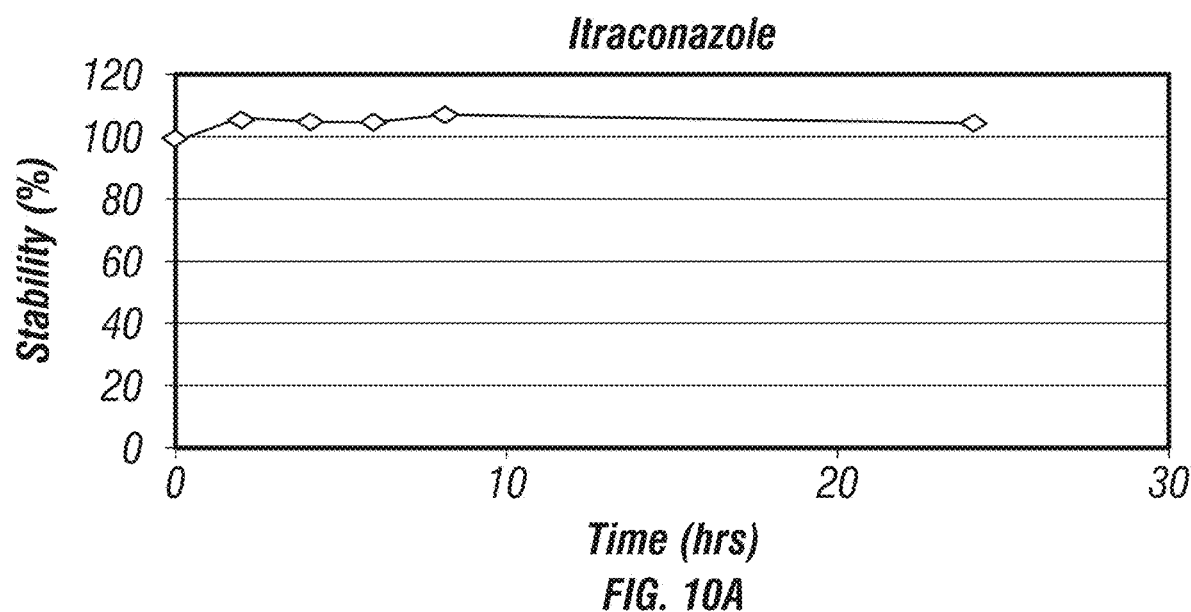
FIGS. 10A-B. Stability of (A) Itra and (B) Posa in the final use-formulations diluted in D5W.
Figure 10B:
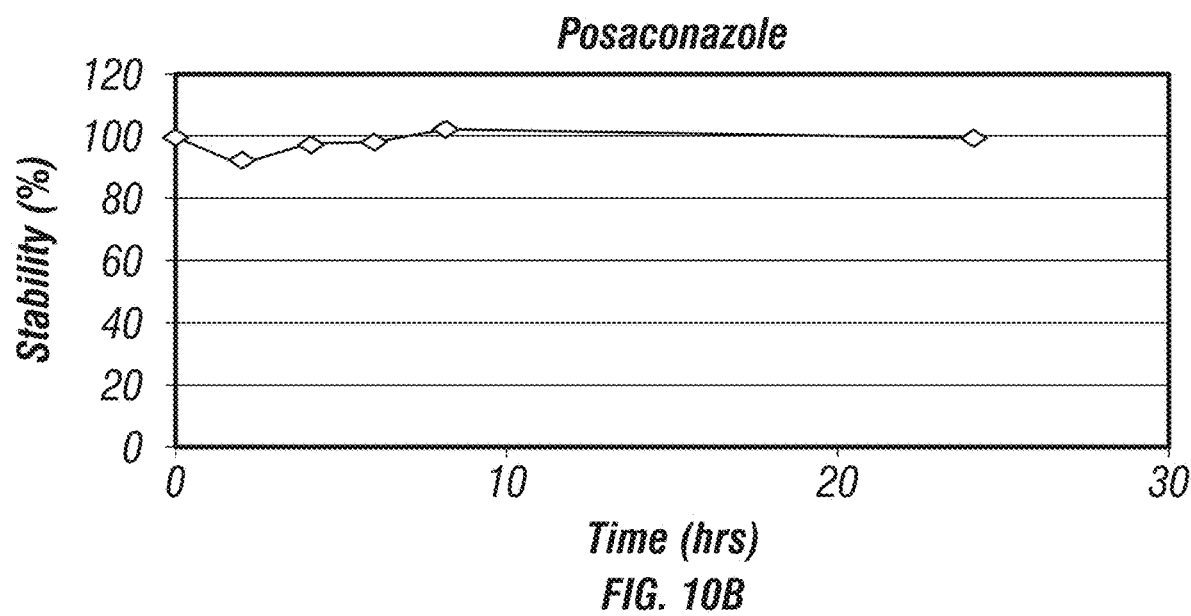

As shown in the Examples, when Itraconazole (Itra) and Posaconazole (Posa) were injected at a dose of 5 mg/kg BW in mice after dissolving and diluting in an analogous fashion (Stability data for the stock- and final use-formulation shown in FIGS. 9 and 10, from ten minutes to at least 2 hours after drug injection the plasma Posa concentrations remained in the 3-5 µg/mL range, and Itra was also detected at more than 0.5 µg/mL over the same time interval. These concentration ranges are similar to what is expected when administering an oral dose equivalent of each drug in a clinical situation (Woestenborghs et al., 1987; Notheis et al., 2006; Courtney et al., 2003; Jang et al., 2010), and these concentrations clearly exceed the minimum inhibitory concentrations of prototype mold strains that are pathogenic to immunocompromised humans.

A variety of biological and chemical methods were used to demonstrate that preferred Bu and azole formulations are stable at approximately 5 mg/mL for several weeks at RT. As shown in the Examples, one such formulation (Bu/VE-acetone/PEG) is stable for greater than 40 or even 60 days, and it retains full cytotoxic activity when assayed in vitro against human leukemic cell lines. Commercially available Bu was dissolved in DMSO and used as a reference solvent system ("D", or "DMSO") for the in vitro cytotoxicity assay. The DMA-Bu formulation was included in some experiments as a positive control in parallel; due to the added synergistic cytotoxic effects of DMA the latter formulation was clearly more toxic in the tested human cell lines. The novel Bu/VE-acetone/PEG/dextrose vehicle is in itself virtually nontoxic as assayed in the hemolysis assay. Finally, one of the novel formulations was used to show that cytocidal Bu concentrations/antifungal azole concentrations are maintained for several hours in a murine model after IV injection of 10 mg/kg BW and 5 mg/kg BW, respectively.

Although a preferred embodiment of the invention uses acetone and PEG, with D5W as the secondary diluent, other solvent vehicles/diluents that are non-toxic and safe for human administration may be used. No serious clinical adverse effects have been experienced from the use of these diluents. As alternatives to acetone alone, one could also use acidified acetone to allow protonation of reactive groups in the pharmacologically active hydrophobic agent to further enhance its solubility and complex-formation with PEG, likely due to improved electrostatic attraction between the solute and PEG. Alternatively, it is possible to use other volatile organic solvents, such as chloroform by itself or acidified chloroform. For example, the acetone comprises between 1 and 100% of the first solvent and PEG is the preferred second stock solvent; as an alternative, acetone comprises between 95 and 100% of the first solvent and a protonating agent, such as an acid or an alcohol, comprises between 0 and 5% of the first solvent.

Useful infusion fluids include, but are not limited to, normal saline and dextrose in water, or dextrose in water mixed with a protonating agent such as an acid (Martin and Matzke, 1982), or dextrose in water admixed with a small amount of an amphilic solvent such as PEG to further decrease the risk of precipitation when the terminal aqueous diluent is added to the drug stock-formulation. Alternatively, the infusion fluid may be a lipid-based emulsion infusion fluid such as those used for parenteral nutrition (Fortner et al., 1975). Prior to dilution with the infusion fluid, the composition may comprise between 1 and 20 mg/mL of a lipophilic agents such as Bu and, more preferably, comprises between 1 and 5 mg/mL of a lipophilic agents such as Bu. Preferably, the undiluted stock composition is stable for more than 30 days at RT. The clinical use of normal saline (NS), dextrose in water (5-10%), and aqueous lipid emulsions are established, routine means to correct fluid and electrolyte balance and to supply parenteral nutrition. Normal saline and dextrose in water, are also extensively used to dilute various medications for IV use. The aqueous lipid emulsion has not yet found widespread use as a pharmaceutical diluent, but this use has been suggested (Fortner et al., 1975). Similarly, the intravenous administration of (hydrochloric) acid has been used for (rapid) correction of serious metabolic acidosis, but it has not been described as a means to enhance protonation to maintain electrostatic attraction forces between a pharmaceutically active agent and disparate hydrophobic/amphiphilic solvents prior to administration in mammals (Martin and Matzke, 1982). In a particularly preferred embodiment, the secondary diluent is 5-10% dextrose in water and the composition comprises between 0.5 and 2.0 mg/mL of Bu after dilution in the secondary diluent. This diluted composition is stable for at least 12-15 hours at RT.

The novel solutions of the invention are not limited to Bu, but may also be used to facilitate parenteral administration of other hydrophobic, and hard-to-solubilize, aka water-insoluble, drugs. As noted, such agents include, but are not limited to, cytotoxic agents such as derivatives of epipodophyllotoxin, taxanes, Bleomycin, anthracyclines, as well as platinum compounds and camptothecin. They also include antibiotics, such as the poorly water-soluble polyenes and azoles (e.g., Amphotericin B and Natamycin, as well as the antifungal azoles including, but not limited to, itraconazole and posaconazole) as well as antibacterial agents, (e.g., polymyxin B), anti-viral agents and tranquilizing/anesthetic drugs such as benzodiazepines, Propofol and anti-psychotic agents.

Additional examples of lipophilic agents that can be used in accordance with the present invention include, but are not limited to, lipophilic active compounds or a salt, isomer, ester, ether or other derivative thereof selected from:

(i) acetylcholinesterase inhibitors selected from donepezil, tacrine, pyridostigmine;

(ii) analgesics and nonsteroidal antiinflammatory agents (NSAIA) selected from aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, rofecoxib, sulindac, tetrahydrocannabinol, tramadol and tromethamine, (iii) anthelminthics selected from albendazole, bephenium hydroxynaphthoate, cambendazole, dichlorophen, fenbendazole, ivermectin, mebendazole, oxamniquine, oxfendazole, oxantel embonate, praziquantel, pyrantel embonate and thiabendazole;

(iv) antiacne agents such as isotretinoin and tretinoin;

(v) antianginal agents selected from amyl nitrate, glyceryl trinitrate (nitroglycerin), isosorbide dinitrate, isosorbide mononitrate, pentaerythritol tetranitrate, and ubidecarenone (coenzyme Q10);

(vi) antiarrhythmic agents selected from amiodarone HCl, digoxin, disopyramide, flecamide acetate and quinidine sulfate;

(vii) anti-asthma agents selected from zileuton, zafirlukast, terbutaline sulfate, montelukast, and albuterol;

(viii) antibacterial agents, including antibiotics, selected from alatrofloxacin, azithromycin, aztreonam, baclofen, benzathine penicillin, cefixime, cefuraxime axetil, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, phenoxymethyl penicillin, rifabutine, rifampicin, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

(ix) anti-benign prostate hypertrophy (BPH) agents selected from alfuzosin, doxazosin, phenoxybenzamine, prazosin, terazosin and tamulosin;

(x) anticancer agents and immunosuppressants selected from abarelix, aldesleukin, alemtuzumab, alitretinoin, all-trans retinoic acid (ATRA), altretamine, amifostine, aminoglutethimide, amsacrine, anastrozole, arsenic trioxide, asparaginase, azacitidine, azathioprine, BCG Live, bevacizumab (avastin), bexarotene, bicalutamide, bisantrene, bleomycin, bortezomib, busulfan, calusterone, camptothecin, capecitabine, carboplatin, carmustine, celecoxib, cetuximab, chlorambucil, cisplatin, cladribine, clofarabine, cyclophosphamide, cyclosporin, cytarabine, dacarbazine, dactinomycin, darbepoetin alfa, daunorubicin, denileukin, dexrazoxane, docetaxel, doxorubicin (neutral), doxorubicin HCl, dromostanolone propionate, ellipticine, enlimomab, estramustine, epirubicin, epoetin alfa, erlotinib, estramustine, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, mesna, methotrexate, methoxsalen, mitomycin C, mitotane, mitoxantrone, mofetil mycophenolate, nandrolone, nelarabine, nilutamide, nofetumomab, oprelvekin, oxaliplatin, paclitaxel, palifermin, pamidronate, pegademase, peg-asparaginase, peg-filgrastim, pemetrexed disodium, pentostatin, pipobroman, plicamycin, porfimer sodium, procarbazine, quinacrine, rasburicase, rituximab, sargramostim, sirolimus, sorafenib, streptozocin, sunitinib maleate, tacrolimus, tamoxifen citrate, temozolomide, teniposide, testolactone, thioguanine, thiotepa, topotecan, toremifene, tositumomab, trastuzumab, tretinoin, uracil mustard, valrubicin, vinblastine, vincristine, vinorelbine, zoledronate, and zoledronic acid;

(xi) anticoagulants selected from cilostazol, clopidogrel, dicumarol, dipyridamole, nicoumalone, oprelvekin, phenindione, ticlopidine, and tirofiban;

(xii) antidepressants selected from amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

(xiii) antidiabetics selected from acetohexamide, chlorpropamide, glibenclamide, gliclazide, glipizide, glimepiride, glyburide, miglitol, pioglitazone, repaglinide, rosiglitazone, tolazamide, tolbutamide and troglitazone;

(xiv) antiepileptics selected from beclamide, carbamazepine, clonazepam, thotoin, felbamate, fosphenyloin sodium, lamotrigine, methoin, methsuximide, methylphenobarbitone, oxcarbazepine, paramethadione, phenacemide, phenol barbitone, phenyloin, phensuximide, primildone, sulthiame, tiagabine HCl, topiramate, valproic acid, and vigabatrin;

(xv) antifungal agents selected from amphotericin, butenafine HCl, butoconazole nitrate, clotrimazole, econazole nitrate, fluconazole, flucytosine, griseofulvin, Itraconazole, ketoconazole, miconazole, natamycin, nystatin, sulconazole nitrate, oxiconazole, Posaconazole, terbinafine HCl, terconazole, tioconazole and undecenoic acid;

(xvi) antigout agents selected from allopurinol, probenecid and sulphinpyrazone;

(xvii) antihypertensive agents selected from amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

(xviii) antimalarial agents selected from amodiaquine, chloroquine, chlorproguanil HCl, halofantrine HCl, mefloquine HCl, proguanil HCl, pyrimethamine and quinine sulfate;

(xix) antimigraine agents selected from dihydroergotamine mesylate, ergotamine tartrate, frovatriptan, methysergide maleate, naratriptan HCl, pizotifen maleate, rizatriptan benzoate, sumatriptan succinate, and zolmitriptan;

(xx) antimuscarinic agents selected from atropine, benzhexol HCl, biperiden, ethopropazine HCl, hyoscyamine, mepenzolate bromide, oxyphencyclimine HCl and tropic amide (xxi) antiparkinsonian agents selected from bromocriptine mesylate, lysuride maleate, pramipexole, ropinirole HCl, and tolcapone;

(xxii) antiprotozoal agents selected from atovaquone, benznidazole, clioquinol, decoquinate, diiodohydroxyquinoline, diloxamide furoate, dinitolmide, furazolidone, metronidazole, nimorazole, nitrofurazone, ornidazole and tinidazole;

(xxiii) antithyroid agents selected from carbimazole and propylthiouracil;

(xxiv) antitussive agent such as benzonatate;

(xxv) antiviral agents selected from abacavir, amprenavir, delavirdine, efavirenz, indinavir, lamivudine, nelfinavir, nevirapine, ritonavir, saquinavir, and stavudine;

(xxvi) anxiolytics, sedatives, hypnotics and neuroleptics selected from alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, propofol, pseudoephedrine, quetiapine, risperidone, sertindole, sulpiride, temazepam, thioridazine, triazolam, zolpidem, and zopiclone;

(xxvii) beta.-blockers selected from acebutolol, alprenolol, atenolol, labetalol, metoprolol, nadolol, oxprenolol, pindolol and propranolol;

(xxviii) cardiac inotropic agents selected from anrinone, digitoxin, digoxin, enoximone, lanatoside C and medigoxin;

(xxix) corticosteroids selected from beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

(xxx) diuretics selected from acetazolamide, amiloride, bendroflumethiazide, bumetanide, chlorothiazide, chlorthalidone, ethacrynic acid, frusemide, metolazone, spironolactone and triamterene;

(xxxi) gastrointestinal agents selected from bisacodyl, cimetidine, cisapride, diphenoxylate HCl, domperidone, famotidine, lansoprazole, loperamide, mesalazine, nizatidine, omeprazole, ondansetron HCl, pantoprazole, rabeprazole sodium, ranitidine HCl and sulphasalazine;

(xxxii) histamine H1- and H2-receptor antagonists selected from acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

(xxxiii) keratolytic agents selected from acetretin, calcipotriene, calcifediol, calcitriol, cholecalciferol, ergocalciferol, etretinate, retinoids, targretin, and tazarotene;

(xxxiv) lipid regulating/hypolipidemic agents selected from atorvastatin, bezafibrate, cerivastatin, ciprofibrate, clofibrate, fenofibrate, fluvastatin, gemfibrozil, hesperetin, lovastatin, pravastatin, probucol, and simvastatin;

(xxxv) muscle relaxants selected from cyclobenzaprine, dantrolene sodium and tizanidine HCl;

(xxxvi) opioid analgesics selected from codeine, dextropropoxyphene, diamorphine, dihydrocodeine, fentanyl, meptazinol, methadone, morphine, nalbuphine and pentazocine;

(xxxvii) sex hormones selected from clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, mifepristone, norethisterone, norgestrel, oestradiol, conjugated estrogens, progesterone, rimexolone, stanozolol, stilbestrol, testosterone and tibolone;

(xxxviii) stimulants selected from amphetamine, dexamphetamine, dexfenfluramine, fenfluramine and mazindol;

(xxxix) nutraceutical agents selected from calcitriol, carotenes, chrysin, dihydrotachysterol, flavonoids, hesperitin, jasmonates, lipoic acid, lutein, lycopene, essential fatty acids, non-essential fatty acids, naringenin, phytonadiol, quercetin, vitamins including vitamin A, vitamin B2, vitamin D and derivatives, vitamin E, and vitamin K, coenzyme Q10 (ubiquinone), plant extracts, and minerals.

Analgesics may be used in certain aspects of the invention. An analgesic (also known as a painkiller) is any member of the group of drugs used to relieve pain (achieve analgesia). The word analgesic derives from Greek an- ("without") and algos ("pain").

Analgesic drugs act in various ways on the peripheral and central nervous systems; they include paracetamol (para-acetylaminophenol, also known in the US as acetaminophen), the non-steroidal anti-inflammatory drugs (NSAIDs) such as the salicylates, and opioid drugs such as morphine and opium. They are distinct from anesthetics, which reversibly eliminate sensation.

Nonsteroidal anti-inflammatory drugs, usually abbreviated to NSAIDs or NAIDs, but also referred to as nonsteroidal anti-inflammatory agents/analgesics (NSAIAs) or non-steroidal anti-inflammatory medicines (NSAIMs), are drugs with analgesic and antipyretic (fever-reducing) effects and which have, in higher doses, anti-inflammatory effects. NSAIDs are generally indicated for the symptomatic relief of the following conditions: Rheumatoid arthritis, Osteoarthritis, Inflammatory arthropathies (e.g. ankylosing spondylitis, psoriatic arthritis, Reiter's syndrome), Acute gout, Dysmenorrhoea (menstrual pain), Metastatic bone pain, Headache and migraine, Postoperative pain Mild-to-moderate pain due to inflammation and tissue injury, Pyrexia (fever), Ileus, Renal colic, or neonate infants whose ductus arteriosus is not closed within 24 hours of birth.

COX-2 selective inhibitor is a form of non-steroidal anti-inflammatory drug (NSAID) that directly targets COX-2, an enzyme responsible for inflammation and pain. Selectivity for COX-2 reduces the risk of peptic ulceration, and is the main feature of celecoxib, rofecoxib and other members of this drug class. COX-2 selectivity does not seem to reduce other adverse effects of NSAIDs (most notably an increased risk of renal failure), and some results have shown an increase in the risk for heart attack, thrombosis and stroke by a relative increase in thromboxane. Rofecoxib is one example.

Flupirtine is a centrally acting K+ channel opener with weak NMDA antagonist properties. It is used in Europe for moderate to strong pain and migraine and its muscle relaxant properties. It has no anticholinergic properties and is believed be devoid of any activity on dopamine, serotonin or histamin receptors. It is not addictive and tolerance does not develop.

In patients with chronic or neuropathic pain, various other substances may have analgesic properties. Tricyclic antidepressants, especially amitriptyline, have been shown to improve pain in what appears to be a central manner. Nefopam is used in Europe for pain relief with concurrent opioids. The exact mechanism of carbamazepine, gabapentin and pregabalin is similarly unclear, but these anticonvulsants are used to treat neuropathic pain with differing degrees of success. Anticonvulsants are most commonly used for neuropathic pain as their mechanism of action tends to inhibit pain sensation.

Antidepressants may be used in certain aspects of the invention. Tricyclic antidepressants (TCAs) are heterocyclic chemical compounds used primarily as antidepressants. The TCAs were first discovered in the early 1950s and were subsequently introduced later in the decade; They are named after their chemical structure, which contains three rings of atoms. The tetracyclic antidepressants (TeCAs), which contain four rings of atoms, are a closely related group of antidepressant compounds.

The TCAs include the following agents which are predominantly serotonin and/or norepinephrine reuptake inhibitors: Amitriptyline (Elavil, Tryptizol, Laroxyl), Amitriptylinoxide (Amioxid, Ambivalon, Equilibrin), Butriptyline (Evadyne), Clomipramine (Anafranil), Demexiptiline (Deparon, Tinoran), Desipramine (Norpramin, Pertofrane), Dibenzepin (Noveril, Victoril), Dimetacrine (Istonil, Istonyl, Miroistonil), Dosulepin/Dothiepin (Prothiaden), Doxepin (Adapin, Sinequan), Imipramine (Tofranil, Janimine, Praminil), Imipraminoxide (Imiprex, Elepsin), Lofepramine (Lomont, Gamanil), Melitracen (Deanxit, Dixeran, Melixeran, Trausabun), Metapramine (Timaxel), Nitroxazepine (Sintamil), Nortriptyline (Pamelor, Aventyl), Noxiptiline (Agedal, Elronon, Nogedal), Pipofezine (Azafen/Azaphen), Propizepine (Depressin, Vagran), Protriptyline (Vivactil), Quinupramine (Kevopril, Kinupril, Adeprim, Quinuprine)

As well as the following atypical compounds: Amineptine (Survector, Maneon, Directim)—Norepinephrine-dopamine reuptake inhibitor; Iprindole (Prondol, Galatur, Tetran)—5-HT2 receptor antagonist; Opipramol (Insidon, Pramolan, Ensidon, Oprimol)—σ receptor agonist; Tianeptine (Stablon, Coaxil, Tatinol)—Selective serotonin reuptake enhancer; Trimipramine (Surmontil)—5-HT2 receptor antagonist In recent times, the TCAs have been largely replaced in clinical use in most parts of the world by newer antidepressants such as the selective serotonin reuptake inhibitors (SSRIs) and serotonin-norepinephrine reuptake inhibitors (SNRIs), which typically have more favourable side-effects profiles, though they are still sometimes prescribed for certain indications.

Selective serotonin reuptake inhibitors or serotonin-specific reuptake inhibitor. (SSRIs) are a class of compounds typically used as antidepressants in the treatment of depression, anxiety disorders, and some personality disorders. They are also typically effective and used in treating some cases of insomnia. The main indication for SSRIs is clinical depression. SSRIs are frequently prescribed for anxiety disorders, such as social anxiety, panic disorders, obsessive-compulsive disorder (OCD), eating disorders, chronic pain and occasionally, for posttraumatic stress disorder (PTSD). Though not specifically indicated by the manufacturers, they are sometimes prescribed to treat irritable bowel syndrome (IBS), Lichen simplex chronicus and premature ejaculation. All SSRIs are approved in the U.S. for use with psychiatric disorders as outlined in the Diagnostic and Statistical Manual of Mental Disorders (DSM IV).

SSRIs are believed to increase the extracellular level of the neurotransmitter serotonin by inhibiting its reuptake into the presynaptic cell, increasing the level of serotonin in the synaptic cleft available to bind to the postsynaptic receptor. They have varying degrees of selectivity for the other monoamine transporters, with pure SSRIs having only weak affinity for the noradrenaline and dopamine transporter.

SSRI Drugs include (trade names in parentheses): citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Prozac, Fontex, Seromex, Seronil, Sarafem, Ladose, Motivest, Flutop, Fluctin (EUR), Fluox (NZ), Depress (UZB), Lovan (AUS)); fluvoxamine (Luvox, Fevarin, Faverin, Dumyrox, Favoxil, Movox); indalpine (Upstene) (discontinued); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibyrd); zimelidine (Zelmid, Normud) (discontinued).

Serotonin-norepinephrine reuptake inhibitors (SNRIs) are a class of antidepressant drugs used in the treatment of major depression and other mood disorders. They are sometimes also used to treat anxiety disorders, obsessive-compulsive disorder (OCD), attention deficit hyperactivity disorder (ADHD), chronic neuropathic pain, fibromyalgia syndrome (FMS), and for the relief of menopausal symptoms.

SNRIs act upon and increase the levels of two neurotransmitters in the brain that are known to play an important part in mood, these being serotonin and norepinephrine. This can be contrasted with the more widely-used selective serotonin reuptake inhibitors (SSRIs) which only act on serotonin.

Examples of SNRIs include:

Venlafaxine (Effexor)—The first and most commonly used SNRI. It was introduced by Wyeth in 1994. The reuptake effects of venlafaxine are dose dependent. At low doses (<150 mg/day) it acts only on serotonergic transmission. At moderate doses (>150 mg/day) it acts on serotonergic and noradrenergic systems, whereas at high doses (>300 mg/day) it also affects dopaminergic neurotransmission.

Desvenlafaxine (Pristiq)—The active metabolite of venlafaxine. It is believed to work in a similar manner, though some evidence suggests lower response rates compared to venlafaxine and duloxetine. It was introduced by Wyeth in May 2008.

Duloxetine (Cymbalta, Yentreve)—By Eli Lilly and Company, has been approved for the treatment of depression and neuropathic pain in August 2004. Duloxetine is contraindicated in patients with heavy alcohol use or chronic liver disease, as duloxetine can increase the levels of certain liver enzymes which can lead to acute hepatitis or other diseases in certain at risk patients. Currently, the risk of liver damage appears only to be for patients already at risk, unlike the antidepressant nefazodone which, though rare, can spontaneously cause liver failure in healthy patients. Duloxetine is also approved for Major Depressive Disorder (MDD), Generalized Anxiety Disorder (GAD), chronic musculoskeletal pain, including chronic osteoarthritis pain and chronic low back pain (as of October, 2010), and is one of the only three medicines approved by the FDA for Fibromyalgia.

Milnacipran (Dalcipran, Ixel, Savella)—Shown to be significantly effective in the treatment of depression and fibromyalgia. The Food and Drug Administration (FDA) approved milnacipran for treatment of fibromyalgia in the United States of America in January 2009, however it is currently not approved for depression in that country. Milnacipran has been commercially available in Europe and Asia for several years.

Levomilnacipran (F2695)—The levo-isomer of milnacipran. Under development for the treatment of depression in the United States and Canada.

Sibutramine (Meridia, Reductil)—An SNRI, which, instead of being developed for the treatment of depression, was widely marketed as an appetite suppressant for weight loss purposes.

Bicifadine (DOV-220,075)—By DOV Pharmaceutical, potently inhibits the reuptake of serotonin and norepinephrine (and dopamine to a lesser extent), but rather than being developed for the already crowded antidepressant market, it is being researched as a non-opioid, non-NSAID analgesic.

SEP-227162—An SNRI under development by Sepracor for the treatment of depression.

LY 2216684—An SNRT under development by Eli Lilly for the treatment of depression.

Antipsychotics may be used in certain aspects of the invention. An antipsychotic (or neuroleptic) is a tranquilizing psychiatric medication primarily used to manage psychosis (including delusions or hallucinations, as well as disordered thought), particularly in schizophrenia and bipolar disorder. A first generation of antipsychotics, known as typical antipsychotics, was discovered in the 1950s. Most of the drugs in the second generation, known as atypical antipsychotics, have been developed more recently, although the first atypical antipsychotic, clozapine, was discovered in the 1950s and introduced clinically in the 1970s. Both generations of medication tend to block receptors in the brain's dopamine pathways, but antipsychotic drugs encompass a wide range of receptor targets.

Common conditions with which antipsychotics might be used include schizophrenia, bipolar disorder and delusional disorder. Antipsychotics might also be used to counter psychosis associated with a wide range of other diagnoses, such as psychotic depression. However, not all symptoms require heavy medication and hallucinations and delusions should only be treated if they distress the patient or produce dangerous behaviors.

In addition, "antipsychotics" are increasingly used to treat non-psychotic disorders. For example, they are sometimes used off-label to manage aspects of Tourette syndrome or autism spectrum disorders. They have multiple off-label uses as an augmentation agent (i.e. in addition to another medication), for example in "treatment-resistant" depression or OCD. Despite the name, the off-label use of "antipsychotics" is said to involve deploying them as antidepressants, anti-anxiety drugs, mood stabilizers, cognitive enhancers, anti-aggressive, anti-impulsive, anti-suicidal and hypnotic (sleep) medications.

Antipsychotics have also been increasingly used off-label in cases of dementia in older people, and for various disorders and difficulties in children and teenagers. A survey of children with pervasive developmental disorder found that 16.5% were taking an antipsychotic drug, most commonly to alleviate mood and behavioral disturbances characterized by irritability, aggression, and agitation. Recently, risperidone was approved by the US FDA for the treatment of irritability in children and adolescents with autism.

Antipsychotics may include first generation antipsychotics (typical antipsychotic), Butyrophenones, Phenothiazines, Thioxanthenes, second generation antipsychotics (atypical antipsychotic), third generation antipsychotics, Cannabidiol (CBD), etc.

Antipsychotics are sometimes used as part of compulsory treatment via inpatient (hospital) commitment or outpatient commitment. This may involve various methods to persuade a person to take the medication, or actual physical force. Administration may rely on an injectable form of the drug rather than tablets. The injection may be of a long-lasting type known as a depot injection, usually applied at the top of the buttocks. Those that are available in injectable form are haloperidol, olanzapine, and ziprasidone while those available as depot are haloperidol, flupenthixol, clopenthixol, and risperidone.

The atypical antipsychotics (AAP) (also known as second generation antipsychotics) are a group of antipsychotic tranquilizing drugs used to treat psychiatric conditions. Some atypical antipsychotics are FDA approved for use in the treatment of schizophrenia. Some carry FDA approved indications for acute mania, bipolar depression, psychotic agitation, bipolar maintenance, and other indications. The atypical antipsychotics may include: Amisulpride (Solian), Aripiprazole (Abilify), Asenapine (Saphris), Blonanserin (Lonasen), Clotiapine (Entumine), Clozapine (Clozaril), Iloperidone (Fanapt), Lurasidone (Latuda), Mosapramine (Cremin), Olanzapine (Zyprexa), Paliperidone (Invega), Perospirone (Lullan), Quepin (Specifar), Quetiapine (Seroquel), Remoxipride (Roxiam), Risperidone (Risperdal), Sertindole (Serdolect), Sulpiride (Sulpirid, Eglonyl), Ziprasidone (Geodon, Zeldox), Zotepine (Nipolept), Bifeprunox (DU-127,090), Pimavanserin (ACP-103), Vabicaserin (SCA-136). Third generation antipsychotics may include Aripiprazole (Abilify) or partial agonists of dopamine.

Anesthetics may be used in certain aspects of the invention. An anesthetic (or anaesthetic, see spelling differences) is a drug that causes anesthesia—reversible loss of sensation. They contrast with analgesics (painkillers), which relieve pain without eliminating sensation. These drugs are generally administered to facilitate surgery. A wide variety of drugs are used in modern anesthetic practice. Many are rarely used outside of anesthesia, although others are used commonly by all disciplines. Anesthetics are categorized in to two classes: general anesthetics, which cause a reversible loss of consciousness, and local anesthetics, which cause a reversible loss of sensation for a limited region of the body while maintaining consciousness. Combinations of anesthetics are sometimes used for their synergistic and additive therapeutic effects, however, adverse effects may also be increased.

Local anesthetics are agents that prevent transmission of nerve impulses without causing unconsciousness. They act by binding to fast sodium channels from within (in an open state). Local anesthetics can be either ester or amide based. Ester local anesthetics (e.g., procaine, amethocaine, cocaine) are generally unstable in solution and fast-acting, and allergic reactions are common. Non-limiting examples of local anesthetics may include procaine, amethocaine, cocaine, lidocaine (also known as Lignocaine), prilocaine, bupivacaine, levobupivacaine, ropivacaine, mepivacaine, and dibucaine. Amide local anesthetics (e.g., lidocaine, prilocaine, bupivicaine, levobupivacaine, ropivacaine, mepivacaine and dibucaine) are generally heat-stable, with a long shelf life (around 2 years). They have a slower onset and longer half-life than ester anesthetics, and are usually racemic mixtures, with the exception of levobupivacaine (which is S(-)-bupivacaine) and ropivacaine (S(-)-ropivacaine). These agents are generally used within regional and epidural or spinal techniques, due to their longer duration of action, which provides adequate analgesia for surgery, labor, and symptomatic relief. Only preservative-free local anesthetic agents may be injected intrathecally.

A general anaesthetic (or anesthetic, see spelling differences) is a drug that brings about a reversible loss of consciousness. These drugs are generally administered by an anaesthesia provider to induce or maintain general anaesthesia to facilitate surgery. The biological mechanism(s) of the action of general anaesthetics are not well understood. Injection anaesthetics are used for induction and maintenance of a state of unconsciousness. Anaesthetists prefer to use intravenous injections, as they are faster, generally less painful and more reliable than intramuscular or subcutaneous injections. Among the most widely used drugs are: Propofol, Etomidate, Barbiturates such as methohexital and thiopentone/thiopental, Benzodiazepine derivatives such as midazolam, and Ketamine.

The compositions of the invention have a number of uses. The invention may include a method for treating a disease that is sensitive or responsive to a lipophilic drug treatment comprising: parenterally administering a therapeutically effective amount of a parenteral drug composition as described above to a patient.

Diseases or conditions that may be treated include, but are not limited to, cancer, acute and chronic leukemia, Hodgkin's and Non-Hodgkin's lymphoma, a myeloproliferative disorder, an autoimmune disease and as forming the basis of combination chemotherapy intended to prepare a patient for hematopoietic progenitor cell transplantation, infectious diseases, psychotic conditions or disease, or a need of symptom control. Preferably, the composition may be administered intravascularly, but as determined by specific clinical circumstances it may also be given intrathecally, intracavitary (such as e.g. intraperitoneally, or intrapleurally) among other routes to treat locally advanced disease. After mixing with or suspending in a suitable ointment base, the composition may also be applied topically, such as in the treatment of a peripheral T-cell lymphoma or in the case of using the composition as a base solvent system for an anti-infectious composition suitable for topical administration to accomplish a remedy for a localized infectious or inflammatory ailment. The patient can be any animal. More preferably, the animal is a mammal, and most preferably, a human.

The term "therapeutically effective amount" as used in this application means that a sufficient amount of the composition is added to achieve the desired therapeutic effect or another effect, e.g., to transiently achieve symptom control, or alter the patient's level of consciousness. The actual amount used will vary based on factors such as the type of medical condition, the age, sex, health, species and weight of the patient, and the type of use and length of use, as well as other factors known to those skilled in the art.

Still another embodiment of the invention is directed to a method for parenterally administering a lipophilic agent to a patient comprising: 1) providing a primary solvent vehicle in the form of an organic solvent; 2) mixing the solubilized pharmaceutically active agent, e.g., Bu, with a secondary hydrophobic/amphiphilic agent, such as PEG; 3) extracting the primary solvent, preferably under vacuum to create a microenvironment that is conducive to electrostatic binding of the pharmaceutically active agent to the polymer, PEG, thus keeping the pharmaceutically-active agent bound to or "dissolved" in PEG after completion of the vacuum-extraction. This may prevent precipitation and thereby to produce a stock formulation; 4) mixing the stock formulation with a secondary diluent to form an infusion fluid; and 5) administering the infusion fluid containing the pharmaceutically-active agent to the patient. Preferably, the primary organic solvent is acetone. However, in addition to acetone, many other organic solvents, such as chloroform and diethyl-ether, may be used to form the primary diluent without departing from the spirit and scope of the invention.

As an example, Bu-based formulations may be useful in the treatment of malignancies and autoimmune diseases in man and animals. Certain hematologic malignancies, most notably the myeloid neoplasms, such as CIVIL, AML, MDS, as well as Hodgkin's and Non-Hodgkin's lymphomas, may be controlled with Bu-based therapy for prolonged time periods, especially when utilized in pretransplant conditioning therapy. The nontoxic, pharmaceutically acceptable, water miscible, parenteral Bu-based formulations eliminate the risk of treatment failure from unpredictable and erratic intestinal absorption and first-pass liver elimination/metabolism that to varying degrees characterize administration of the oral standard preparation, and it avoids the unpredictable and erratic toxicity of DMA used in the only currently available IV Bu-formulation. The potential benefits of the new parenteral formulation(s) not only include(s) fewer side effects than that experienced with oral drug, since intravascular administration gives complete control of the drug's bioavailability and pharmacokinetics, but it avoids the unpredictable adverse synergistic interaction(s) of Bu and DMA. It also safeguards against possible unpredictable adverse interaction(s) between other concomitantly administered chemotherapeutic agents and DMA in the case of combination chemotherapy. It should be noted that DMA, at the resulting final concentrations, contributed significant synergistic toxicity in at least four tested human cell lines, but this is conceivably also the case for normal-organ toxicity in both human and animal settings as discussed above.

Additional exemplary formulations of the invention may be useful in the treatment of fungal, yeast and mold infections in mammals, particularly *Candida, Aspergillus* or Mucorales infection. Certain infections, most notably those caused by *Histoplasma* Spp. and *Aspergillus* Spp. may be successfully controlled by Itra, and Posa has in addition been of particular value in treatment of mucormycosis in immunocompromised patients. The novel formulations, such as nontoxic, pharmaceutically acceptable, water-miscible, intravascular Itra or Posa formulations, eliminate the risk of treatment failure from unpredictable and erratic intestinal absorption and first-pass liver elimination/metabolism that to varying degrees characterize administration of the oral standard preparation(s). The potential benefits of using the intravascular administration route/formulation is most evident in severely ill patients with an impaired ability to swallow and therefore unable to benefit from oral nutrition such as for instance patients suffering from oral and gastrointestinal mucositis after radio- and/or chemotherapy for neoplastic disease and those suffering from gastrointestinal graft-vs-host disease after allogeneic stem cell transplantation where a similar clinical conundrum exists. The benefits are also expected to include fewer clinical side effects than that experienced with the corresponding oral drug formulation, since intravascular administration gives complete control of the bioavailability with optimized pharmacokinetics of the drugs and therefore minimizes the risk for side effects due to unwanted drug-drug interactions and treatment-failure secondary to incomplete intestinal absorption as well as accidental overdosing in patients who have an unexpectedly high intestinal absorption paired with a low metabolic drug clearance.

The novel formulations may also be used to investigate different administration schedules (e.g., prolonged IV infusions, and repeated IV dosing) to optimize treatment outcome for lipophilic drug-based therapy, such as for Bu-based therapy, because now that higher stable Bu concentrations (1-2 mg/mL) and extended stability (with Bu at least 15 hours at RT in the final use-formulation, at 1 mg/mL) is obtained. Further, the invention makes it possible to investigate the benefits of different dose schedules of the lipophilic agents, such as busulfan or azole drugs against various systemic diseases, without the confounding adverse effects from unpredictable intestinal drug absorption and hepatic first-pass effects that in an arbitrary fashion influence the metabolism of orally administered drugs.

The availability of a new parenteral preparation, especially one that is free from DMA, is of particular interest when dose-intensive schedules are contemplated, and in particular in the pediatric patient population, where side effects such as those exemplified by impaired growth and retardation of both physical and intellectual development may be more pronounced. In this specific situation a lack of solvent-system-related toxicity linked together with absolute Bu bioavailability and precise pharmacokinetics are of utmost importance to ensure optimal patient safety through control of the drug's clinical adverse effect profile, yet maximizing the chance for long-term disease control.

For infectious disease, the novel formulations and methods may obviate the need to contend with the highly variable intestinal absorption that has been reported between patients with different underlying diseases as well as different age categories (Willems et al., 2001), and whether the patient is fed or fasting (Dodds-Ashley, 2010; Willems et al., 2001; Van de Velde et al., 1996), and the novel formulations and methods also alleviate the need to worry about the "saturable" intestinal drug absorption that has been described after Posa administration (Courtney et al., 2003). The availability of a novel parenteral preparation may be also important when more dose-intensive schedules are contemplated to control overwhelming diseases or infections in severely immunocompromised patients, such as sino-pulmonary Aspergillosis and Mucormycosis early after hematopoietic stem cell transplantation. Particularly, absolute drug bioavailability and predictable pharmacokinetics are of utmost importance to ensure the patient's safety through control of a drug's clinical side effects, while maximizing the chance for rapid control of a clearly life-threatening, rapidly progressive infectious complication in a very complex medical situation, where it is of crucial to rapidly establish control of the infection.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1—Busulfan and Azole Parenteral Formulations

This example demonstrates the successful design of stable formulations of busulfan (Bu), using solvent vehicles that are nontoxic and suitable for parenteral administration. The necessary solubility/stability was calculated, and preparations were evaluated with high-pressure liquid chromatographic (HPLC) technique. The desired solubility and stability of Bu in various solvents relevant for parenteral, (as represented by intravascular or intrathecal or intracavitary) administration in humans and domestic animals was defined, and the solubility of Bu in physiologically acceptable vehicles was determined.

Preparation of Prototype Solvent Vehicle and Primary Stock Solution.

A preferred Bu Vacuum-Extracted or Vacuum-Evaporated acetone (VE-acetone)/PEG/Bu ("primary stock solution") as referenced in these Examples was prepared as follows: 10 mg/mL of Bu was solubilized in acetone, mixed with PEG400 (1:2, v/v), then extracted at RT under vacuum for at least 5 hours. The stability of Bu in VE-acetone/PEG at RT is graphed in FIG. 1a. The stability of Bu in VE-acetone/PEG and diluted in D5W at 0.5 mg/mL and 1 mg/mL is displayed in FIG. 1b.

Calculation of Desired Solubility.

A relevant solubility range for Bu was calculated by extrapolation from doses known to have significant anti-tumor efficacy in man. Such clinical studies have been conducted using oral Bu, as well as the IV DMA-Bu, the only FDA-approved parenteral Bu formulation. The utilized Bu regimens typically prescribe a dose in the range of 2-10 mg orally once daily until clinical anti-tumor effect is obtained, or intermittent doses of about 20-40 mg/m$^2$ of body surface area (BSA) as determined by white blood counts, in palliative therapy for CIVIL or by repeated administration every 6-24 hours for 2-4 days when used in pre-HSCT conditioning therapy. The clinically most effective/optimal Bu-dose and -schedule are not known, but different approaches have been reported to be successful. The dose-limiting toxicity with both the low-dose daily schedules and the intermittent more intensive dose schedule are bone marrow suppression. The administration of low daily doses over prolonged time has correlated with a slow and insidious onset of bone marrow suppression that is commonly considered safer and a preferred approach in palliative therapy.

The intermittent high-dose schedules of both oral and IV Bu that are extensively used in pretransplant conditioning therapy are typically considered dependent on hematopoietic progenitor cell support, since such schedules are myeloablative. In pretransplant conditioning therapy the most commonly used oral Bu schedule is 1 mg/kg given every 6 hours for a total of 8-16 doses over 2-4 days. Thus, the parenteral DMA-Bu formulation is recommended for pretransplant conditioning therapy at a dose of 0.8 mg/kg given over 2 hours every 6 hours for 16 doses (Busulfex, 2009). The dose-limiting toxicity with the high-dose pretransplant regimens is typically mucositis, liver failure and about 7-10% risk for generalized seizures (Santos et al., 1983; Tutschka et al., 1987; Ciurea et al., 2009; Blaise et al., 1992; Devergie et al., 1995; Hartman et al., 1998; Socie et al., 2001; Grochow et al., 1989; Grochow, 1993; Slattery et al., 1997; Dix et al., 1997; Marcus and Goldman, 1984; Santos, 1989; Vassal et al., 1990; Vassal et al., 1989; Martell et al., 1987; Sureda et al., 1990; Kashyap et al., 2002; Thall et al., 2004; Kim et al., 2005; Lee et al., 2005; Aggarwal et al., 2006; Dean et al., 2010; DeLeve et al., 2002; Russell et al., 2002; De Lima et al., 2004; Andersson et al., 2008). The risks connected with generalized seizure activity as a side effect of high-dose Bu administration resides primarily with (head-)trauma and bronchial aspiration of gastric content during the seizure episode. The seizures connected with busulfan administration can be avoided through the prophylactic use of benzodiazepines or diphenylhydantoin (Grigg et al., 1989; Meloni et al., 1995; Chan et al., 2002; Hassan et al., 1993). The risk for seizures may also be influenced by the Bu administration schedule. Thus, a prolonged infusion schedule provides extended tumor cell drug exposure, while at the same time avoiding sudden high plasma peak concentrations that may be involved in triggering more serious neurological side effects. From these observations the inventors deduced that a stable final-use formulation with a Bu concentration that would allow prolonged infusion should ideally contain between 1 and 2 mg/mL to limit the total volume administered over a short time in a once daily administration schedule.

Busulfan has a short terminal half-life in blood, approximately 2-4 hours, and a prolonged infusion would extend drug exposure to the malignant tissues, yet decrease the plasma peak drug concentration that may be more closely associated with serious neurological side effects.

A solvent system was discovered that provides a use-formulation that is stable (>95%) at room temperature (RT) for long periods of time. FIG. 1a is a graph showing the stability of Bu at room temperature (RT) in the stock-formulation of VE-acetone/PEG (i.e. prototype solvent vehicle) containing Bu at approximately 5 mg/mL. Busulfan dissolved in a solvent vehicle of VE-acetone/PEG, and further diluted to appropriate concentrations with D5W or D10W with 10-20% PEG or with normal saline (NS) to 1 mg/mL is stable at RT for at least 15 hours. The results shown in FIG. 1a show that the stock formulation is stable with no insoluble material or precipitate formed when maintained at room temperature for at least up to 60 days (during the 60 day length of this particular study, the formulation remained completely stable and precipitate free). In FIG. 1b is shown studies demonstrating that when the stock formulation is diluted with D5W, it maintained essentially 100% stability during the time frame studied (up to 15 hours at 1 mg/ml, and up to 25 hours at 0.5 mg/ml). Hydrophobic agents dissolved in our novel solvent vehicles are suitable for prolonged (12±hours) infusion time, yet the stability still leaves a margin of time for convenient handling in the pharmacy and on the medical floor prior to patient administration. For example, if a planned clinical (Bu) treatment dose prescribes 1-5 mg/kg body weight, it will be desirable to arrive at a concentration of 1-2 mg/mL. A stock formulation of 5 to 10 mg/mL of drug (Bu) in VE-acetone/PEG could be easily and conveniently diluted in D5W or another aqueous infusion fluid to achieve the appropriate final use-concentration in a suitable administration volume. The clinician could then elect to infuse the drug over either short or prolonged time periods without having to exchange bags of infusate that might be needed if the formulation were physically unstable or subject to rapid chemical degradation. Finally, the clinician would be less dependent on whether the routine pharmacy service hours permit a certain drug administration schedule.

Enhanced Solubility in Physiologically Acceptable Solvents

The solubility of Bu was determined in several individual vehicles. Briefly, a known amount of Bu, formulated as a powder (Sigma, St Louis, Mo.), was equilibrated in the respective solvent at RT over 1-4 hours. An aliquot was removed, filtered, and further diluted in the HPLC mobile phase (or acetonitrile) before HPLC to determine solubility at a predetermined time. Since Bu is virtually insoluble in, and also is rapidly hydrolyzed in (the presence of) water, the inventors instead examined non-aqueous organic solvent(s), and acetone was ultimately selected as a preferred first solvent. The Bu was dissolved at 10 mg/mL (maximum solubility of about 16 mg/mL, see Table 1), and this primary Bu-acetone composition was subsequently mixed with PEG (1:2, v/v). This secondary composition was further examined relative to an estimate of how to arrive at a (stable) stock formulation that would be useful in a clinical situation. The assumption was made, that intermittent "high-dose" administration or a prolonged infusion would be the preferred modes of administration, i.e., choosing an infusion schedule that would require the solvent vehicle to stably dissolve a concentration of approximately 5-10 mg/mL. Since it was readily recognized that an organic solvent, such as acetone or chloroform, might be unsafe to routinely administer systemically in a human or domestic animal, the inventors investigated removal of the organic solvent (acetone) by vacuum extraction.

TABLE 1

Solubility of Busulfan in various solvents at room tempaerature

| Solvent | Solubility (mg/mL) |
| --- | --- |
| Acetic acid | 3.8 |
| HCl 6N | 0.7 |
| Ethanol | 0.3 |
| Propylene glycol | 0.2 |
| DMA | 49.2 |
| DMSO | 77.9 |
| Acetone | 16.4 (in literature ~25) |
| PEG (~400) | 0.2 |
| PEG:water 1:1 | 0.25 |
| PEG:water 1:2 | 0.19 |
| Water | Negligible (The Merck Index) |

The inventors hypothesized that vacuum-assisted extraction of the primary organic solvent at RT could create a microenvironment that would facilitate a close electrostatic attraction between the hydrophobic drug, Bu, and the amphiphilic polymer PEG, such that precipitation of the pharmaceutically active agent would not occur during the gradual removal of the primary organic solvent. The inventors further hypothesized, that this electrostatic binding would be sufficiently strong to allow the addition of a secondary aqueous diluent without imminent physical precipitation or chemical degradation of the pharmaceutically-active agent. Hence, the primary composite formulation (Bu in acetone and PEG) was subjected to vacuum extraction of the acetone at RT to create the clinical-stock formulation (i.e. Bu/VE-acetone/PEG), that would be miscible with the secondary aqueous diluent, such as NS, 5% or 10% dextrose in water (D5W and D10W, respectively), or soybean lipid emulsion (Liposyn™ or Intralipid™, Pharmacia, Peapack, N.J.). This clinical-stock formulation was then diluted with the secondary aqueous diluent to yield a stable clinical use-formulation. The desired range of Bu-concentrations in this final use-composition is 0.5-2 mg/mL, or more preferably 1-2 mg/mL, as Bu could then be infused parenterally without concern for fluid overload or other side effects related to the total volume infused.

Ultimately, a solvent vehicle composed of an organic solvent alone (for Bu and Posaconazole) or an organic solvent mixed with a small amount of an acid or an alcohol, such as benzylalcohol, to facilitate protonation of functional groups in the pharmaceutically active agent (e.g. itraconazole or posaconazole), to change the drug's polarity and temporarily increase its solubility in the volatile organic solvent, and thereby increase the electrostatic attraction between the pharmaceutically-active agent and the secondary amphiphilic polymeric agent, PEG, when the latter is added. The subsequent vacuum-assisted extraction of the primary organic solvent, e.g. acetone, which can be accomplished at ambient temperature, will sterically optimize the conditions for electrostatic attraction and prevent precipitation of the pharmaceutically-active agent.

The primary organic solvent vehicle, acetone, allowed complete Bu solubilization at concentrations of at least 15 mg/mL, and after mixing with PEG and extraction of the acetone, Bu is stably bound in PEG alone at a concentration of approximately 5-10 mg/mL. Subsequently, the inventors documented that Bu remained stable in solution in the Bu/VE-acetone/PEG stock formulation for at least 60 days at RT (FIG. 1). Once reconstituted with D5W the final clinical use-formulation is stable for at least 15 hours at a concentration of 0.5 to 2 mg/mL at RT.

HPLC Analysis.
Busulfan Derivatization

HPLC assay provides an accurate and sensitive detection system for low concentrations of Bu in solution, both protein-free mixtures and protein-containing fluids (i.e., blood plasma), utilizing fluorescence detection in the UV spectrum. Unfortunately, Bu is a small molecule which does not contain a chromophore. Therefore it was derivatized with diethyldithiocarbamate (DDTC), which subsequently allows liquid chromatographic separation and detection in the UV-spectrum (Bhagwatwar et al., 1996; Andersson et al., 2000; Madden et al., 2007; Chow et al., 1997). The HPLC procedure was carried out as follows: Bu-containing solution (500 µL) was mixed with an equal amount (500 µL) DDTC stock solution (1.17 M in water). The mixture was vortexed for 30 sec and rotated for 5 min on a Tube Rotator (Barnstead International, Dubuque, Iowa). The derivatized Bu was extracted from the reaction mixture with 2 mL ethyl acetate, followed by centrifugation at 1000×g for 10 min (Thermo Electron Corporation, Waltham, Mass.). A 500 µL-aliquot of the ethyl acetate layer was withdrawn and evaporated to dryness under a vacuum evaporator (Scimetrics Inc., Houston, Tex.). The residue was reconstituted by mixing on a vortex machine for 1 min with 250 µL of the mobile phase and subjected to HPLC.

Chemicals

Busulfan (Bu), Sodium Diethyldithiocarbamate (DDTC) and Itraconazole were obtained from Sigma (St. Louis, Mo.). Polyethylene glycol 400 (PEG 400), ethyl acetate, acetonitrile and tetrahydrofuran were purchased from Fisher Scientific (Pittsburgh, Pa.). All chemicals were HPLC grade unless otherwise indicated. Posaconazole was extracted and purified from the commercially available clinical-use formulation (Noxafil™ suspension for oral use) in the medicinal chemistry core facility of the Department of Experimental Therapeutics at the University of Texas MD Anderson Cancer Center.

HPLC Assay
Busulfan

The HPLC system included: an analytical column (Nova-pak C18 with 4-µm beads; 150 mm×3.9 mm; Waters Corporation, Milford, Mass.), an autosampler (Waters model 717 plus autosampler, a pump (Waters model 600E system controller) set to deliver 1.2 mL/min and an UV detector (model Waters™ 486 Tunable Absorbance detector) set at 254 nm. The isocratic mobile phase was a mixture of acetonitrile, tetrahydrofuran, and water at a ratio of 11:4:5. A volume of 30 µL was injected into HPLC for quantitation of Bu. The HPLC assay was linear within a Bu concentration range of 0.1-20 µg/mL. The mobile phase flow rate was 1.2 mL/min for Bu and 1.0 mL/min for Itra and Posa. The analytic system was based on previously established extraction and HPLC experience with busulfan (Bhagwatwar et al., 1996; Andersson et al., 2002; Madden et al., 2007; Martin and Matzke, 1982; Chow et al., 1997).

Examples of authentic Bu chromatograms are shown in FIG. 3, showing chromatograms from the stability studies.

The HPLC conditions are described in Example 1. In these panels the drug analyzed was from the stability study, where Bu was dissolved in the prototype VE-acetone/PEG formulation and further diluted to 0.5 mg/mL and 1 mg/mL, respectively, using D5W as the final solvent. The HPLC retention time under the above conditions utilizing the Nova-Pak C18 column was about 2.5-3 min. The assay was linear from at least 0.1 µg/mL to more than 20 µg/mL in protein-free solutions, i.e., for the solvent system utilized in the formulation-feasibility and -stability studies (FIG. 2, Table 2). FIG. 2 is the Standard curve of Bu concentration vs. area under the curve (AUC) obtained in the HPLC assay used in the stability studies. The x-axis shows concentration in µg/mL, and the y-axis shows the AUC. Analogous standard curves were prepared for the pharmacology studies in mice as appropriate.

TABLE 2

Busulfan Standard Curve - HPLC

| Concentration | RT | AUC | average |
|---|---|---|---|
| 20 ug/mL | 2.623 | 2086599 | |
| | 2.621 | 2132448 | 2047685 |
| | 2.623 | 1924008 | |
| 10 ug/mL | 2.623 | 1058978 | 1040774 |
| | 2.625 | 1089246 | |
| | 2.625 | 974099 | |
| 5 ug/mL | 2.621 | 521298 | 543635 |
| | 2.619 | 558881 | |
| | 2.619 | 550726 | |
| 2.5 ug/mL | 2.613 | 272710 | 283674 |
| | 2.584 | 303896 | |
| | 2.584 | 274417 | |
| 1.25 ug/mL | 2.584 | 157211 | 162242 |
| | 2.588 | 168973 | |
| | 2.591 | 160542 | |
| 0.625 ug/mL | 92934 | 92649 | 92649 |
| | 92690 | | |
| | 92323 | | |

This HPLC assay consistently yielded high recovery and accuracy and an initially lower sensitivity limit of about 1 µg/mL, but by fine-tuning the technique as well as increasing the volume injected in the HPLC beyond the initially used 30 µL, the lower sensitivity limit could be reproducibly improved to a consistent lower quantitative limit of about 25 ng/mL, and a lowest limit of absolute detection of about 5-10 ng/mL (Bhagwatwar et al., 1966; Chow et al., 1997; Andersson et al., 2000; Madden et al., 2007). This HPLC technique was standardized and used for all the stability studies without any further modifications. For the plasma pharmacology study, the appearance of endogenous plasma protein-derived peaks in the chromatogram necessitated the addition of an extraction/purification step; this was accomplished by precipitation of the proteins by adding two volumes of acetonitrile followed by centrifugation and analysis as described.

HPLC Assay

Azole Compounds

The HPLC system was modified from Woestenborghs et al. (1987), and further modified for Posa (Notheis et al., 2006; Courtney et al., 2003; Jang et al., 2010). It used the same basic equipment set-up as described above for analyzing busulfan; thus, the pump was set to a flow rate of 1.0 mL/min. The detection of respective azole was set at 261 nm for both Itra and Posa. The isocratic mobile phase was a mixture of 60% acetonitrile in $H_2O$ plus 0.05% diethylamine. A standardized volume of 10 µL was injected into HPLC column for quantitation of the respective azoles. Briefly, this summarizes the parameters used for the HPLC analysis.

The retention time for Itra was 4.7-5.5 min and 2.5-3.0 min for Posa. As expected it varied somewhat with respect to which particular azole compound was assayed. HPLC assay provides an accurate and sensitive detection system for low concentrations of Itra (azole compounds) in solution, both protein-free mixtures and protein-containing fluids (such as clinically obtained samples, e.g. blood plasma), utilizing fluorescence detection in the UV spectrum. For the detection a wavelength of 261 was chosen, based on the inherent absorption and emission maxima of the azole molecules. This was varied as to which particular azole analog is examined, both the two prototype agents used here, Itra and Posa can be reliably detected at 261 nm.

All chemicals were HPLC grade unless otherwise indicated. Our analytical system was based on previously established HPLC methodology for Itra (Woestenborghs et al., 1987).

To avoid analytical interference from endogenous plasma proteins in the chromatogram when assaying Itra and Posa in plasma samples, an extraction/purification step utilizing precipitation of protein material with acetonitrile was performed. Briefly, plasma proteins were precipitated by adding acetonitrile to a final volume ratio plasma:acetonitrile of 1:2. The mixture was vortexed for 30 seconds and centrifuged for 5 min. at 14,000 rpm in an Eppendorff microcentrifuge. The deproteinated supernatant, containing Itra, was injected into the HPLC to determine the drug concentration.

Examples of authentic Itra chromatograms from the HPLC assay are shown in FIGS. 12 and 13. FIG. 12 depicts chromatograms obtained from the HPLC assay in the (protein-free) stability studies. The injected sample volume was 10 µL. The HPLC conditions were as described above. In these panels the drug analyzed was from the stability study, where Itra was dissolved in the prototype solvent vehicles (a), and further diluted using D5W as the final diluent (b). The HPLC retention time under the above conditions utilizing the C18 Nova-Pak column was 4.7-5.5 min. The assay was linear from 0.1 µg/mL to 100 µg/mL in protein-free solutions, i.e. the various solvent systems utilized in the formulation-feasibility and -stability studies.

Figure 14A:
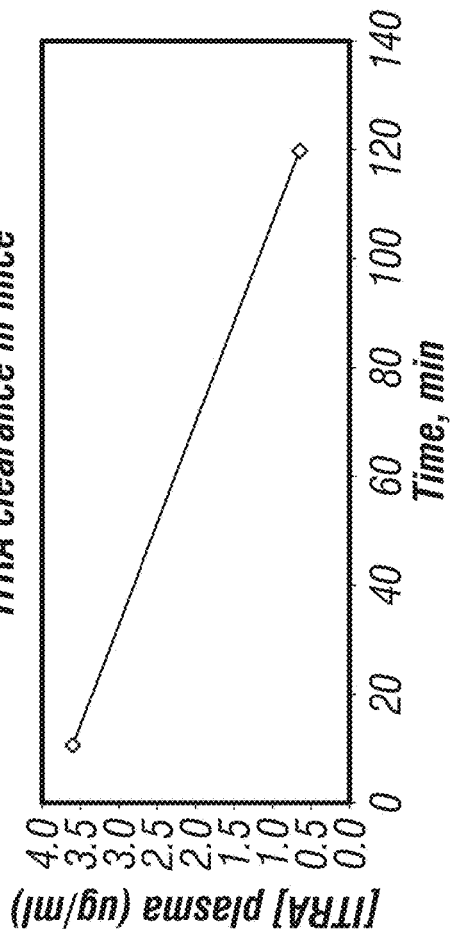
FIGS. 14A-B. Plasma concentrations after injection of Itra (FIG. 14A; over 2 hours) and Posa (FIG. 14B; over 30 hours) injected at a dose of 5 mg/kg slowly IV (over 3-4 min) as described under the methods in the text. The plasma concentrations are in a similar range as previously described in humans treated with the corresponding oral drugs in a clinical setting. The figure shows the average result of 2 different experiments, the individual time points and concentrations are detailed in the accompanying table.
Figure 14B:
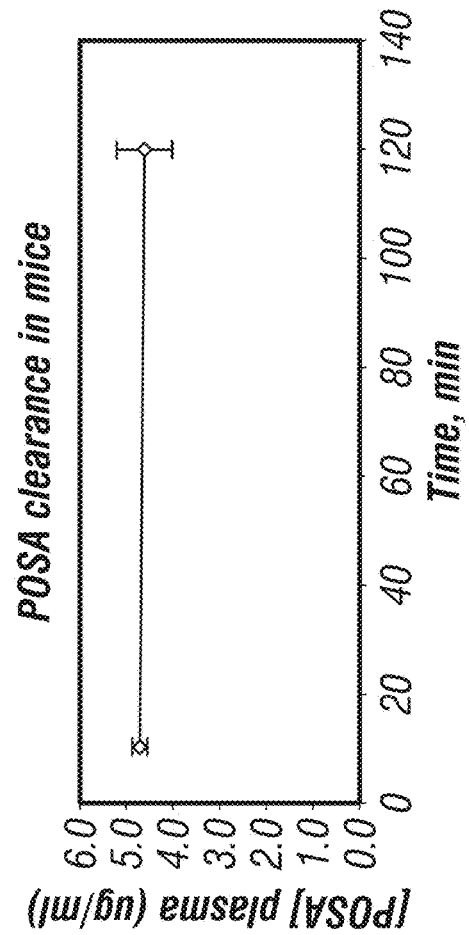

FIG. 14 depicts chromatograms from the plasma assay of Itra and Posa in the pharmacology study. The data are below in Table 3.

TABLE 3

Clearance of a) Itraconazole and b) Posaconazole after injection of 5 mg/kg IV in Swiss Webster mice.

a) Itraconazole

| Time, Min | ug/mL | mean | SD |
|---|---|---|---|
| 10 | 3.59 | 3.23 | 0.76 |
|  | 2.13 |  |  |
|  | 3.34 |  |  |
|  | 3.86 |  |  |
| 30 | 1.31 | 1.62 | 0.44 |
|  | 1.93 |  |  |

TABLE 3-continued

Clearance of a) Itraconazole and b) Posaconazole after injection of 5 mg/kg IV in Swiss Webster mice.

| | | | |
|---|---|---|---|
| 60 | 0.77 | 0.77 |  |
| 120 | 0.64 | 0.71 | 0.09 |
|  | 0.77 |  |  | b) Posaconazole

| Time, hours | ug/mL | mean | SD |
|---|---|---|---|
| 0.2 | 3.43 | 3.68 | 1.34 |
|  | 1.88 |  |  |
|  | 4.59 |  |  |
|  | 4.82 |  |  |
| 2.0 | 4.99 | 4.77 | 0.38 |
|  | 4.85 |  |  |
|  | 5.03 |  |  |
|  | 4.21 |  |  |
| 7.0 | 2.61 | 3.23 | 0.88 |
|  | 3.86 |  |  |
| 24 | 0.03 | 0.35 | 0.28 |
|  | 0.56 |  |  |
|  | 0.47 |  |  |
| 30 | 0.14 | 0.16 | 0.13 |
|  | 0.29 |  |  |
|  | 0.04 |  |  |

This HPLC assay consistently yielded high recovery and accuracy and a lower sensitivity limit of about 10-20 ng/mL, sufficient for the planned experiments. This HPLC technique was standardized and used for all stability studies without additional modifications, except as necessitated by assaying the different azole-analogs.

Figure 11:
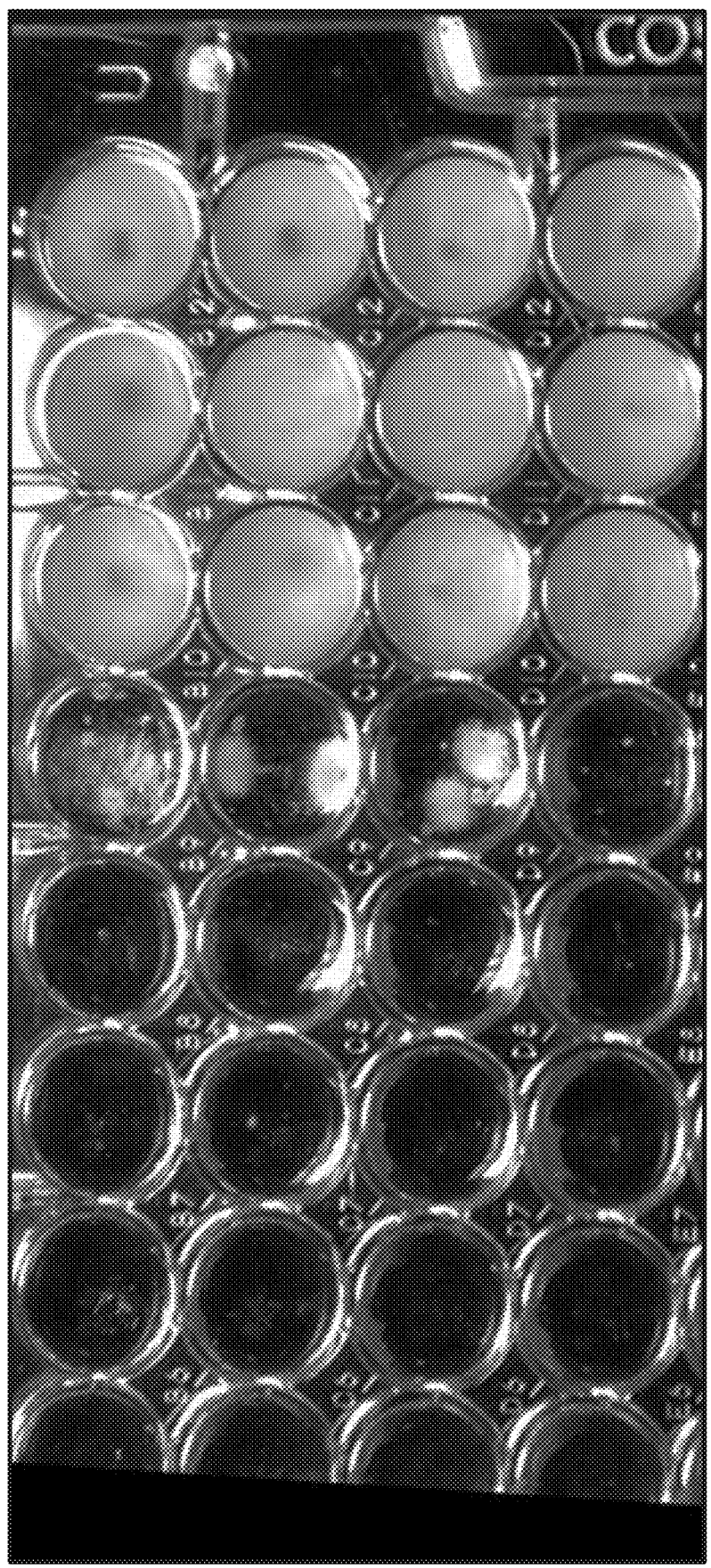
FIG. 11. Photograph of in vitro sensitivity test of *Aspergillus* species to Itraconazole in the new formulation, for details see text.
Figure 12A:
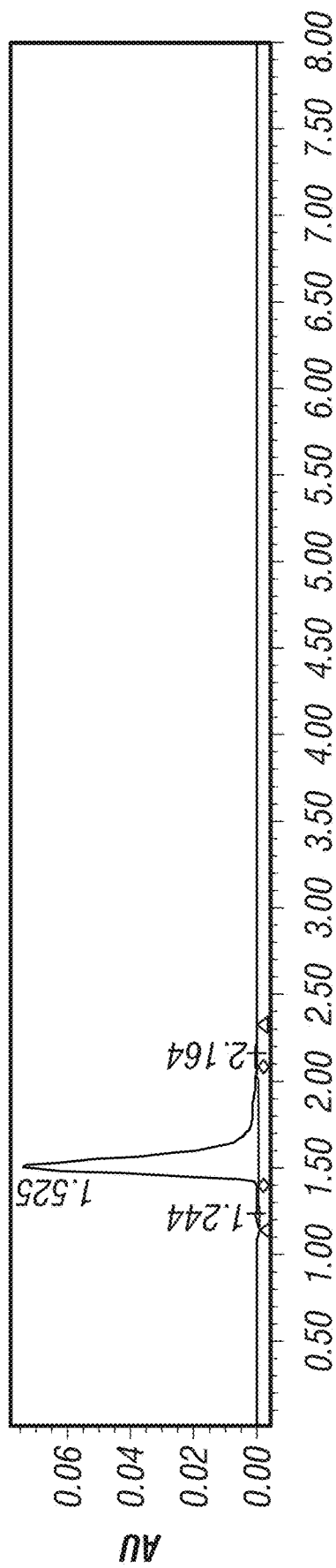
FIGS. 12A-D. Chromatograms of Itra and Posa from the HPLC as plasma alone, and plasma spiked with Itra and Posa in the stability studies.
Figure 12B:
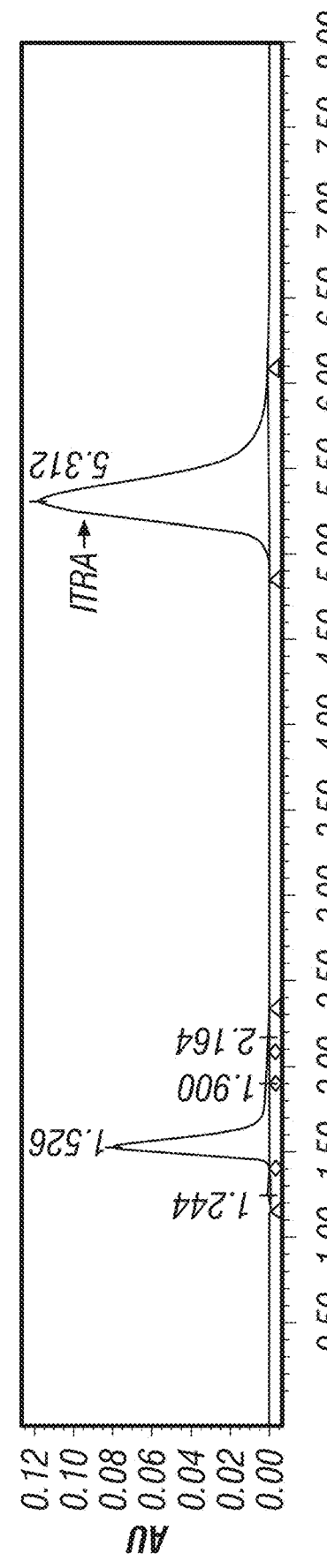
Figure 12C:
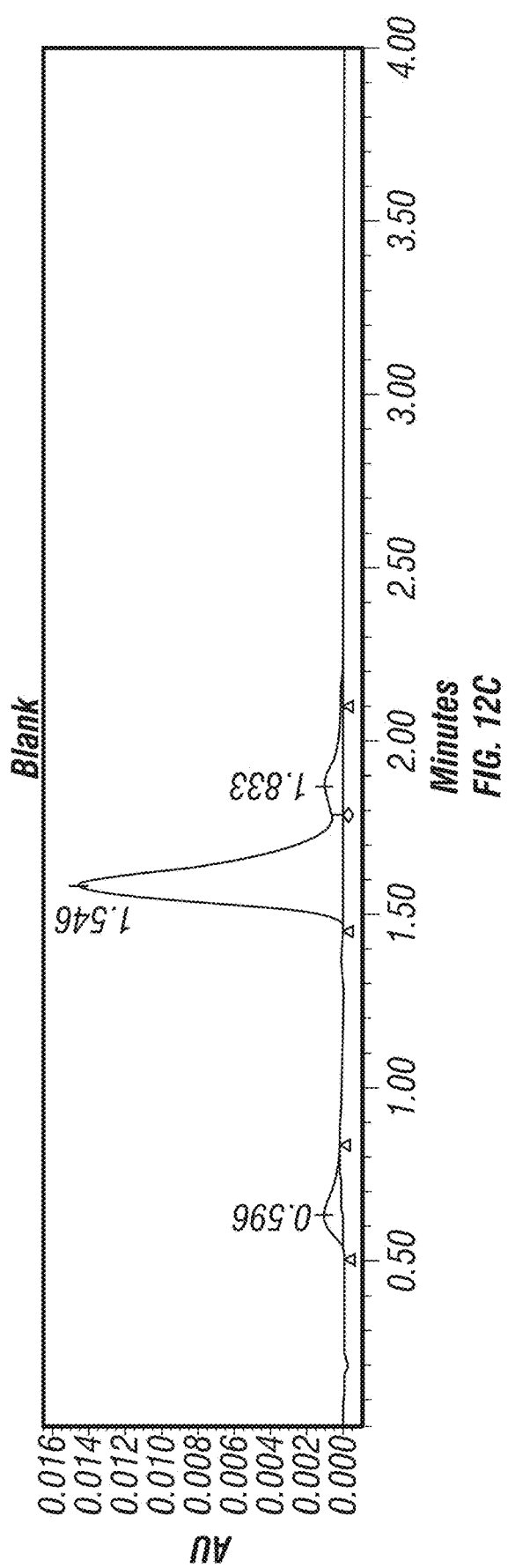
Figure 12D:
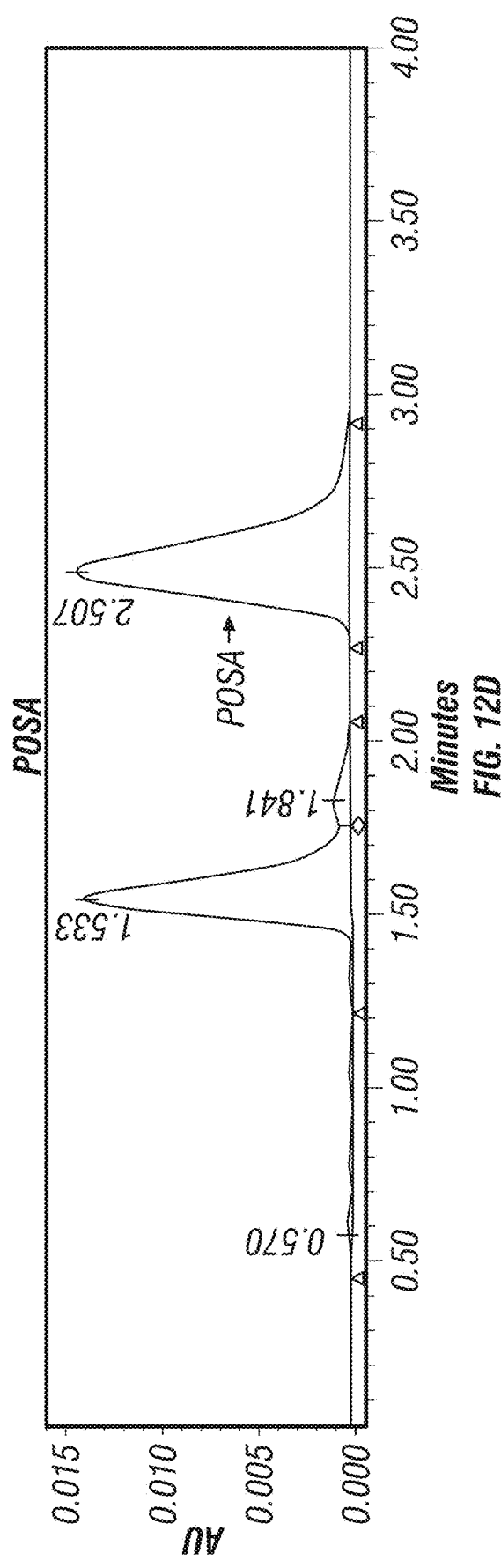

Azoles parenteral formulations—The azole antibiotics Itra and Posa were also formulated for parenteral infusion with VE-acetone/PEG/D5W, and the stability in VE-acetone/PEG at 4 mg/mL is displayed in FIG. 9. When subsequently diluted in D5W to a final concentration of 2 mg/mL they remained stable for at least 15 hours at RT (FIG. 10). These novel azole formulations retained full antifungal activity against selected strains of Aspergillus and Mucor spp. (FIG. 11 and Table 4).

TABLE 4

Two common mold pathogens under standard conditions read-out at 48 hr.

| Aspersillus- ATCC 90906 | | Mucorales (Rhizopus lab strain) | |
|---|---|---|---|
| Drug | MIC[1] | Drug | MIC |
| Itra/S[2] | 0.12 ug/ml | Itra/S | 0.3 ug/ml |
| Itra/D[3] | 0.12 ug/ml | Itra/D | 0.6 ug/ml |
| Posa/S[4] | 0.03 ug/ml | Posa/S | 0.06 ug/ml |
| Posa/D[5] | 0.03 ug/ml | Posa/D | 0.12 ug/ml |

[1]MIC = minimum inhibitory concentration,
[2]Itra/S = itraconazole in solvent system S,
[3]Itra/D = itraconazole in DMSO control.
[4]Posa/S = posaconazole in solvent system S,
[5]Posa/D = posaconazole in DMSO as a positive control solvent. Range of drug concentrations tested 32 ug/ml to 0.03 ug/ml.
Note:
Drug is prepared in each solvent system at the same initial concentration then diluted with media 1:50 to yield the concentration in the first well. All drugs are then further diluted by 2 fold serial dilution in media through well 11. Well twelve is left as a drug free negative growth control.

Additional Mold Species were tested similarly as in Table 4. The Aspergillus strain tested is new Aspergillus fumigatus [LAB-A from patient AF 040 511]. The Zygomycete tested is new Rhizomucor sp. [Lab-Z is derived from patient RM 041511]. The range of drug concentrations tested was 150, 25, 12, 6, 3, 1.5, 0.75, 0.38, 0.19, 0.09, 0.04, and 0 (control)

μg/mL. The susceptibility test was set-up using the standard method for filamentous fungi (CLSI, M38A standard). YeaStone media, Trek Diagnostics and Lot 152274SA—exp 2011-08 were used. *Aspergillus fumigatus* LAB-A inoculum was made 82% transmission in Saline. Zygomycete (Lab Z) inoculum was made 80% transmission in Saline. Itra was supplied at 1.5 mg/ml in vehicle. Posa was supplied at 2.0 mg/ml in vehicle. The Zygomycete was incubated at 33° C. for the first 24 hr to get growth established. The MIC results at 48 hrs were: *Aspergillus* LAB-A at 48 hr showed an MIC of 0.09 μg/ml for Itra in novel solvent; *Aspergillus* LAB-A at 48 hr showed an MIC of 0.04 μg/ml for Posa in novel solvent; Zygomycete LAB-Z at 48 hr showed an MIC of 0.2 μg/ml for Itra in novel solvent; Zygomycete LAB-Z at 48 hr showed an MIC of 0.04 μg/ml for Posa in novel solvent. Results showed that at 48 hr all growth controls were positive and equal as expected. There were no discrepant wells among 4 replicates at each drug concentration.

Example 2—Demonstration of In Vitro Solubility, Stability and Other Properties of One of the Novel Formulations In this example, stable Bu- and azole-(Posaconazole; Posa) formulations that would be suitable for human administration were evaluated. The chemical and physical stability of Bu and Posa in (a) composite solvent vehicle(s) were established. Further, the solubility of Bu and Posa in these composite solvent vehicles was established, using NS or D5W±20% PEG as the final diluent. This example also investigated the in vitro cytotoxic and antifungal properties of the respective formulations, including their hemolytic potential, cytotoxic/antifungal activity against human malignant cell lines and mold isolates, to establish that the solvent system is appropriate for parenteral administration as therapy for malignant or autoimmune diseases as well as against fungal/mold infections in humans and other mammals without loss of the therapeutic properties of the respective class of agents.

Solubility Studies

Bu and Posa were dissolved in various solvents at room temperature (RT) for 60 minutes, and centrifuged at >14,000 rpm for 1 min. The supernatant was then analyzed using HPLC to determine the maximum Bu/Posaconazole solubility. The Bu solubility differed markedly between different primary solvents (Table 1). A high equilibrium solubility (more than 15 mg/mL) was reached using DMA, DMSO, and acetone. In DMSO, Bu rapidly started degrading, confirming our concern that the sulfur group of DMSO would be reacting with Bu upon extended exposure. An organic solvent (e.g. acetone, or chloroform or DMA) was instead identified as a preferred primary solvent vehicle. Because of the toxicity concerns about using chloroform and/or DMA as the primary solvent (Dwivedi, 2002; VICH Steering Committee, 2010; The Food and Drug Administration, 2010; The Office of Environmental Health Hazard Assessment, 2010), the inventors continued the investigations with acetone as the preferred primary solvent. Busulfan could be stably dissolved (for at least 7 days at RT) in acetone and DMA, but once dissolved, the Bu-acetone mixture could not be diluted with an aqueous infusion fluid to allow parenteral administration without immediate precipitation. In a second step the inventors therefore utilized a modified cosolvency approach (Spiegel and Noseworthy, 1963; Yalkowsky et al., 1981).

The inventors hypothesized, that since Bu is very lipophilic/hydrophobic, the combination of acetone as a primary organic solvent combined with a secondary hydrophobic/ amphiphilic carrier would subject Bu to electrostatic attraction from the secondary polymeric carrier compound (e.g. PEG). The inventors further argued, that by gently removing the primary (volatile) organic solvent the inventors would create a micro-environment that sterically allows gradually increasing electrostatic attraction/binding of solubilized Bu in a complex with the carrier-molecule (e.g. PEG), and further, that this complex would be sufficiently stable to allow the drug-complex to be diluted in an aqueous infusion fluid without immediate chemical degradation or physical precipitation of the pharmaceutically active agent (in this example: Bu or Posa). The removal of acetone would be facilitated by adding a vacuum-extraction step that is facilitated by the high volatility/low boiling point of acetone. The inventors further hypothesized that since PEG is readily water-soluble, its amphiphilic properties would make it a suitable "carrier substance". The resulting drug/VE-acetone/PEG complex could then be diluted in water or an aqueous infusion fluid such as D5W or D10W or normal saline (NS) without precipitation, allowing its application in medical use through parenteral administration. The added benefit of the VE-acetone approach would be that the inventors could minimize the recipient's ultimate exposure to the primary organic solvent vehicle(s).

Stability Studies

It was initially important to describe short-term stability of the Bu/acetone/PEG mixture. This was necessary to determine if the vacuum-extraction step could be utilized without undue chemical degradation of Bu. The Bu (5 mg/mL) in acetone/PEG400 (1:2, v/v) was incubated at room temperature and quantified by HPLC after 0, 1, 2, 4, 8 and 24 hours. Second, the inventors confirmed that Bu would be stable in the VE-acetone/PEG/Bu complex. Therefore, to determine long-term stability Bu was dissolved in acetone (10 mg/mL), then mixed with PEG 400 (ratio 1:2, v/v). The acetone was extracted from the mixture under vacuum at room temperature (RT). The VE-acetone/PEG400/Bu was stored either at room temperature or 37° C. for 2 months in sealed tubes. Finally, Bu (1 mg/mL) in the final use formulation of VE-acetone/PEG 400/D5W (0:40:60, v/v/v), was incubated at room temperature and analyzed by HPLC at 0, 1, 2, 4, 8 and 15 hours to determine short-term stability. Triplicate samples were quantitatively analyzed with HPLC at all time points after appropriate dilution of the samples in the stability studies.

PEG-400, PG, NS, D5W, and 20% soybean lipid emulsion (Intralipid™) did not yield any significant concentrations of solubilized drug (<0.2 mg/mL after 60 min at RT). The latter were therefore not considered for further study as primary solvents.

Stability of the Various Bu Formulations

The physical and chemical stability of the various intended parenteral formulations were studied as follows, using the Bu/VE-acetone/PEG formulation as an example, and using D5W as the prototype final diluent.

Bu was dissolved at a concentration of about 10 mg/mL in acetone only or in VE-acetone/PEG (prototype stock solvent vehicle) and incubated at RT (22° C.) and at 37° C. The resulting Bu concentration was measured by HPLC in samples taken immediately after solubilization, then every few hours for 8 hours, and then at gradually increasing time intervals for up to 60 days.

In summary, the stability of Bu in the favored prototype solvent system (Bu/VE-acetone/PEG vehicle) was excellent: at 60 days ≥95% of Bu was still intact at RT, assayed by HPLC. From the available data it was deduced, that Bu and Posa in the described final solvent vehicle(s) is/are sufficiently stable for routine clinical use.

Hemolysis Studies In Vitro

The hemolytic potential of the final use-formulation should also be minimal, since the terminal use formulation/infusate contain Bu and PEG as the only significant solutes to be infused, i.e. this is basically D5W with a moderate amount of PEG (40%, v/v) as its main additive. The procedure of Parthasarathy et al. was used to examine the hemolytic potential of a few selected formulations, and the $LD_{50}$ values of the most optimal formulation was constructed as previously described (Parthasarathy et al., 1994). Briefly, heparinized blood was mixed with an equal volume of Alsever's solution (Alsever and Ainslie, 1941). This mixture was washed twice in PBS, and a 10% (volume per volume, v/v) erythrocyte/PBS solution was then prepared and mixed with increasing amounts of PEG (essentially the VE-acetone/PEG prototype vehicle) with or without addition of D5W and with or without Bu. The resulting mixtures were incubated for 4 hours at 37° C. At the end of the incubation, the cells were pelleted at 10,000×g in an Eppendorf microcentrifuge, and after washing twice in NS, the pellet was resuspended and lysed using distilled water. The release of hemoglobin in the supernatant (i.e., hemolysis) was determined spectrophotometrically at a wavelength of 550 nm. Maximum lysis was measured against a reference erythrocyte solution that had been lysed by hypotonic shock. The hemolytic potential of the vehicle and the complete final use-formulation (Bu/VE-acetone/PEG/D5W) was evaluated as described (Parthasarathy et al., 1984). The results were plotted as the fraction of intact erythrocytes versus concentration (total volume percent) of the solvent vehicle. The total volume percent was defined as the volume percent of the solvent system in the mixture after addition of the erythrocyte suspension. This was done to simulate the dilution of the drug formulation in the blood stream after parenteral administration. Intact, healthy erythrocytes were defined as those capable of retaining their hemoglobin intracellularly after mixture with the solvent vehicle with or without Bu.

Figure 4:
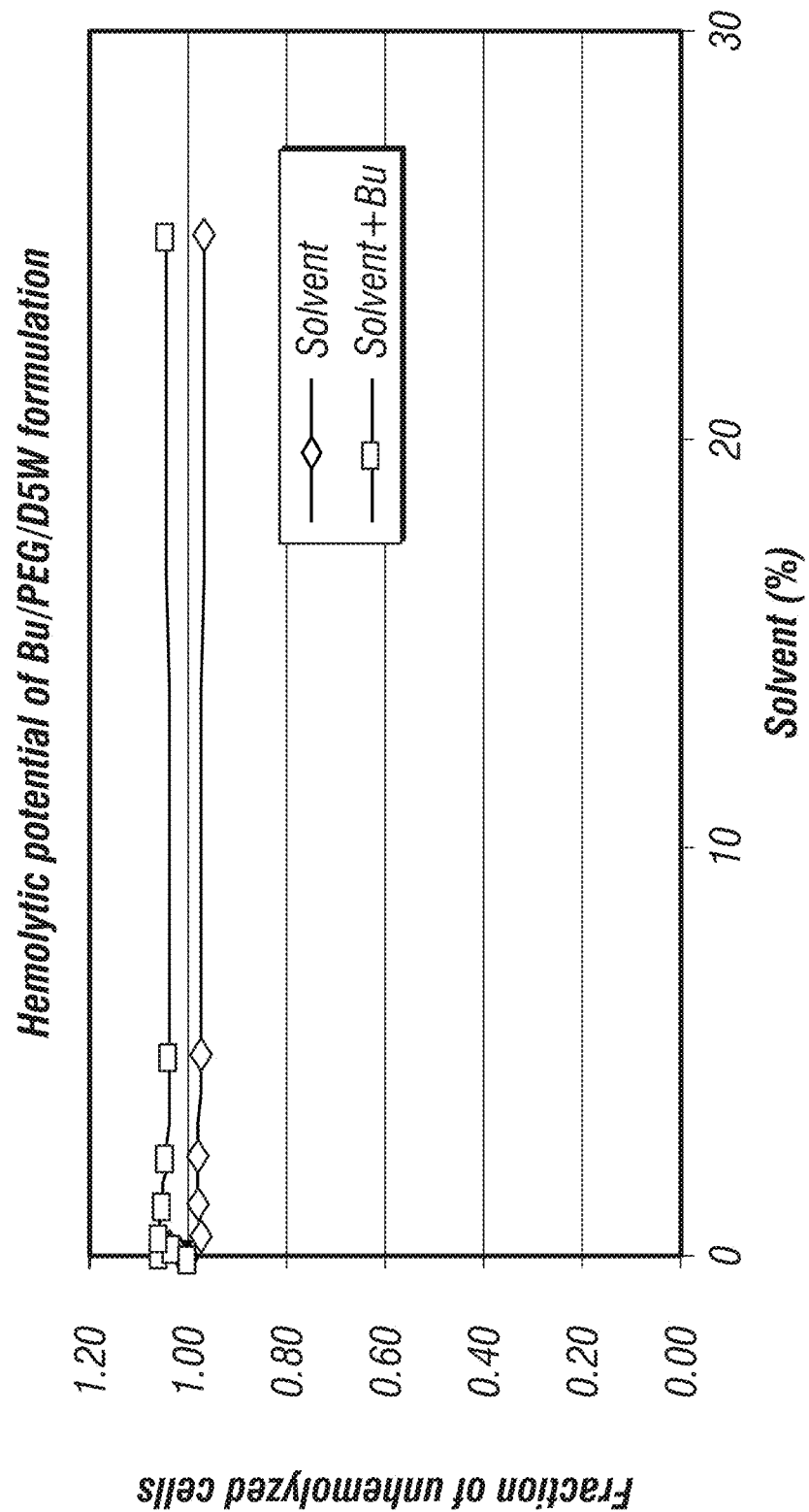
FIG. 4. A graph showing the hemolytic potential of the use-formulation of Bu/VE-acetone/PEG/D5W, and the same formulation ("solvent") without busulfan. The x-axis shows the solvent content in volume percent (v/v). The y-axis shows the calculated fraction of unhemolyzed red blood cells.

The final use-formulation showed a negligible capability for inducing hemolysis when the complete use-vehicle with or without Bu was used. The Bu-dependent lysis barely exceeded background levels, also for drug concentrations of 100 µg/mL or more, which is many times higher than the highest expected concentration in a clinical situation with once daily Bu-administration as a three-hour infusion (expected peak-concentrations of less than 5 µg/mL) (Russell et al., 2002; De Lima et al., 2004; Madden et al., 2007). The Bu-specific hemolysis was highly reproducible between different assays. The data derived from repeated experiments with the complete final use-solvent vehicle±Bu are summarized in FIG. 4, which graphically illustrates the (lack of) hemolytic potential of the use formulation of VE-acetone/PEG/D5W with Bu, and the same formulation ("solvent" alone) without Bu, as indicated in the figure. The solvent alone curve also demonstrates the exceedingly low hemolytic potential when the solvent is mixed with alternative agents including, but not limited to, azole compounds. The x-axis shows the concentration in µg/ml. The y-axis shows the percent hemolysis. Finally, there was no sign of hemolysis after injection of 10 mg/kg in vivo, when urine samples were evaluated up to 4 hours in parallel with obtaining blood samples for plasma concentration assays in the mouse experiments.

In conclusion, the Bu/VE-acetone/PEG/D5W complete infusion fluid had very low hemolytic potential and should be completely safe for human parenteral (intravascular as well as intrathecal, or intracavitary) administration.

In Vitro Cytotoxicity of Busulfan.

The cytotoxic potential of the selected preferred solvent systems with and without Bu was determined against the human myeloid leukemia cell lines KBM-3 and KBM-7/B5, as well as the OCI-AML3 (Andersson et al., 1993; Andersson et al., 1987; Andersson et al., 1995; Wang et al., 1991). Briefly, continuously growing cells were exposed to drug, and then pelleted, after which they were resuspended in complete cell culture medium at $2\times10^5$/mL and aliquoted (20,000/well) in 96-well plates, incubated at 37° C. for 4 days, and analyzed by the MTT assay (Mosmann, 1983). Graphical analyses including calculations of $IC_{50}$ and charting of survival were done using Prism 4 (GraphPad Software, Inc., San Diego, Calif.). Cells exposed in parallel to solvent system and medium alone served as negative controls, and cells exposed to DMA (final concentration 0.08% v/v) served as a positive control for a comparison of cytotoxic action with the DMA-Bu formulation.

Figure 5B:
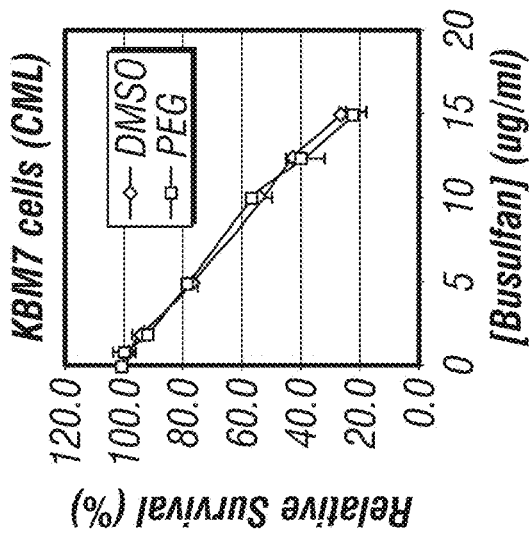
FIGS. 5A-C. Graph depicting the cytotoxic activity of busulfan in the PEG/D5Wclinical use-formulation against the human cell lines KBM-3 (A) (Andersson et al., 1992) and KBM-7 (B) (Andersson et al., 1987; Andersson et al., 1995), assessed in vitro with the MTT assay. The X-axis shows the Bu concentration in µg/mL, the Y-axis shows the calculated cell survival fraction. As a positive control served cells exposed in parallel to busulfan in DMSO. (C) shows the cytotoxic activity of DMA alone in the MTT assay at the highest concentration achieved when DMA-Bu was used as a positive control in the cell lines KBM3, KBM7, B5/Bu250-6, and in the OCI-AML3 (Wang et al., 1991). The latter findings correspond to a concentration which can be achieved when DMA-Bu is used for pre-HSCT therapy with repeated dosing over 3-4 days.
Figure 5C:
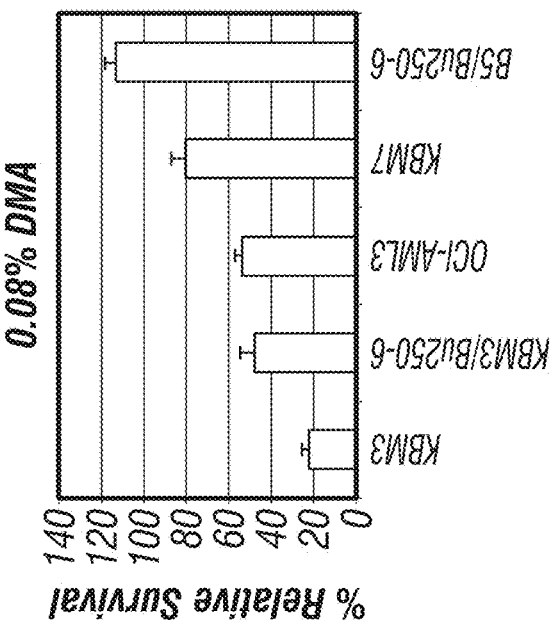
Figure 5A:
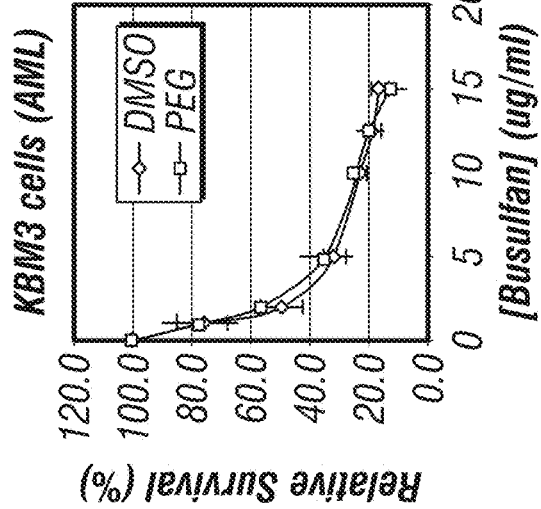
Figure 6:
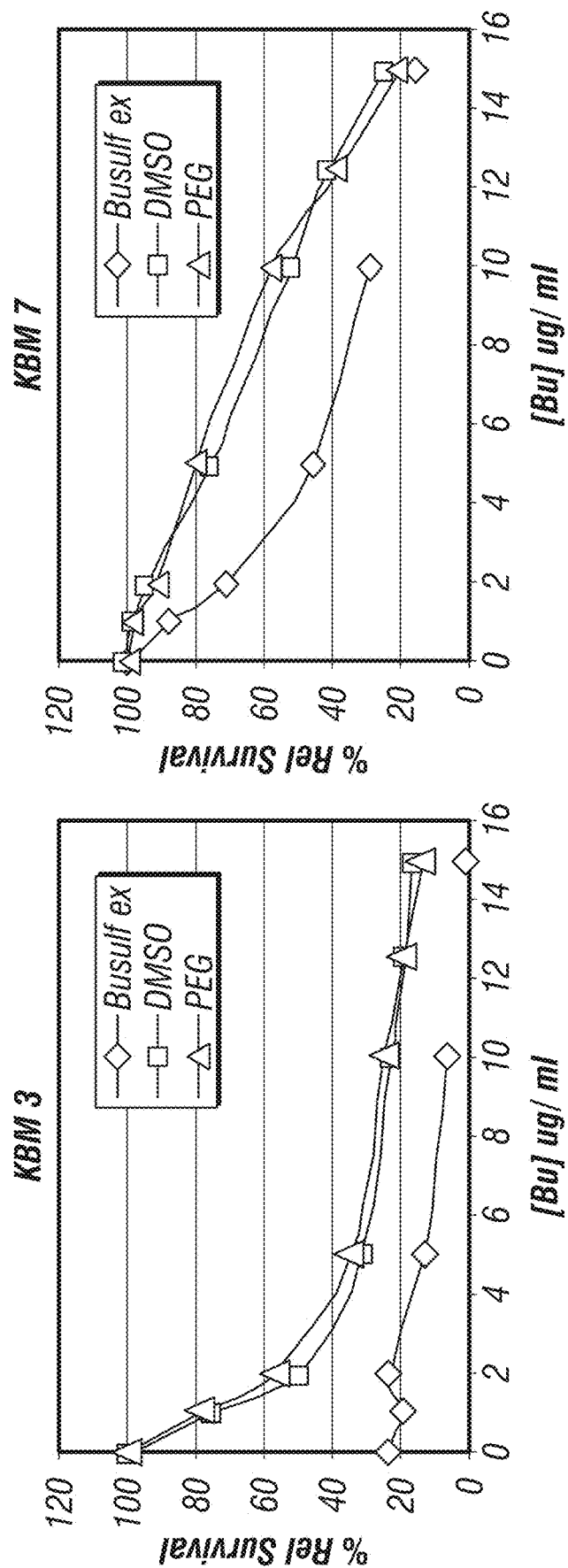
FIG. 6. Sensitivity of three of the cell lines to Bu in DMSO and in the new formulation relative to the cytotoxic effects reached with the DMA-Bu formulation. Of note is the significantly higher toxicity/lower survival fraction at increasing Bu concentrations with the DMA-Bu formulation, and in particular in the KBM-3 cell line the contribution of DMA to overall cytotoxicity is significant. It appears from the data that the effects of DMA and Bu are synergistic rather than additive (Chou and Talalay, 1984). In contrast, the current novel formulation and the DMSO-Bu reference formulation exert virtually identical cytotoxic effects in all tested cell lines, and there is no added toxic effect(s) from the solvent vehicle.
Figure 6:
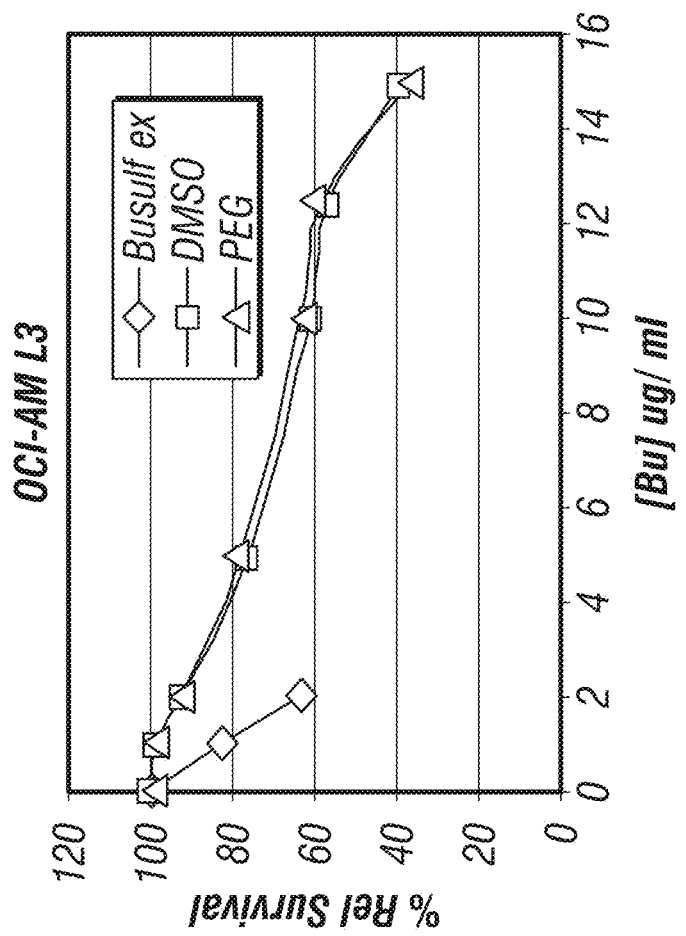

The examined solvent system VE-acetone/PEG did not exhibit any detectable toxicity in the concentrations achieved at the highest tested Bu concentrations against any of the cell lines used in these experiments (negative control, data not shown). When the final Bu-use-formulation was added in increasing concentrations to the cells, concentration-dependent cytotoxicity was apparent (FIG. 5). Busulfan retained full cytotoxic activity in the use-formulation when compared with cells exposed in parallel to Bu dissolved in DMSO (positive control). Interestingly, in these experiments the DMA-Bu formulation exerted significantly higher cytotoxic activity (FIG. 6); this activity was higher than could be accounted for by additive cytotoxicity and indicates pronounced synergy between Bu and DMA in all examined cell lines (Chou and Talalay, 1984). This observation triggered our subsequent examination of whether the DMA by itself exerted significant and measurable cytotoxic activity. The DMA-solvent was highly toxic against both the AML cell lines KBM-3 and OCI-AML3, and it also had significant cytotoxic activity against the CIVIL line KBM-7 and its Bu-resistant subline B5/Bu250-6, FIG. 5 (c). It is conceivable, that such (unpredictable) DMA-related toxicity could in a significant way contribute to the clinical risk of receiving the DMA-Bu formulation, since normal organ-effects of DMA are likely to parallel what is seen in the cell lines. This supposition is further supported by both the occupational hazards literature and by the available toxicity data from the evaluation of DMA as an anti-cancer compound (Choi et al., 2001; Weiss et al., 1962a; Weiss et al., 1962b), as well as by the investigation of DMA-related fetal toxicity in rodents and logomorphs (Malley et al., 1995; Kennedy, 1986; Klimisch and Hellwig, 2000; Okuda et al., 2006; Valentine et al., 1997; Kennedy, 2001). Finally, a previous investigation of DMA-Bu in vitro indicated synergistic cytotoxicity between DMA and Bu in human leukemia cells (Sadeghi et al., 1999).

In Vitro Antifungal Activity of Itraconazole and Posaconazole.

The antimicrobial/antifungal potential of selected solvent systems with and without Itra was determined against several isolates of both yeast and different mold species. The findings confirm that the Itra, and Posa retain antifungal activity (Table 4). The variant solvent systems are in themselves without any effect on mold- and yeast-proliferation (FIG. 11).

Yeasts

Tested drug dilution range 38 µg/mL to 0.03 µg/mL

| Candida cruzei (ATCC strain 6258) | | Candida parapsilosis | |
|---|---|---|---|
| Drug | MIC | Drug | MIC |
| Itra-s | 0.07 | Itra-s | 0.03 |
| Itra* | 0.15 | Itra* | 0.07 |

Itra* is a control lot of Itra dissolved in DMSO as a positive control

Itra-s is the Itra dissolved in the new formulation system.

Growth controls (negative controls, fungae grown in medium only) displayed excellent growth. Candida growth in medium with solvent vehicle without drug also displayed excellent growth.

B. Molds

Two hyaline molds were tested with a standard read out at 48 hrs:

Tested drug range: 75 µg/mL to 0.07 µg/mL

| Aspergillus fumigatus (ATCC strain 90906) | | Aspergillus fumigatus (Clinical Lab isolate) | |
|---|---|---|---|
| Drug | MIC | Drug | MIC |
| Itra | 1.2 | Itra | 0.6 |
| Itra* | 0.6 | Itra* | 0.3 |

For description of Itra-s and Itra*, see above.

Extended Mold Testing

To further determine the antifungal activity of the compounds in the new formulation systems the inventors investigated the efficacy of the various agents against additional strains of mucor and Aspergillus (The Rhizomucor was a clinical isolate from a patient isolate) and the Aspergillus fumigatus (ATCC strain 90906) used was as previously described. Again, the susceptibility tests were set-up using the standardized test method (CLSI M38A). The used drugs were provided in the described final use-formulation VE-acetone/PEG/D5W. All drugs were diluted in RPMI-Mops medium: YeastOne, Sensititer (Lot 151416SA, expiration date in 2011).

As before two different molds were tested with a standard read out at 48 hr:

Drug dilution range 75 µg/mL to 0.07 µg/mL.

| Aspergillus fumigatus (ATCC strain 90906) | | Zygomycete (Clinical Lab isolate, MDACC) | |
|---|---|---|---|
| Drug | MIC | Drug | MIC |
| Itra | 1.2 | Itra | 2.5 |
| Itra* | 0.3 | Itra* | 2.5 |

All mold growth controls, including controls with solvent vehicle(s) without added azole drug, grew without inhibition as described before.
For description of Itra*, see above.

Briefly, susceptibility tests were set-up using a standardized methodology (CLSI M38A). Drugs were diluted into RPMI-Mops medium (Yeast One Broth (Sensititer, product Y3462, Trek Diagnostic Systems, Cleveland, Ohio) Sensititer Lot number 151416SA—expiration date 2011). Two different strains of yeast were tested, the standardized evaluation/read out was performed at 24 hours after the start of each culture. The tests were repeated twice and all MIC values (minimum inhibitory concentration) determined as an average of the two experiments.

Example 3—Quantitative Busulfan Analysis in Plasma and Pharmacology of IV Bu

This example demonstrates that Bu and azole antifungal antibiotics in (a) preferred solvent vehicle(s) and mixed with blood plasma may be recovered as native/intact drug using quantitative extraction technology and HPLC assay, and that the drugs remain stable in a cytotoxic/fungistatic concentration range for several hours after administration. It further shows that the preliminary plasma pharmacokinetics after parenteral administration of a preferred Bu formulation in mice conforms to what can be expected, based on the published pharmacology of oral and IV Bu (Slattery et al., 1997; Dix et al., 1996; Hassan et al., 2000; Hassan et al., 1989; Bhagwatwar et al., 1996; Andersson et al., 2000; Andersson et al., 2002; Russell et al., 2002; De Lima et al., 2004; Madden et al., 2007; Busulfex, 2009).

Quantitative Extraction of Busulfan in Plasma

One mL of human plasma was mixed with various amounts of the reformulated Bu (<3% of the final volume) to yield a drug concentration range from 1 to 10 µg/mL (the use-formulation Bu/VE-acetone/PEG/D5W was made of the prototype solvent vehicle and D5W, having a Bu concentration 1.0 mg/mL). The drug was then extracted from the plasma samples and analyzed by HPLC as described in Example 1. Briefly, 1 volume of blood plasma was mixed with 1 volume of acetonitrile and after vortex-mixing the samples were centrifuged to precipitate the plasma proteins that would otherwise produce interfering peaks in the chromatograms. The supernatant was then derivatized with DDTC and extracted with ethyl acetate. After evaporation-reconstitution the Bu was assayed by HPLC using fluorescence detection at 254 nm as described above. The Bu retention time in this system was 2.5-3.0 min when using the Nova-Pak column (see Example 1). The Bu recovery from plasma spiked at 10 µg/mL was calculated to be approximately 90-100% (data on file). The assay was linear in the interval from about 25 ng/mL to at least 20 µg/mL, with a detection limit of about 5-10 ng/mL when 100 µL was injected into the chromatograph. A standard curve was routinely prepared in the range from 0.10 µg/mL to 10 µg/mL for the pharmacology experiment (not shown), and a good linear correlation (r=0.99) was obtained between the actual plasma Bu concentrations and the measured AUC values.

Parenteral Busulfan: Experimental Protocol in Mice.

Swiss Webster mice with a body weight of 25-30 g were used for the in vivo pharmacology experiments (Harlan-Sprague-Dawley, Houston, Tex.). The animals were allowed a minimum of 3-4 days after arrival to acclimatize to the new environment and allowed free access to commercial feed and hyperchlorinated, reverse-osmosis purified water prior to and during the experimentation period. The animal-housing facilities meet the requirements of the USDA, NIH, and DHHS.

Busulfan at a dose of 10 mg/kg BW was used as an appropriate and representative single dose that could be administered as a slow IV bolus injection over 3-4 min.

The Bu was formulated in the prototype VE-acetone/PEG vehicle to a stock concentration of about 10 mg/mL and then diluted with D5W to 1 mg/mL and 2 mg/mL (in repeated experiments) so the total dose of 10 mg/kg could be injected in a volume of about 250 µL and 125 µL, respectively, in a tail vein. The Bu concentrations of the final use-formulation were confirmed by HPLC prior to administration.

No anticonvulsant premedication was used in the animals in these experiments to avoid the possible induction of microsomal liver enzymes that could modify Bu metabolism. For the same reason the animals were unanesthetized during the drug injection, only physically restrained.

Blood samples (0.5-1.0 mL) were procured through cardiac puncture under Isoflurane-induced general anesthesia. These samples were drawn in preheparinized tubes at selected time points prior to the drug infusion ("blank"), and from 5 min to 4 hours after drug injection for determination of Bu concentrations. The blood was centrifuged at 1,000×g for 10 min, and plasma was removed and stored at −80° C. until extracted and assayed by HPLC.

Busulfan in Plasma and IV Drug Pharmacology Results

Figure 7A:
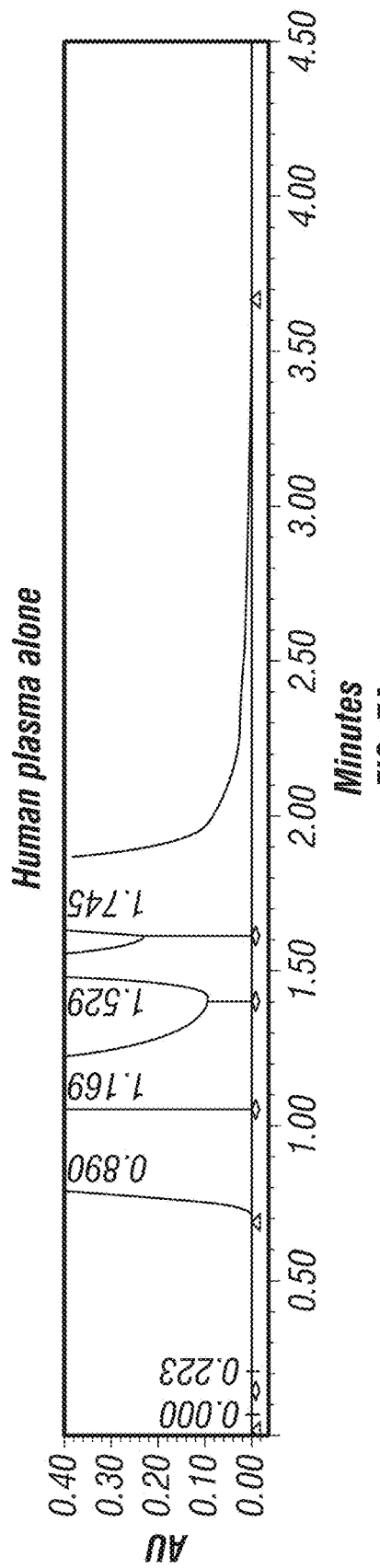
FIGS. 7A-C. Chromatograms of plasma samples extracted as described under Example 3 and then analyzed with HPLC. (A) The upper panel shows a blank plasma sample, (B) the middle panel shows a human plasma sample spiked with busulfan in the new formulation (prototype use-solvent vehicle of Bu/VE-acetone/PEG/D5W) to 10 µg/mL, with a retention time of approximately 2.8 minutes. (C) The lower panel shows a chromatogram from the pharmacology study, where a mouse was injected with busulfan at 10 mg/kg. The chromatogram was from a sample drawn 20 minutes after drug injection.
Figure 7B:
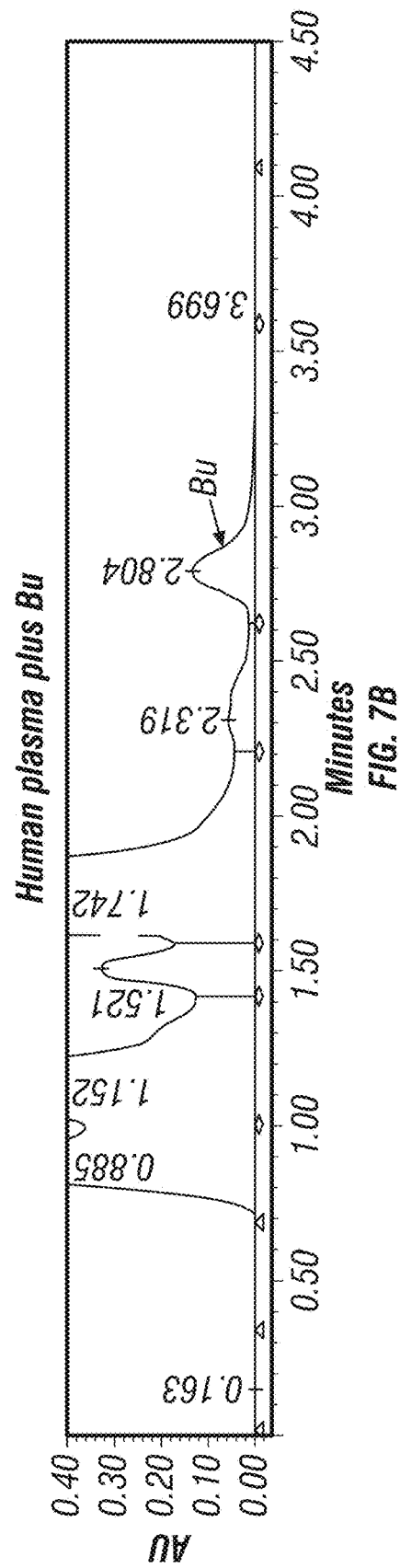
Figure 7C:
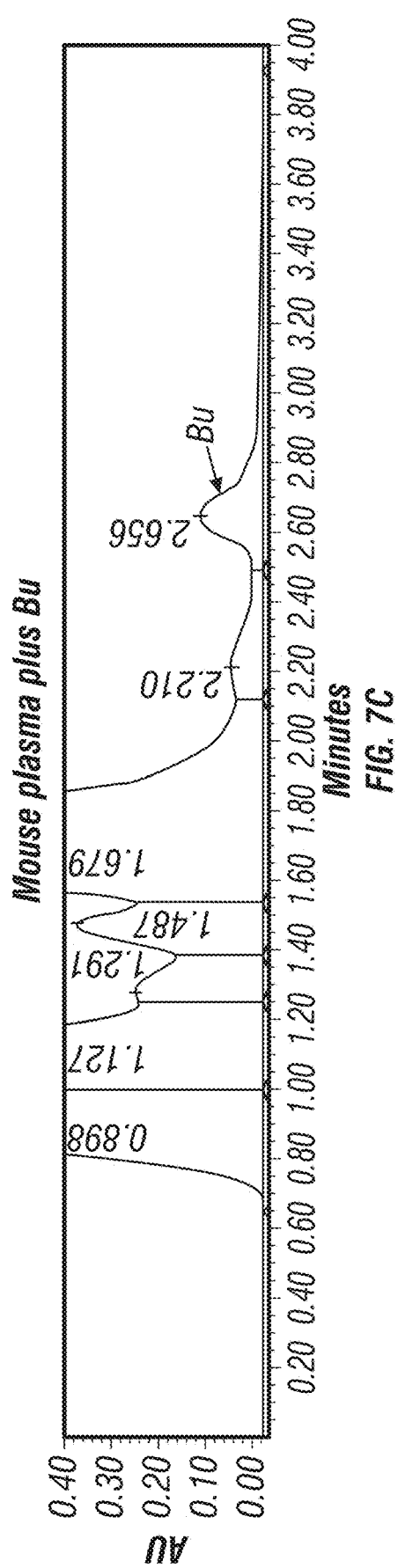

Authentic chromatograms from (a), Bu-spiked plasma and (b) one plasma sample obtained from the current pharmacokinetic study are shown in FIG. 7. FIG. 7 shows a plasma sample spiked with Bu in the new prototype formulation to 10 µg/mL, and the figure also shows a chromatogram from the pharmacology study, where mice were injected with Bu at 10 mg/kg. The latter chromatogram was from a sample drawn 20 minutes after drug injection.

Figure 8:
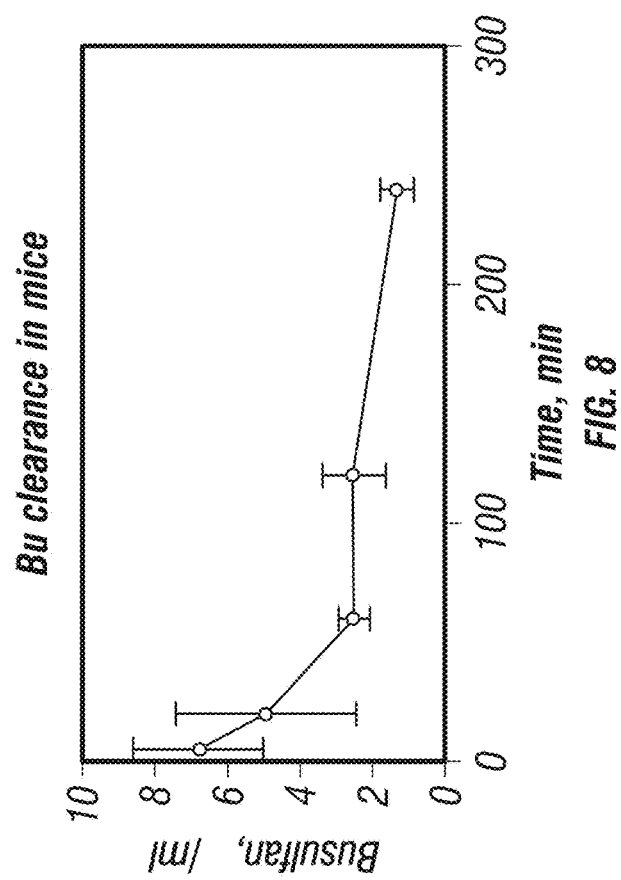
FIG. 8. Graph showing the change in plasma concentration over 4 hours after injection of 10 mg/kg of busulfan in mice. The X-axis shows the time after dosing in hours. The Y-axis shows the concentration of busulfan in µg/mL plasma. The apparent busulfan half-life is in the approximate range of 2.5-3.5 hours under the conditions used with this new formulation, similar to what has previously been reported for the DMA-Bu in rats and in humans (Bhagwatwar et al., 1996; Russell et al., 2002; De Lima et al., 2004 Madden et al., 2007).

The resulting data illustrate that the novel Bu solvent vehicle(s) give(s) detectable, cytotoxic Bu plasma concentrations after injection of 10 mg/kg BW. FIG. 8 is a graph showing the change in plasma concentration over time after a Bu injection of 10 mg/kg injected IV over approximately 3-4 min. The x-axis shows the time after injection in minutes. The y-axis shows the Bu concentration in µg/mL plasma, with an apparent terminal Bu half-life in the range of 2.5-3.5 hours. All injections were well tolerated, and no visible adverse effects were encountered during the acute 4-hour observation period.

In summary, the data demonstrate that the novel pharmaceutically acceptable, stable formulations of Bu in the invention can be safely utilized for parenteral administration. A preferred solvent vehicle is physiologically compatible with intravascular administration and was used to demonstrate that the injection of Bu in this solvent vehicle was well accepted and had insignificant acute solvent system toxicity in a mouse model. The IV injection of this formulation in mice at 10 mg/kg BW yielded Bu plasma concentrations that for several hours remained in the cytotoxic range, based on comparisons with our in vitro cytotoxicity experiments and in comparison with data obtained from several earlier studies using either oral Bu (Slattery et al., 1997; Dix et al., 1996; Hassan et al., 2000; Hassan et al., 1989; Vassal, 1994; Hassan et al., 1994), or DMA-Bu (Andersson et al., 2000; Andersson et al., 2002; Russell et al., 2002; De Lima et al., 2004; Madden et al., 2007).

The data obtained with the final use-formulation VE-acetone/PEG/D5W conclusively prove that it is now feasible to introduce Bu for parenteral administration in clinical therapy of malignant and autoimmune diseases without the added toxicity of DMA used as an excipient component of the solvent vehicle. This can be expected to result in greatly improved safety of the Bu-based cytotoxic treatment program. These results now finally also give a reasonable expectation of insignificant normal organ toxicity from the solvent vehicle. In particular, it is possible that the serious hepato-renal and central nervous system toxicity that is still occasionally encountered with the currently available DMA-Bu formulation may be avoided with this new solvent vehicle(s).

The novel solvent systems will significantly improve the clinical safety of Bu-based therapy, and make it possible to optimize the use of this important drug in the treatment of cancer and autoimmune disorders. In particular, embodiments of the invention may be utilized in conditioning of patients undergoing combination chemotherapy preceding HSCT.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

ABBREVIATIONS USED IN THIS APPLICATION

AAALAC—Association for the Assessment and Accreditation of Laboratory Animal Care International ALT—Alanine-Amino-Transferase.

Alsever's solution—Standardized solution of citric acid in Sodium Chloride (Alsever and Ainslie, 1941)

AML—Acute myeloid leukemia.

AST—Aspartate-Amino-Transferase.

ATCC—American Tissue Culture Collection, Rockville, Md.

ATG—Antithymocyte globulin.

AUC—area under the curve, term used to denote the actual measured area of a peak in a chromatogram, and also for the area under the plasma concentration vs. time curve over several hours after administration of a drug to an animal or human being.

BSA—Body surface area.

Bu—1,4-butanediol dimethanesulfonate, Butane-1,4-diyl dimetanesulfonate; $C_6H_{14}O_6S_2$, Busulfan BW—Body weight.

Clo—Clofarabine.

CLSI M38A standard—Clinical Laboratory Standards Institute M38A (Standardized Susceptibility testing for filamentous molds).

CML—Chronic myelogenous leukemia.

Cy—Cyclophosphamide.

D5W—Dextrose, 5% in water

D10W—Dextrose, 10% in water

DMA—N,N-Dimethylacetamide.

DMF—Dimethylformamide.

DMSO—Dimethylsulfoxide.

DNA—Deoxyribonucleic acid.

DHHS—Department of Health and Human Services.

EtOH—Ethanol.

FBS—Fetal bovine serum.

FDA—United States Food and Drug Administration.

Flu—Fludarabine.

GSH—Glutathione.

GST—Glutathione-S-Transferase.

HPLC—High-pressure liquid chromatography.

HSCT—Hemopoietic stem cell transplantation.

IMDM—Iscove's modified Dulbecco medium (GIBCO, Grand Island, N.Y., N.Y.).

Intralipid™—Brand name of an aqueous lipid emulsion made primarily from soybean oil and marketed for parenteral nutrition available from Baxter Healthcare, Inc. USA.

IV—Intravenous.

KBM-3—Human myeloid leukemia cell line designated KBM-3.

KBM-3/Bu2506—subline of the KBM-3 line resistant to busulfan.

KBM-7 and KBM-7/B5—Human myeloid leukemia cell line designated KBM-7, and a cloned subline thereof designated KBM-7/B5.

$LD_{50}$—The concentration or dose that results in 50% lethality or destruction of a population.

Liposyn™—Brand name of an aqueous lipid emulsion made primarily from soybean oil and marketed for parenteral nutrition available from Abbott (Abbott Park, Ill.).

MDACC—University of Texas MD Anderson Cancer Center, Houston, Tex.

MDS—Myelodysplastic syndrome.

MeOH—Methanol.

MIC—term denoting the minimum inhibitory concentration of bacterial and fungal growth for an antibiotic when tested in a standardized in vitro system for assessment of sensitivity to said antibiotic.

MTT—3, [4,5-Dimethylthiazol-2-yl]2,5-diphenyltetrazolium-bromide.

NCI—National Cancer Institute.

$NH_4$-acetate—Ammonium acetate.

NIH—National Institute of Health.

NS—Normal saline (150 mM NaCl).

OCI-AML3—Human myeloid leukemia cell line.

PBS—Phosphate-buffered saline (Dulbecco's formulation, pH 7.4).

PEG, and PEG400—Polyethylene glycol(-400).

PG—Propylene glycol.

PTFE—Polytetrafluoroethylene (filters), Teflon.™

RT—Room temperature (about 22° C.).

SDS—Sodium dodecylsulphate.

TBI—Total body irradiation.

TRM—Treatment-related mortality.

USDA—US Department of Agriculture.

UV—ultraviolet.

VE-acetone—see below

VE-acetone/PEG—PEG that after mixing with acetone subsequently has had the (volatile) acetone extracted/evaporated under vacuum, i.e. "Vacuum-Extracted, or Vacuum-Evaporated".

VOD—Veno-occlusive disease.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary, procedural or other details supplementary to those set forth herein, are specifically incorporated herein by reference.

U.S. Pat. No. 5,430,057
U.S. Pat. No. 5,559,148
Aggarwal et al., Biol. Blood Marrow Transplant., 12:770-777, 2006.
Alsever and Ainslie, State Med. J., 41:126-135, 1941.
Andersson et al., Biol. Blood Marrow Transplant., 14:672-684, 2008.
Andersson et al., Biol. Blood Marrow Transplant., 8:145-154, 2002.
Andersson et al., Bone Marrow Transplant., 6:548-554, 2000.
Andersson et al., Cancer Genetics Cytogenet., 24:335-343, 1987.
Andersson et al., Exp. Hematol., 20:361-367, 1992.
Andersson et al., Leukemia, 9:2100-2108, 1995.
Baddley et al., J. Clin. Microbiol., 47(10):3271-3275, 2009.
Bearman, Blood, 85:3005-3020, 1995.
Benet and Sheiner, In: Goodman and Gilman's The Pharmacological Basis of Therapeutics, Goodman et al. (Eds.), 7th Ed., MacMillan Publishing Co. N.Y., P. 8, 1985.
Bhagwatwar et al., Cancer Chemother. Pharmacol., 37:401-408, 1996.
Blaise et al., Blood, 79:2578-2582, 1992.
Boothe et al., Am. J. Vet. Res., 58(8):872-77, 1997.
Bredeson et al., Biol. Blood Marrow Transplant., 14:993-1003, 2008.
Busulfex, (IV Busulfan) for injection, package insert, Otsuka America Pharmaceuticals, Inc., 2009.
Campo et al., J. Infect. Dis., 60(5):331-337, 2010.
Carrillo-Munoz et al., J. Antimicrobial. Chemoth., 55(3): 317-9, 2005.
Chae et al., Bone Marrow Transplant., 40:541-547, 2007.
Chan et al., Bone Marrow Transplant., 29:963-965, 2002.
Chen et al., Curr. Opin. Pharmacol., 10(5):522-530, 2010.
Choi et al., Korean J. Occup. Environ. Med., 13:164-170, 2001.
Chou et al., Adv. Enzyme Regul., 22:27-55, 1984.
Chow et al., J. Chromatogr. B, 704:277-288, 1997.
Ciurea et al., Biol. Blood Marrow Transplant., 15(5):523-536, 2009.
Courtney et al., Antimicrob. Agents Chemother., 47:2788-2795, 2003.
Courtney et al., Antimicrobial. Agents Chemo., 47(9):2788-2795, 2003.
Davis et al., Am. J. Vet. Res., 66(10):1694-1701, 2005.
De Lima et al., Blood, 104:857-864, 2004.
Dean et al., Br. J. Haematol., 148:226-234, 2010.
Deeg et al., Biol. Blood Marrow Transplant., 5:316-321, 1999.
DeLeve et al., Semin. Liver Dis., 22:27-42, 2002.
Devergie et al., Blood, 85:2263-2268, 1995.
Dix et al., Bone Marrow Transplant., 17:225-230, 1996.
Dodds-Ashley et al., Drugs of Today, 41(6):393-400, 2005.
Dodds-Ashley, Pharmacotherapy, 30(8):842-854, 2010.
Dutkiewicz and Hage, Proc. Am. Thorac. Soc., 7(3):204-209, 2010.
Dwivedi, Pharmaceutical Technol. Europe, 42-46, 2002.
Evans, Proc. Am. Thorac. Soc., 7(3):197-203, 2010.
Evensen, et al., Thromb. Diath. Haemorrh., 19:570-577, 1968.

Fortner et al., *Am. J. Hosp. Pharm.*, 32:582-84, 1975.
Glockner and Karthaus, *Mycoses.* 2010 (e-pub.)
Greer, *Baylor Univ. Med. Center Proc.*, 20:188-196, 2007.
Grigg et al., *Ann. Intern. Med.*, 111:1049-1050, 1989.
Grochow et al., *Cancer Chemother. Pharmacol.*, 25:55-61, 1989.
Grochow, *Semin. Oncol.*, 3:20 (Suppl 4):18-25, 1993.
Groll and Walsh, *Mycoses*, 49 (Suppl 1):7-16, 2006.
Haddow and Timmis, *Lancet.*, 31:207-208, 1953.
Hartman et al., *Bone Marrow Transplant.*, 22:439-443, 1998.
Hassan et al., *Blood*, 84:2144-2150, 1994.
Hassan et al., *Bone Marrow Transplant.*, 25:915-924, 2000.
Hassan et al., *Cancer Chemother. Pharmacol.*, 33:181-186, 1993.
Hassan et al., *Eur. J. Clin. Pharmacol.*, 36:525-530, 1989.
Hempel et al., *J. Clin. Oncol.*, 25:1772-1778, 2007.
Hicheri et al., *Expert Rev. Anti. Infect. Ther.*, 8(9):1049-1060, 2010.
Hoffman et al., In: *Hematology. Basic principles and practice*, Churchill Livingstone Inc., N.Y.,
Philadelphia, 1991.
Hsu et al., *Infect. Dis. Clin. North Am.*, 24(3):557-577, 2010.
Ito et al., *Leuk. Lymphoma*, 51(9):1623-1631, 2010.
Jang et al., *Clin. Pharmacol. Ther.*, 88(1):115-119, 2010.
Jones et al., *Transplantation*, 44:778-783, 1987.
Kashyap et al., *Biol. Blood Marrow Transplant.*, 8:493-500, 2002.
Kennedy, *Crit. Rev. Toxicol.*, 31:139-222, 2001.
Kennedy, *Drug Chem. Toxicol.*, 9:147-170, 1986.
Kim et al., *Haematologica.*, 90:285-286, 2005.
Kim et al., *Mycoses.*, 54:e301-312, 2011.
Klimisch and Hellwig, *Human Experim. Toxicol.*, 19:676-683, 2000.
Kobayashi et al., *Bone Marrow Transplant.*, 21:217-220, 1998.
Lee et al., *Ann. Hematol.*, 84:321-330, 2005.
Lehrnbecher et al., *Eur. J. Clin. Microbiol. Infect. Dis.*, 29:1043-1045, 2010.
Lewis and Kontoyiannis, *Med. Mycol.*, 47(Suppl 1):S271-281, 2009.
Lortholary et al., *Antimicrob. Agents Chemother.*, 54(10):4446-4450, 2010.
Madden et al., *Biol. Blood Marrow Transplant.*, 13:56-64, 2007.
Malley et al., *Fundam. Appl. Toxicol.*, 28:80-93, 1995.
Marcus and Goldman, *Lancet*, 2:1463, 1984.
Martell et al., *Ann. Intern. Med.*, 106:173, 1987.
Martin and Matzke, *J. Clin. Pharm.*, 1:42-48, 1982.
McDonald et al., *Ann. Intern. Med.*, 118:255-267, 1993.
McDonald et al., *Blood*, 101:2043-2048, 2003.
Meloni et al., *Ann. Oncol.*, 3:145-148, 1992.
Meloni et al., *Haematologica.*, 80:532-534, 1995.
Mosmann, *J. Immunol. Methods*, 65:55-63, 1983.
Notheis et al., *Mycoses*, 49(Suppl 1):37-41, 2006.
Okuda et al., *J. Occup. Health*, 3:154-160, 2006.
Pappas et al., *Clin. Infect. Dis.*, 15; 50(8):1101-1111, 2010.
Parthasarathy et al., *Cancer Chemother. Pharmacol.*, 34:527-34, 1994.
Person et al., *Infect. Dis. Clin. North Am.*, 24(2):439-459, 2010.
Peters et al., *Cancer Res.*, 47:6402-6406, 1987.
Russell et al., *Biol. Blood Marrow Transplant.*, 8:468-477, 2002.
Sadeghi et al., Proc. Amer. Assoc. *Cancer Res.*, (Abstr), 1999.
Santarone et al., *Biol. Blood Marrow Transplant.*, 2011 (E-Pub-ahead of print)
Santos and Tutschka, *J. Natl. Cancer Inst.*, 53:1781-1785, 1974.
Santos et al., *N. Engl. J. Med.*, 309:1347-1353, 1983.
Santos, *Bone Marrow Transplant.*, 4(Suppl 1):236-239, 1989.
Shimoni et al., *Leukemia*, 20:322-328, 2006.
Shimoni et al., *Leukemia*, 24:1050-1052, 2010.
Singh et al., *Transplantation*, 81(3):320-326, 2006.
Slattery et al., *Blood*, 89:3055-3060, 1997.
Socie et al., *Blood*, 98:3569-3574, 2001.
Spiegel and Noseworthy, *J. Pharm. Sci* 52:917-927, 1963.
Sureda et al., *Ann. Intern. Med.*, 111:543-544, 1989.
Thall et al., *Bone Marrow Transplant.*, 33:1191-1199, 2004.
The Food and Drug Administration, *The Federal Register*, Aug. 18, 2010.
The Merck Index. Busulfan. p. 253, 2001.
The Office of Environmental Health Hazard Assessment (OEHHA) within the California Environmental Protection Agency, Chemical Listed Effective May 21, 2010.
Tones et al., *Lancet Infect, Dis.*, 5(12):775-785, 2005.
Tutschka et al., *Blood*, 70:1382-1388, 1987.
Ullmann et al., *N. Engl. J. Med.*, 356(4):335-347, 2007.
Valentine et al., *Inhalation Toxicol.*, 9:141-158, 1997.
Van de Velde et al., *Pharmacotherapy*, 16(3):424-428, 1996.
Vassal et al., *Cancer Chemother. Pharmacol.*, 24:386-390, 1989.
Vassal et al., *Cancer Res.*, 50:6203-6207, 1990.
Vassal, *Anticancer Res.*, 14:2363-2370, 1994.
Vehreschild et al., *J. Antimicrob. Chemother.*, 65(7):1466-1471, 2010.
VICH Steering Committee, VICH GL 18 (R)—Intl. Coop. Harmonisation of Tech. Requirements for Registration of Veterinary Medicinal Products. (Rev. 9), 2010.
Walsh et al., *Antimicrob. Agents Chemother.*, 54(10):4116-4123, 2010.
Wang et al., *Leukemia*, 5:493-499, 1991.
Weiss et al., *Cancer Chemother. Rep.*, 16:477-485, 1962a.
Weiss et al., *Science*, 136:151-152, 1962b.
Willems et al., *J. Clin. Pharm. Ther* 26(3):159-169, 2001.
Wingard et al., *Blood*, 116(24):5111-5118, 2010.
Winston et al., *Biol. Blood Marrow Transplant.*, 2010 (e-pub).
Woestenborghs et al., *J. Chromatogr.*, 413:332-337, 1987.
Yalkowsky and Roseman, In: *Techniques of solubilization of drugs*, Yalkowsky (Ed.), Marcel Dekker Inc., N.Y., 91-134, 1981.
Zhou et al., *Clin. Pharmacol.*, 38(7):593-602, 1998.

What is claimed is:

1. A non-aqueous, homogeneous solution comprising a solubilized lipophilic pharmaceutical agent and an amphiphilic liquid polymeric solvent, the formulation being substantially free of non-polymeric organic solvents, water and non-solubilized particles, wherein the solubilized lipophilic pharmaceutical agent has a concentration of at least about 0.5 mg/mL, wherein the lipophilic pharmaceutical agent is busulfan and further wherein the solution is pharmaceutically acceptable for administration to a human patient.

2. The non-aqueous, homogeneous solution of claim 1, wherein the solution remains stable and free of non-solubilized particles for at least 40 days when stored at room temperature.

3. An aqueous, homogeneous, pharmaceutically-acceptable parenteral formulation, prepared by a process comprising obtaining a solution in accordance with claim 1, and diluting the solution with a desired aqueous diluent.

4. The solution of claim 1, wherein the solubilized lipophilic pharmaceutical agent has a concentration of about 1 to 10 mg/mL.

5. The solution of claim 4, wherein the solubilized lipophilic pharmaceutical agent has a concentration of about 3 to 9 mg/mL.

6. The solution of claim 1, wherein the solution does not comprise a surfactant.

7. The solution of claim 1, wherein said amphiphilic liquid polymeric solvent is comprised of a single polymer.

8. The solution of claim 1, wherein said amphiphilic liquid polymeric solvent is polyethylene glycol (PEG).

9. The solution of claim 8, wherein said PEG is selected from the group consisting of PEG-100, PEG-200, PEG-300, PEG-400, PEG-600 and PEG-800.

10. The solution of claim 1, wherein the solution further comprises a protonating agent.

11. The solution of claim 10, wherein the protonating agent is an acid, alcohol or acidified alcohol.

12. The solution of claim 11, wherein the acid is HCl, citric acid, acetic acid or glutamic acid.

13. The solution of claim 1, wherein the solution has a pH of from about 1 to about 6.

\* \* \* \* \*